US009173962B2

(12) United States Patent
Beau-Larvor et al.

(10) Patent No.: US 9,173,962 B2
(45) Date of Patent: Nov. 3, 2015

(54) ANTIGEN BINDING PROTEIN AND ITS USE AS ADDRESSING PRODUCT FOR THE TREATMENT OF CANCER

(71) Applicants: Charlotte Beau-Larvor, Jonzier Epagny (FR); Liliane Goetsch, Ayze (FR); Nicolas Boute, Cernex (FR)

(72) Inventors: Charlotte Beau-Larvor, Jonzier Epagny (FR); Liliane Goetsch, Ayze (FR); Nicolas Boute, Cernex (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 0 days.

(21) Appl. No.: 13/935,918

(22) Filed: Jul. 5, 2013

(65) Prior Publication Data

US 2014/0141023 A1 May 22, 2014

Related U.S. Application Data

(63) Continuation-in-part of application No. PCT/EP2012/071832, filed on Nov. 5, 2012.

(30) Foreign Application Priority Data

Nov. 3, 2011 (EP) ..................................... 11306416

(51) Int. Cl.
*G01N 33/53* (2006.01)
*A61K 47/48* (2006.01)
*C07K 14/71* (2006.01)
*C07K 16/28* (2006.01)
*C07K 16/32* (2006.01)
*C07K 16/30* (2006.01)
*G01N 33/68* (2006.01)
*A61K 39/00* (2006.01)

(52) U.S. Cl.
CPC ............ *A61K 47/48569* (2013.01); *C07K 14/71* (2013.01); *C07K 16/2803* (2013.01); *C07K 16/30* (2013.01); *C07K 16/32* (2013.01); *G01N 33/6854* (2013.01); *A61K 2039/505* (2013.01); *C07K 2317/76* (2013.01); *C07K 2317/77* (2013.01); *C07K 2319/30* (2013.01)

(58) Field of Classification Search
None
See application file for complete search history.

(56) References Cited

U.S. PATENT DOCUMENTS

| 4,970,198 | A | 11/1990 | Lee et al. |
|---|---|---|---|
| 5,079,233 | A | 1/1992 | Lee |
| 5,585,089 | A | 12/1996 | Queen et al. |
| 5,606,040 | A | 2/1997 | McGahren et al. |
| 5,693,762 | A | 12/1997 | Queen et al. |
| 5,739,116 | A | 4/1998 | Hamann et al. |
| 5,767,285 | A | 6/1998 | Hamann et al. |
| 5,773,001 | A | 6/1998 | Hamann et al. |

FOREIGN PATENT DOCUMENTS

| EP | 2 228 392 A1 | 9/2010 |
|---|---|---|
| EP | 2 270 053 A1 | 1/2011 |
| EP | 2 589 609 A1 | 5/2013 |
| WO | WO 2009/062690 A1 | 5/2009 |
| WO | WO 2010/014755 A1 | 2/2010 |
| WO | WO 2010/130751 A1 | 11/2010 |
| WO | WO 2011/014457 A1 | 2/2011 |
| WO | WO 2011/091305 A2 | 7/2011 |
| WO | WO 2013/064684 A1 | 5/2013 |
| WO | WO 2013/064685 A1 | 5/2013 |

OTHER PUBLICATIONS

Alley, C., et al., "The Pharmacologic Basis for Antibody-Auristatin Conjugate Activity," *J. Pharm. & Exp. Ther.*, 330:932-938 (2009).
Bebbington, C. R., et al., "High-Level Expression of a Recombinant Antibody From Myeloma Cells Using a Glutamine Synthetase Gene as an Amplifiable Selectable Marker," *Bio/Tech.*, 10:169-175 (1992).
Beck, A., et al., "The Next Generation of Antibody-drug Conjugates Comes of Age," *Disc. Med.*, 10:329-339 (2010).
Fraker, P.J. et al., "Protein and Cell Membrane Iodinations With a Sparingly Soluble Chloroamide, 1, 3, 4, 6-Tetrachloro-3a, 6a-Diphenylglycol URIL," *Biochem. & Biophy. Res. Comm.*, 80:849-857 (1978).
Hafizi, S. et al., "Gas6 and Protein S Vitamin K-Dependent Ligands for the Axl Receptor Tyrosine Kinase Subfamily," *FEBS J.*, 273:5231-5244 (2006).
Harlow, et al., "Antibodies a Laboratory Manual," Cold Spring Harbor Laboratory, 726 (1988).
Holland, S.J., et al., "Multiple Roles for the Receptor Tyrosine Kinase Axl in Tumor Formation," *Can. Res.* 65:9294-9303 (2005).
Hong, C.C. et al., "Receptor Tyrosine Kinase AXL is Induced by Chemotherapy Drugs and Overexpression of AXL Confers Drug Resistance in Acute Myeloid Leukemia," Can. Let., 268:314-324 (2008).
Jones, P. et al., "Replacing the Complementarity-Determining Regions in a Human Antibody With Those From a Mouse," *Nature*, 321:522-525 (1986).
Kabat, E. etal., Sequences of Proteins of Immunological Interest, 15th Ed. (1991).

(Continued)

Primary Examiner — Jacob Cheu
(74) Attorney, Agent, or Firm — Finnegan, Henderson, Farabow, Garrett & Dunner, L.L.P.

(57) ABSTRACT

The present invention relates to a novel antigen binding protein, in particular a monoclonal antibody, capable of binding specifically to the protein Axl as well as the amino and nucleic acid sequences coding for said protein. From one aspect, the invention relates to a novel antigen binding protein, or antigen binding fragments, capable of binding specifically to Axl and, by inducing internalization of Axl, being internalized into the cell. The invention also comprises the use of said antigen binding protein as an addressing product in conjugation with other anti-cancer compounds, such as toxins, radio-elements or drugs, and the use of same for the treatment of certain cancers.

8 Claims, 14 Drawing Sheets

(56) References Cited

OTHER PUBLICATIONS

Figure 1:
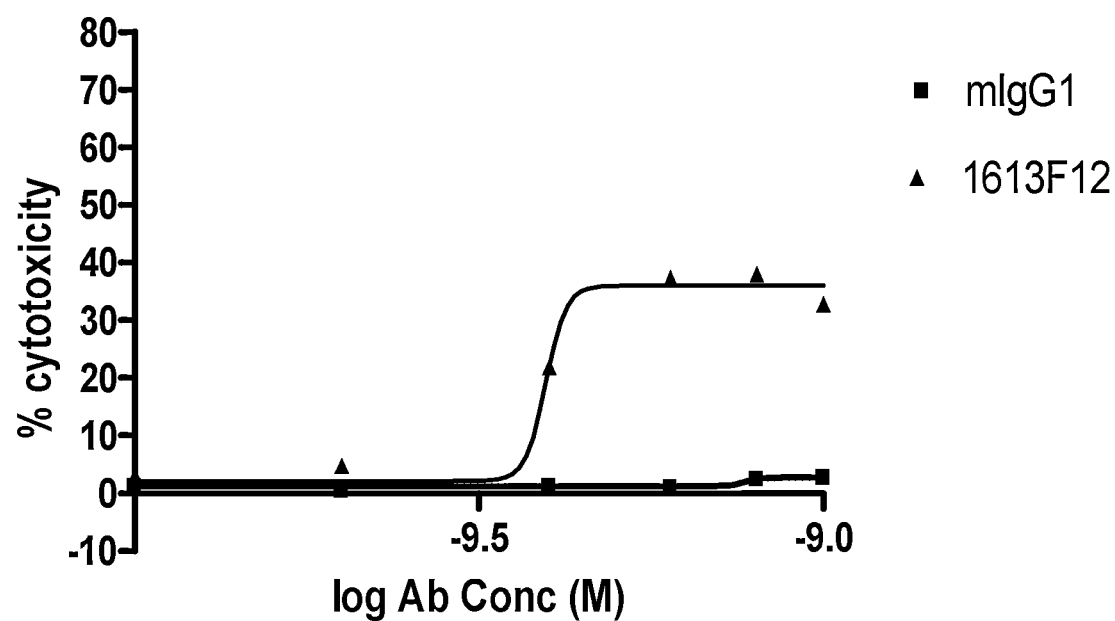

Keating, A.K. et al., "Inhibition of Mer and Axl Receptor Tyrosine Kinases in Astrocytoma Cells Leads to Increased Apoptosis and Improved Chemosensitivity," Mol. Can. Ther. 9:1298-1307 (2010).
Kohler et al., "Continuous Cultures of Fused Cells Secreting Antibody of Predefined Specificity," *Nature*, 256:495-497 (1975).
Korshunov, V. et al., "Axl, A Receptor Tyrosine Kinase, Mediates Flow-Induced Vascular Remodeling," *Circ. Res.*, 98:1446-1452 (2006).
Korshunov, V. et al., "Axl Mediates Vascular Remodeling Induced by Deoxycorticosterone Acetate-Salt Hypertension," *Circ. Res.*, 50:1057-1062 (2007).
Kaas, Q. et al., "IMGT Colliers de Perles: Standardized Sequence-Structure Representations of the IgSF and MhcSF Superfamily Domains," *Cur. BioForm.*, 2:21-30 (2007).
Kaas, Q. et al., "IMGT/3Dstructure-DB and IMGT/StructuralQuery, A Database and a Tool for Immunoglobulin, T Cell Receptor and HMC Structural Data," *Nuc. Acid. Res.*, 32:D208-D210 (2004).
Lay, J.D., et al., "Sulfasalazine Suppresses Drug Resistance and Invasiveness of Lung Adenocarcinoma Cells Expressing AXL," *Can. Res.*, 67:3878-3887 (2007).
Ledford, H., "Toxic Antibodies Blitz Tumors," Nature, 476:380-381 (2011).
Lefranc, M.P., "Unique Database Numbering System for Immunogenetic Analysis," *Imm. Today*, 18:509 (1997).
Lefranc, M.P., "The IMGT Unique Numbering for Immunoglobulins, T-Cell Receptors, and Ig-Like Domains," *The Imm.*, 7:132-136 (1999).
Lefranc, M.P. "IMGT Unique Numbering for Immunoglobulin and T Cell Receptor Variable Domains and Ig Superfamily V-Like Domains," *Devl. & Comp. Imm.*, 27:55-77 (2003).
Lemke, G. et al., "Immunobiology of the TAM Receptors," Nat. Rev. Immunol., 8:327-336 (2008).
Li, Y. et al., "Axl as a Potential Therapeutic Target in Cancer: Role of Axl in tumor Growth, Metastasis and Angiogenesis," *Oncog.*, 28:3442-3455 (2009).
Linger, R.M.A. etal., "TAM Receptor Tyronsine Kinases: Biologic Functions, Signaling, and Potential Therapeutic Targeting in Human Cancer," Adv. *Can. Res.*, 100:35-83 (2008).
Liu, L. et al., "Novel Mechanism of Lapatinib Resistance in HER2-Positive Breast Tumor Cells: Activation of AXL," *Can. Res.*, 69:6871-6878 (2009).
Liu, R. et al., "Induction, Regulation, and Biologic Function of Axl Receptor Tyrosine Kinase in Kaposi Sarcoma," *Blood*, 116:297-305 (2010).
MacLeod, K. etal., "Altered ErbB Receptor Signaling and Gene Expression in Cisplatin-Resistant Ovarian Cancer," *Can. Res.*, 65:6789-6800 (2005).
Mahadevan, D. et al., "A Novel Tyrosine Kinase Switch is a Mechanism of Imatinib Resistance in Gastrointestinal Stromal Tumors," *Oncogene*, 26:3903-3919 (2007).
Manfioletti, G. et al., "The Protein Encoded by a Growth Arrest-Specific Gene (*gas6*) is a New Member of the Vitamin K-Dependent Proteins Related to Protein S, A Negative Coregulator in the Blood Coagulation Cascade," *Mol. & Cell. Bio.*, 13:4976-4985 (1993).
Maxfield, F.R. et al., "Endocytic Recycling," *Nat. Rev. Mol. Cell. Bio.*, 5:121-132 (2004) Mountain, A., et al., "Engineering Antibodies for Therapy," *Biotechnol. Genet. Eng. Rev.*, 10:1-142 (1992).
Nagata, K. et al., "Identification of the Product of Growth Arrest-Specific Gene 6 as a Common Ligand for Axl, Sky, and Mer Receptor Tyrosine Kinases," *J. Bio. Chem.*, 271:30022-30027 (1996).

Needleman, S. et al., "A General Method Applicable to the Search for Similarities in the Amino Acid Sequence of Two Proteins," J. Mol. Biol., 48:443-453 (1970).
O'Bryan, J.P. et al., "Axl, A Transforming Gene Isolated From Primary Human Myeloin Leukemia Cells, Encodes a Novel Receptor Tyrosine Kinase," *Mol. & Cell Bio.*, 11:5016-5031 (1991).
Pearson, W.R. et al., "Improved Tools for Biological Sequence Comparison," *Proc. Natl. Acad. Sci. USA*, 85:2444-2448 (1988).
Phillips Lewis, G., et al, "Targeting HER2-Positive Breast Cancer With Trastuzumab-DM1, An Antibody-Cytotoxic Drug Conjugate," *Can. Res.* 68:9280-9290 (2008).
Riechmann, L. et al., "Reshaping Human Antibodies for Therapy," *Nature*, 332:323-327 (1988).
Ruiz, M. et al., "IMGT Gene Identification and Colliers de Perles of Human Immunoglobulins With Known 3D Structures," *Immuno.*, 53:857-883 (2002).
Sambrook, J. et al., "Molecular Cloning," $3^{rd\ Ed}$. (2001).
Sasaki, T. et al., "Structural Basis for Gas6-Axl Signaling," *The Embo J.*, 25:80-87 (2006).
Singer, I. et al., "Optimal Humanization of 1 B4, an Anti-CD18 Murine Monoclonal Antibody, is Achieved by Correct Choice of Human V-Region Framework Sequences," *J. of Immuno.*, 150:2844-2857 (1993).
Smith, T.F. et al., "Comparison of Biosequenses," *Adv. App. Math.*, 2:482-489 (1981).
Tatusova, T.A. et al., "Blast 2 Sequences, A New Tool for Comparing Protein and Nucleotide Sequences," *FEMS Microbio. Ltrs.*, 174:247-250 (1999).
Thiery, J.P. et al., "Epithlial-Mesenchymal Transistions in Development and Pathologies," *Curr. Opin. Cell Biol.*, 15:740-746 (2003).
Varnum, B.C. et al., "Axl Receptor Tyrosine Kinase Stimulated by the Vitamin K-Dependent Protein Encoded by Growth-Arrest-Specific Gene 6," *Nature*, 373:623-626 (1995).
Verhoeyen, M. et al., "Reshaping Human Antibodies: Grafting an Antilysozyme Activity," *Science*, 239:1534-1536 (1988).
Verma, A. et al., "Targeting Axl and Mer Kinases in Cancer," *Amer. Mol. Can. Ther.*, 10:1763-1772 (2011).
Wiseman, G. A. et al., "Ibritumomab Tiuxetan Radioimmunotherapy for Patients With Relapsed or Refractory Non-Hodgkin Lymphoma and Mild Thrombocytopenia: A Phase II Multicenter Trial," *Blood*, 99:4336-4342 (2002).
Wiseman, G.A., et al., "Phase I/II $^{90}$Y-Zevalin (Yttrium-90 Ibritumomab Tiuxetan, IDEC-Y2B8) Radioimmunotherapy Dosimetry Results in Relapsed or Refractory Non-Hodgkin's Lymphoma," *Euro. J. of Nuc. Med.*, 27:766-77 (2000).
Witzig, T.E. et al., "Treatment With Ibritumomab Tiuxetan Radioimmunotherapy in Patinets With Rituximab-Refractory Follicular Non-Hodgkin's Lymphoma," *J. Clin. Onc.*, 20:3262-3269 (2002).
Witzig, T.E. et al., "Randomized Controlled Trial of Yttrium-90-Labeled Ibritumomab Tiuxetan Radioimmunotherapy Versus Rituximab Immunotherapy for Patients With Relapsed or Refractory Low-Grade, Follicular, or Transformed B-Cell Non-Hodgkin's Lymphoma," *J. Clin. Onc.*, 20:24533-2463 (2002).
Ye, X. et al., "An Anti-Axl Monoclonal Antibody Attenuates Xenograft Tumor Growth and Enhances the Effect of Multiple Anticancer Therapies," *Oncogene*, 29:5254-5264 (2010).
Zhang, Y.X. et al, "AXL is a Potential Target for Therapeutic Intervention in Breast Cancer Progression," *Can. Res.*, 68:1905-1915 (2008).
International Search Report PCT/EP2012/071833, mailed Feb. 5, 2013.
International Search Report PCT/EP2012/071832, mailed Feb. 5, 2013.
Extended European Search Report European Patent Application 11306416.6 (also published as EP2589609) mailed Apr. 12, 2012.

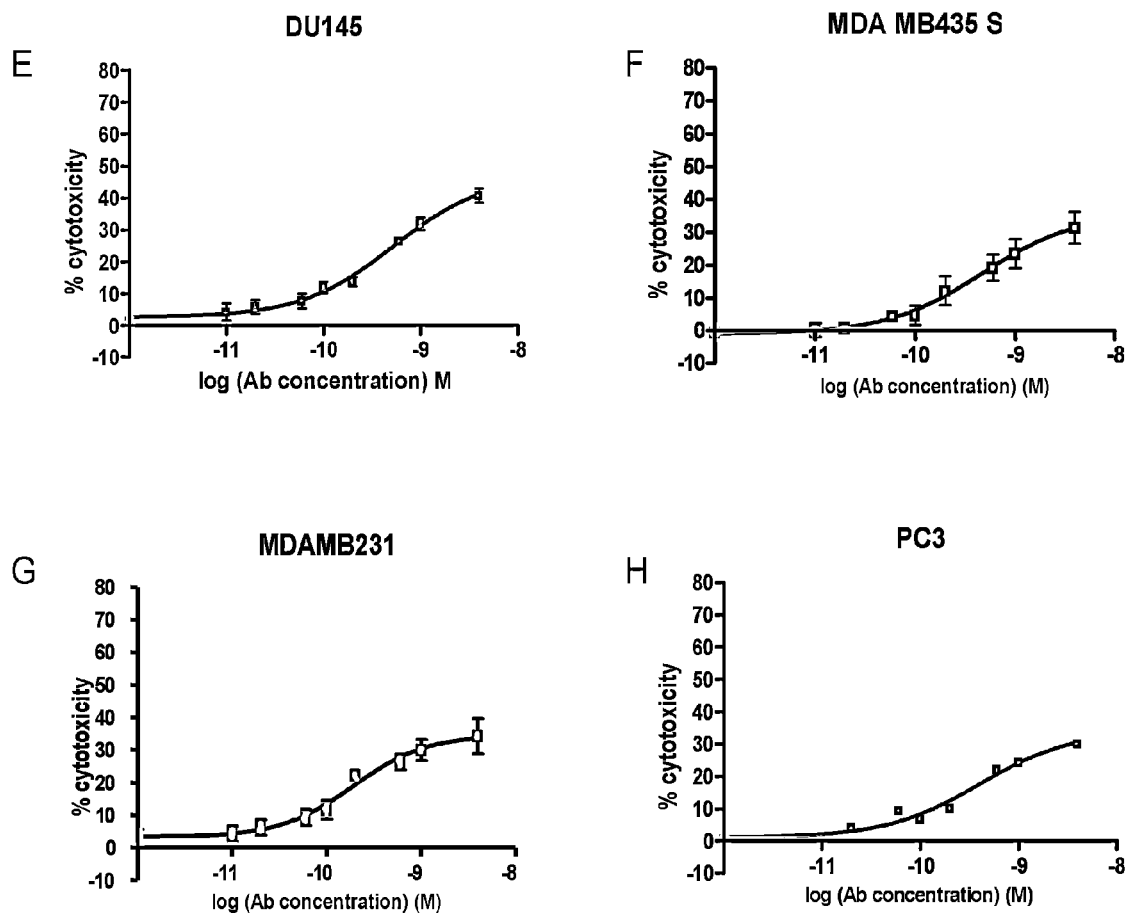
Figures 11A-11K (suite)

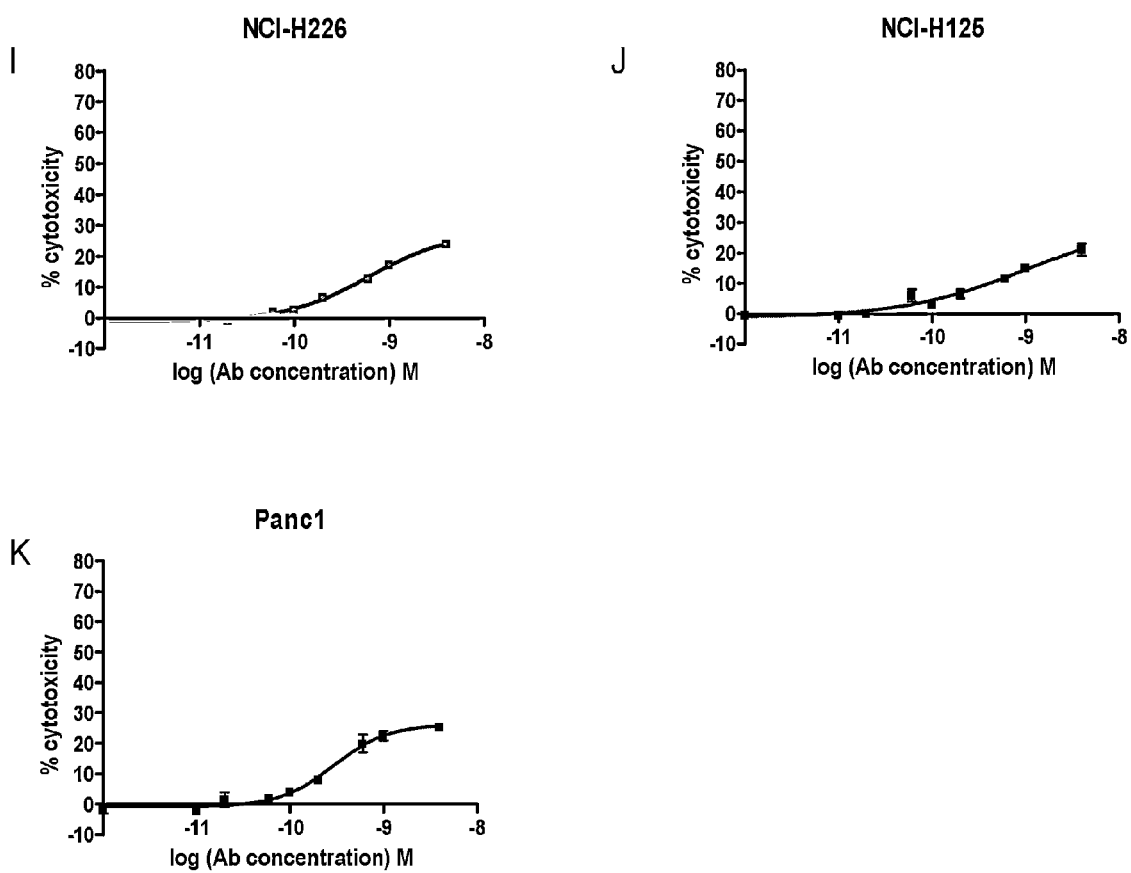
Figures 11A-11K (suite)

```
                              SEQUENCE LISTING

<160> NUMBER OF SEQ ID NOS: 35

<210> SEQ ID NO 1
<211> LENGTH: 6
<212> TYPE: PRT
<213> ORGANISM: artificial
<220> FEATURE:
<223> OTHER INFORMATION: Light chain CDR-L1 from 1613F12 antibody (IMGT
      numbering)

<400> SEQUENCE: 1

Lys Ser Ile Ser Lys Tyr
1               5

<210> SEQ ID NO 2
<211> LENGTH: 3
<212> TYPE: PRT
<213> ORGANISM: artificial
<220> FEATURE:
<223> OTHER INFORMATION: Light chain CDR-L2 from 1613F12 antibody (IMGT
      numbering)

<400> SEQUENCE: 2

Ser Gly Ser
1

<210> SEQ ID NO 3
<211> LENGTH: 9
<212> TYPE: PRT
<213> ORGANISM: artificial
<220> FEATURE:
<223> OTHER INFORMATION: Light chain CDR-L3 from 1613F12 antibody (IMGT
      numbering)

<400> SEQUENCE: 3

Gln Gln His His Glu Tyr Pro Leu Thr
1               5

<210> SEQ ID NO 4
<211> LENGTH: 8
<212> TYPE: PRT
<213> ORGANISM: artificial
<220> FEATURE:
<223> OTHER INFORMATION: Heavy chain CDR-H1 from 1613F12 antibody (IMGT
      numbering)

<400> SEQUENCE: 4

Gly Phe Asn Ile Arg Asp Thr Tyr
1               5

<210> SEQ ID NO 5
<211> LENGTH: 8
<212> TYPE: PRT
<213> ORGANISM: artificial
<220> FEATURE:
<223> OTHER INFORMATION: Heavy chain CDR-H2 from 1613F12 antibody (IMGT
      numbering)

<400> SEQUENCE: 5

Leu Asp Pro Ala Asn Gly His Thr
1               5
```

```
<210> SEQ ID NO 6
<211> LENGTH: 17
<212> TYPE: PRT
<213> ORGANISM: artificial
<220> FEATURE:
<223> OTHER INFORMATION: Heavy chain CDR-H3 from 1613F12 antibody (IMGT
      numbering)

<400> SEQUENCE: 6

Ala Arg Gly Ala Tyr Tyr Tyr Gly Ser Ser Gly Leu Phe Tyr Phe Asp
1               5                   10                  15

Tyr

<210> SEQ ID NO 7
<211> LENGTH: 107
<212> TYPE: PRT
<213> ORGANISM: artificial
<220> FEATURE:
<223> OTHER INFORMATION: Light chain Mu variable domain

<400> SEQUENCE: 7

Asp Val Gln Ile Thr Gln Ser Pro Ser Tyr Leu Ala Thr Ser Pro Gly
1               5                   10                  15

Glu Thr Ile Thr Ile Asn Cys Arg Ala Ser Lys Ser Ile Ser Lys Tyr
            20                  25                  30

Leu Ala Trp Tyr Gln Glu Lys Pro Gly Lys Thr Asn Lys Leu Leu Ile
        35                  40                  45

Tyr Ser Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Met Tyr Phe Cys Gln Gln His His Glu Tyr Pro Leu
                85                  90                  95

Thr Phe Gly Ala Gly Thr Glu Leu Glu Leu Lys
            100                 105

<210> SEQ ID NO 8
<211> LENGTH: 124
<212> TYPE: PRT
<213> ORGANISM: artificial
<220> FEATURE:
<223> OTHER INFORMATION: Heavy chain Mu variable domain

<400> SEQUENCE: 8

Glu Val His Leu Gln Gln Ser Gly Ala Glu Leu Val Lys Pro Gly Ala
1               5                   10                  15

Ser Val Lys Leu Ser Cys Thr Ala Ser Gly Phe Asn Ile Arg Asp Thr
            20                  25                  30

Tyr Ile His Trp Val Lys Gln Arg Pro Glu Gln Gly Leu Glu Trp Ile
        35                  40                  45

Gly Arg Leu Asp Pro Ala Asn Gly His Thr Lys Tyr Gly Pro Asn Phe
    50                  55                  60

Gln Gly Arg Ala Thr Met Thr Ser Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Gly Ala Tyr Tyr Tyr Gly Ser Ser Gly Leu Phe Tyr Phe Asp
            100                 105                 110

Tyr Trp Gly Gln Gly Thr Thr Leu Ser Val Ser Ser
        115                 120
```

```
<210> SEQ ID NO 9
<211> LENGTH: 11
<212> TYPE: PRT
<213> ORGANISM: artificial
<220> FEATURE:
<223> OTHER INFORMATION: Light chain CDR-L1 from 1613F12 antibody (Kabat
      numbering)

<400> SEQUENCE: 9

Arg Ala Ser Lys Ser Ile Ser Lys Tyr Leu Ala
1               5                   10

<210> SEQ ID NO 10
<211> LENGTH: 7
<212> TYPE: PRT
<213> ORGANISM: artificial
<220> FEATURE:
<223> OTHER INFORMATION: Light chain CDR-L2 from 1613F12 antibody (Kabat
      numbering)

<400> SEQUENCE: 10

Ser Gly Ser Thr Leu Gln Ser
1               5

<210> SEQ ID NO 11
<211> LENGTH: 9
<212> TYPE: PRT
<213> ORGANISM: artificial
<220> FEATURE:
<223> OTHER INFORMATION: Light chain CDR-L3 from 1613F12 antibody (Kabat
      numbering)

<400> SEQUENCE: 11

Gln Gln His His Glu Tyr Pro Leu Thr
1               5

<210> SEQ ID NO 12
<211> LENGTH: 6
<212> TYPE: PRT
<213> ORGANISM: artificial
<220> FEATURE:
<223> OTHER INFORMATION: Heavy chain CDR-H1 from 1613F12 antibody (Kabat
      numbering)

<400> SEQUENCE: 12

Arg Asp Thr Tyr Ile His
1               5

<210> SEQ ID NO 13
<211> LENGTH: 17
<212> TYPE: PRT
<213> ORGANISM: artificial
<220> FEATURE:
<223> OTHER INFORMATION: Heavy chain CDR-H2 from 1613F12 antibody (Kabat
      numbering)

<400> SEQUENCE: 13

Arg Leu Asp Pro Ala Asn Gly His Thr Lys Tyr Gly Pro Asn Phe Gln
1               5                   10                  15

Gly

<210> SEQ ID NO 14
<211> LENGTH: 15
<212> TYPE: PRT
<213> ORGANISM: artificial
<220> FEATURE:
<223> OTHER INFORMATION: Heavy chain CDR-H3 from 1613F12 antibody (Kabat
      numbering)
```

-continued

<400> SEQUENCE: 14

Gly Ala Tyr Tyr Tyr Gly Ser Ser Gly Leu Phe Tyr Phe Asp Tyr
1               5                   10                  15

<210> SEQ ID NO 15
<211> LENGTH: 18
<212> TYPE: DNA
<213> ORGANISM: artificial
<220> FEATURE:
<223> OTHER INFORMATION: Light chain CDR-L1 from 1613F12 antibody (IMGT
      numbering)

<400> SEQUENCE: 15
aagagcatta gcaaatat                                                18

<210> SEQ ID NO 16
<211> LENGTH: 9
<212> TYPE: DNA
<213> ORGANISM: artificial
<220> FEATURE:
<223> OTHER INFORMATION: Light chain CDR-L2 from 1613F12 antibody (IMGT
      numbering)

<400> SEQUENCE: 16 tctggatcc                                                           9

<210> SEQ ID NO 17
<211> LENGTH: 27
<212> TYPE: DNA
<213> ORGANISM: artificial
<220> FEATURE:
<223> OTHER INFORMATION: Light chain CDR-L3 from 1613F12 antibody (IMGT
      numbering)

<400> SEQUENCE: 17
caacagcatc atgaataccc gctcacg                                      27

<210> SEQ ID NO 18
<211> LENGTH: 24
<212> TYPE: DNA
<213> ORGANISM: artificial
<220> FEATURE:
<223> OTHER INFORMATION: Heavy chain CDR-H1 from 1613F12 antibody (IMGT
      numbering)

<400> SEQUENCE: 18
ggcttcaaca ttagagacac ctat                                         24

<210> SEQ ID NO 19
<211> LENGTH: 24
<212> TYPE: DNA
<213> ORGANISM: artificial
<220> FEATURE:
<223> OTHER INFORMATION: Heavy chain CDR-H2 from 1613F12 antibody (IMGT
      numbering)

<400> SEQUENCE: 19
cttgatcctg cgaatggtca tact                                         24

<210> SEQ ID NO 20
<211> LENGTH: 51
<212> TYPE: DNA
<213> ORGANISM: artificial
<220> FEATURE:
<223> OTHER INFORMATION: Heavy chain CDR-H3 from 1613F12 antibody (IMGT
      numbering)

<400> SEQUENCE: 20

```
gctagagggg cctattacta cggtagtagt ggtctcttct actttgacta c          51
```

<210> SEQ ID NO 21
<211> LENGTH: 321
<212> TYPE: DNA
<213> ORGANISM: artificial
<220> FEATURE:
<223> OTHER INFORMATION: Light chain Mu variable domain

<400> SEQUENCE: 21

```
gatgtccaga taacccagtc tccatcttat cttgctacat ctcctggaga aaccattact    60
attaattgca gggcaagtaa gagcattagc aaatatttag cctggtatca agaaaaacct   120
gggaaaacta ataagcttct tatctactct ggatccactt tgcaatctgg agttccatca   180
aggttcagtg gcagtggatc tggtacagat ttcactctca ccatcagtag cctggagcct   240
gaagattttg caatgtattt ctgtcaacag catcatgaat accgctcac gttcggtgct    300
gggaccgagc tggagctgaa a                                             321
```

<210> SEQ ID NO 22
<211> LENGTH: 372
<212> TYPE: DNA
<213> ORGANISM: artificial
<220> FEATURE:
<223> OTHER INFORMATION: Heavy chain Mu variable domain

<400> SEQUENCE: 22

```
gaggttcacc tgcagcagtc tggggcagag cttgtgaagc caggggcctc agtcaagttg    60
tcctgcacag cttctggctt caacattaga gacacctata tccattgggt gaaacagagg   120
cctgaacagg gcctggagtg gattggaagg cttgatcctg cgaatggtca tactaaatat   180
ggcccgaact tccagggcag ggccactatg acatcagaca catcctccaa cacggcctac   240
ctgcagctca gcagcctgac atctgaggac actgccgtct attactgtgc tagagggcc    300
tattactacg gtagtagtgg tctcttctac tttgactact ggggccaagg caccactctc   360
tcagtctcct ca                                                        372
```

<210> SEQ ID NO 23
<211> LENGTH: 33
<212> TYPE: DNA
<213> ORGANISM: artificial
<220> FEATURE:
<223> OTHER INFORMATION: Light chain CDR-L1 from 1613F12 antibody (Kabat
      numbering)

<400> SEQUENCE: 23

```
agggcaagta agagcattag caaatattta gcc                                  33
```

<210> SEQ ID NO 24
<211> LENGTH: 21
<212> TYPE: DNA
<213> ORGANISM: artificial
<220> FEATURE:
<223> OTHER INFORMATION: Light chain CDR-L2 from 1613F12 antibody (Kabat
      numbering)

<400> SEQUENCE: 24

```
tctggatcca ctttgcaatc t                                               21
```

<210> SEQ ID NO 25
<211> LENGTH: 27

```
<212> TYPE: DNA
<213> ORGANISM: artificial
<220> FEATURE:
<223> OTHER INFORMATION: Light chain CDR-L3 from 1613F12 antibody (Kabat
      numbering)

<400> SEQUENCE: 25
caacagcatc atgaataccc gctcacg                                          27

<210> SEQ ID NO 26
<211> LENGTH: 18
<212> TYPE: DNA
<213> ORGANISM: artificial
<220> FEATURE:
<223> OTHER INFORMATION: Heavy chain CDR-H1 from 1613F12 antibody (Kabat
      numbering)

<400> SEQUENCE: 26
agagacacct atatccat                                                    18

<210> SEQ ID NO 27
<211> LENGTH: 51
<212> TYPE: DNA
<213> ORGANISM: artificial
<220> FEATURE:
<223> OTHER INFORMATION: Heavy chain CDR-H2 from 1613F12 antibody (Kabat
      numbering)

<400> SEQUENCE: 27
aggcttgatc ctgcgaatgg tcatactaaa tatgcccga acttccaggg c                 51

<210> SEQ ID NO 28
<211> LENGTH: 45
<212> TYPE: DNA
<213> ORGANISM: artificial
<220> FEATURE:
<223> OTHER INFORMATION: Heavy chain CDR-H3 from 1613F12 antibody (Kabat
      numbering)

<400> SEQUENCE: 28
ggggcctatt actacggtag tagtggtctc ttctactttg actac                      45

<210> SEQ ID NO 29
<211> LENGTH: 894
<212> TYPE: PRT
<213> ORGANISM: homo sapiens
<220> FEATURE:
<221> NAME/KEY: misc_feature
<223> OTHER INFORMATION: Protein Axl (with peptide signal)

<400> SEQUENCE: 29
```

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr

```
            100                 105                 110
Gly Gln Tyr Gln Cys Leu Val Phe Leu Gly His Gln Thr Phe Val Ser
            115                 120                 125
Gln Pro Gly Tyr Val Gly Leu Glu Gly Leu Pro Tyr Phe Leu Glu Glu
            130                 135             140
Pro Glu Asp Arg Thr Val Ala Ala Asn Thr Pro Phe Asn Leu Ser Cys
145                 150                 155                 160
Gln Ala Gln Gly Pro Pro Glu Pro Val Asp Leu Leu Trp Leu Gln Asp
                    165                 170                 175
Ala Val Pro Leu Ala Thr Ala Pro Gly His Gly Pro Gln Arg Ser Leu
            180                 185                 190
His Val Pro Gly Leu Asn Lys Thr Ser Ser Phe Ser Cys Glu Ala His
            195                 200                 205
Asn Ala Lys Gly Val Thr Thr Ser Arg Thr Ala Thr Ile Thr Val Leu
            210                 215                 220
Pro Gln Gln Pro Arg Asn Leu His Leu Val Ser Arg Gln Pro Thr Glu
225                 230                 235                 240
Leu Glu Val Ala Trp Thr Pro Gly Leu Ser Gly Ile Tyr Pro Leu Thr
                    245                 250                 255
His Cys Thr Leu Gln Ala Val Leu Ser Asn Asp Gly Met Gly Ile Gln
            260                 265                 270
Ala Gly Glu Pro Asp Pro Pro Glu Glu Pro Leu Thr Ser Gln Ala Ser
            275                 280                 285
Val Pro Pro His Gln Leu Arg Leu Gly Ser Leu His Pro His Thr Pro
            290                 295                 300
Tyr His Ile Arg Val Ala Cys Thr Ser Ser Gln Gly Pro Ser Ser Trp
305                 310                 315                 320
Thr His Trp Leu Pro Val Glu Thr Pro Glu Gly Val Pro Leu Gly Pro
                    325                 330                 335
Pro Glu Asn Ile Ser Ala Thr Arg Asn Gly Ser Gln Ala Phe Val His
            340                 345                 350
Trp Gln Glu Pro Arg Ala Pro Leu Gln Gly Thr Leu Leu Gly Tyr Arg
            355                 360                 365
Leu Ala Tyr Gln Gly Gln Asp Thr Pro Glu Val Leu Met Asp Ile Gly
            370                 375             380
Leu Arg Gln Glu Val Thr Leu Glu Leu Gln Gly Asp Gly Ser Val Ser
385                 390                 395                 400
Asn Leu Thr Val Cys Val Ala Ala Tyr Thr Ala Ala Gly Asp Gly Pro
                    405                 410                 415
Trp Ser Leu Pro Val Pro Leu Glu Ala Trp Arg Pro Gly Gln Ala Gln
            420                 425                 430
Pro Val His Gln Leu Val Lys Glu Pro Ser Thr Pro Ala Phe Ser Trp
            435                 440                 445
Pro Trp Trp Tyr Val Leu Leu Gly Ala Val Val Ala Ala Ala Cys Val
            450                 455                 460
Leu Ile Leu Ala Leu Phe Leu Val His Arg Arg Lys Lys Glu Thr Arg
465                 470                 475                 480
Tyr Gly Glu Val Phe Glu Pro Thr Val Glu Arg Gly Glu Leu Val Val
                    485                 490                 495
Arg Tyr Arg Val Arg Lys Ser Tyr Ser Arg Arg Thr Thr Glu Ala Thr
                    500                 505                 510
Leu Asn Ser Leu Gly Ile Ser Glu Glu Leu Lys Glu Lys Leu Arg Asp
            515                 520                 525
```

Val Met Val Asp Arg His Lys Val Ala Leu Gly Lys Thr Leu Gly Glu
        530                 535                 540

Gly Glu Phe Gly Ala Val Met Glu Gly Gln Leu Asn Gln Asp Asp Ser
545                 550                 555                 560

Ile Leu Lys Val Ala Val Lys Thr Met Lys Ile Ala Ile Cys Thr Arg
                565                 570                 575

Ser Glu Leu Glu Asp Phe Leu Ser Glu Ala Val Cys Met Lys Glu Phe
            580                 585                 590

Asp His Pro Asn Val Met Arg Leu Ile Gly Val Cys Phe Gln Gly Ser
        595                 600                 605

Glu Arg Glu Ser Phe Pro Ala Pro Val Val Ile Leu Pro Phe Met Lys
610                 615                 620

His Gly Asp Leu His Ser Phe Leu Leu Tyr Ser Arg Leu Gly Asp Gln
625                 630                 635                 640

Pro Val Tyr Leu Pro Thr Gln Met Leu Val Lys Phe Met Ala Asp Ile
                645                 650                 655

Ala Ser Gly Met Glu Tyr Leu Ser Thr Lys Arg Phe Ile His Arg Asp
            660                 665                 670

Leu Ala Ala Arg Asn Cys Met Leu Asn Glu Asn Met Ser Val Cys Val
        675                 680                 685

Ala Asp Phe Gly Leu Ser Lys Lys Ile Tyr Asn Gly Asp Tyr Tyr Arg
690                 695                 700

Gln Gly Arg Ile Ala Lys Met Pro Val Lys Trp Ile Ala Ile Glu Ser
705                 710                 715                 720

Leu Ala Asp Arg Val Tyr Thr Ser Lys Ser Asp Val Trp Ser Phe Gly
                725                 730                 735

Val Thr Met Trp Glu Ile Ala Thr Arg Gly Gln Thr Pro Tyr Pro Gly
            740                 745                 750

Val Glu Asn Ser Glu Ile Tyr Asp Tyr Leu Arg Gln Gly Asn Arg Leu
        755                 760                 765

Lys Gln Pro Ala Asp Cys Leu Asp Gly Leu Tyr Ala Leu Met Ser Arg
770                 775                 780

Cys Trp Glu Leu Asn Pro Gln Asp Arg Pro Ser Phe Thr Glu Leu Arg
785                 790                 795                 800

Glu Asp Leu Glu Asn Thr Leu Lys Ala Leu Pro Pro Ala Gln Glu Pro
                805                 810                 815

Asp Glu Ile Leu Tyr Val Asn Met Asp Glu Gly Gly Gly Tyr Pro Glu
            820                 825                 830

Pro Pro Gly Ala Ala Gly Gly Ala Asp Pro Pro Thr Gln Pro Asp Pro
        835                 840                 845

Lys Asp Ser Cys Ser Cys Leu Thr Ala Ala Glu Val His Pro Ala Gly
850                 855                 860

Arg Tyr Val Leu Cys Pro Ser Thr Thr Pro Ser Pro Ala Gln Pro Ala
865                 870                 875                 880

Asp Arg Gly Ser Pro Ala Ala Pro Gly Gln Glu Asp Gly Ala
                885                 890

<210> SEQ ID NO 30
<211> LENGTH: 869
<212> TYPE: PRT
<213> ORGANISM: homo sapiens
<220> FEATURE:
<221> NAME/KEY: misc_feature
<223> OTHER INFORMATION: Protein Axl (without peptide signal)

```
<400> SEQUENCE: 30

Ala Pro Arg Gly Thr Gln Ala Glu Glu Ser Pro Phe Val Gly Asn Pro
1               5                   10                  15

Gly Asn Ile Thr Gly Ala Arg Gly Leu Thr Gly Thr Leu Arg Cys Gln
            20                  25                  30

Leu Gln Val Gln Gly Glu Pro Pro Glu Val His Trp Leu Arg Asp Gly
        35                  40                  45

Gln Ile Leu Glu Leu Ala Asp Ser Thr Gln Thr Gln Val Pro Leu Gly
50                  55                  60

Glu Asp Glu Gln Asp Asp Trp Ile Val Val Ser Gln Leu Arg Ile Thr
65                  70                  75                  80

Ser Leu Gln Leu Ser Asp Thr Gly Gln Tyr Gln Cys Leu Val Phe Leu
                85                  90                  95

Gly His Gln Thr Phe Val Ser Gln Pro Gly Tyr Val Gly Leu Glu Gly
            100                 105                 110

Leu Pro Tyr Phe Leu Glu Glu Pro Glu Asp Arg Thr Val Ala Ala Asn
        115                 120                 125

Thr Pro Phe Asn Leu Ser Cys Gln Ala Gln Gly Pro Pro Glu Pro Val
130                 135                 140

Asp Leu Leu Trp Leu Gln Asp Ala Val Pro Leu Ala Thr Ala Pro Gly
145                 150                 155                 160

His Gly Pro Gln Arg Ser Leu His Val Pro Gly Leu Asn Lys Thr Ser
                165                 170                 175

Ser Phe Ser Cys Glu Ala His Asn Ala Lys Gly Val Thr Thr Ser Arg
            180                 185                 190

Thr Ala Thr Ile Thr Val Leu Pro Gln Gln Pro Arg Asn Leu His Leu
        195                 200                 205

Val Ser Arg Gln Pro Thr Glu Leu Glu Val Ala Trp Thr Pro Gly Leu
210                 215                 220

Ser Gly Ile Tyr Pro Leu Thr His Cys Thr Leu Gln Ala Val Leu Ser
225                 230                 235                 240

Asn Asp Gly Met Gly Ile Gln Ala Gly Glu Pro Asp Pro Pro Glu Glu
                245                 250                 255

Pro Leu Thr Ser Gln Ala Ser Val Pro Pro His Gln Leu Arg Leu Gly
            260                 265                 270

Ser Leu His Pro His Thr Pro Tyr His Ile Arg Val Ala Cys Thr Ser
        275                 280                 285

Ser Gln Gly Pro Ser Ser Trp Thr His Trp Leu Pro Val Glu Thr Pro
290                 295                 300

Glu Gly Val Pro Leu Gly Pro Pro Glu Asn Ile Ser Ala Thr Arg Asn
305                 310                 315                 320

Gly Ser Gln Ala Phe Val His Trp Gln Glu Pro Arg Ala Pro Leu Gln
                325                 330                 335

Gly Thr Leu Leu Gly Tyr Arg Leu Ala Tyr Gln Gly Gln Asp Thr Pro
            340                 345                 350

Glu Val Leu Met Asp Ile Gly Leu Arg Gln Glu Val Thr Leu Glu Leu
        355                 360                 365

Gln Gly Asp Gly Ser Val Ser Asn Leu Thr Val Cys Val Ala Ala Tyr
370                 375                 380

Thr Ala Ala Gly Asp Gly Pro Trp Ser Leu Pro Val Pro Leu Glu Ala
385                 390                 395                 400

Trp Arg Pro Gly Gln Ala Gln Pro Val His Gln Leu Val Lys Glu Pro
                405                 410                 415
```

```
Ser Thr Pro Ala Phe Ser Trp Pro Trp Trp Tyr Val Leu Leu Gly Ala
            420             425                 430

Val Val Ala Ala Ala Cys Val Leu Ile Leu Ala Leu Phe Leu Val His
            435             440                 445

Arg Arg Lys Lys Glu Thr Arg Tyr Gly Glu Val Phe Glu Pro Thr Val
            450             455                 460

Glu Arg Gly Glu Leu Val Val Arg Tyr Arg Val Arg Lys Ser Tyr Ser
465             470                 475                 480

Arg Arg Thr Thr Glu Ala Thr Leu Asn Ser Leu Gly Ile Ser Glu Glu
            485             490                 495

Leu Lys Glu Lys Leu Arg Asp Val Met Val Asp Arg His Lys Val Ala
            500             505                 510

Leu Gly Lys Thr Leu Gly Glu Gly Glu Phe Gly Ala Val Met Glu Gly
            515             520                 525

Gln Leu Asn Gln Asp Asp Ser Ile Leu Lys Val Ala Val Lys Thr Met
            530             535                 540

Lys Ile Ala Ile Cys Thr Arg Ser Glu Leu Glu Asp Phe Leu Ser Glu
545             550                 555                 560

Ala Val Cys Met Lys Glu Phe Asp His Pro Asn Val Met Arg Leu Ile
            565             570                 575

Gly Val Cys Phe Gln Gly Ser Glu Arg Glu Ser Phe Pro Ala Pro Val
            580             585                 590

Val Ile Leu Pro Phe Met Lys His Gly Asp Leu His Ser Phe Leu Leu
            595             600                 605

Tyr Ser Arg Leu Gly Asp Gln Pro Val Tyr Leu Pro Thr Gln Met Leu
            610             615                 620

Val Lys Phe Met Ala Asp Ile Ala Ser Gly Met Glu Tyr Leu Ser Thr
625             630                 635                 640

Lys Arg Phe Ile His Arg Asp Leu Ala Ala Arg Asn Cys Met Leu Asn
            645             650                 655

Glu Asn Met Ser Val Cys Val Ala Asp Phe Gly Leu Ser Lys Lys Ile
            660             665                 670

Tyr Asn Gly Asp Tyr Tyr Arg Gln Gly Arg Ile Ala Lys Met Pro Val
            675             680                 685

Lys Trp Ile Ala Ile Glu Ser Leu Ala Asp Arg Val Tyr Thr Ser Lys
            690             695                 700

Ser Asp Val Trp Ser Phe Gly Val Thr Met Trp Glu Ile Ala Thr Arg
705             710                 715                 720

Gly Gln Thr Pro Tyr Pro Gly Val Glu Asn Ser Glu Ile Tyr Asp Tyr
            725             730                 735

Leu Arg Gln Gly Asn Arg Leu Lys Gln Pro Ala Asp Cys Leu Asp Gly
            740             745                 750

Leu Tyr Ala Leu Met Ser Arg Cys Trp Glu Leu Asn Pro Gln Asp Arg
            755             760                 765

Pro Ser Phe Thr Glu Leu Arg Glu Asp Leu Glu Asn Thr Leu Lys Ala
            770             775                 780

Leu Pro Pro Ala Gln Glu Pro Asp Glu Ile Leu Tyr Val Asn Met Asp
785             790                 795                 800

Glu Gly Gly Gly Tyr Pro Glu Pro Gly Ala Ala Gly Gly Ala Asp
            805             810                 815

Pro Pro Thr Gln Pro Asp Pro Lys Asp Ser Cys Ser Cys Leu Thr Ala
            820             825                 830
```

```
Ala Glu Val His Pro Ala Gly Arg Tyr Val Leu Cys Pro Ser Thr Thr
            835                 840                 845

Pro Ser Pro Ala Gln Pro Ala Asp Arg Gly Ser Pro Ala Ala Pro Gly
850                 855                 860

Gln Glu Asp Gly Ala
865

<210> SEQ ID NO 31
<211> LENGTH: 451
<212> TYPE: PRT
<213> ORGANISM: homo sapiens
<220> FEATURE:
<221> NAME/KEY: misc_feature
<223> OTHER INFORMATION: extracellular domain of the protein Axl (with
      the peptide signal)

<400> SEQUENCE: 31

Met Ala Trp Arg Cys Pro Arg Met Gly Arg Val Pro Leu Ala Trp Cys
1               5                   10                  15

Leu Ala Leu Cys Gly Trp Ala Cys Met Ala Pro Arg Gly Thr Gln Ala
            20                  25                  30

Glu Glu Ser Pro Phe Val Gly Asn Pro Gly Asn Ile Thr Gly Ala Arg
        35                  40                  45

Gly Leu Thr Gly Thr Leu Arg Cys Gln Leu Gln Val Gln Gly Glu Pro
    50                  55                  60

Pro Glu Val His Trp Leu Arg Asp Gly Gln Ile Leu Glu Leu Ala Asp
65                  70                  75                  80

Ser Thr Gln Thr Gln Val Pro Leu Gly Glu Asp Glu Gln Asp Asp Trp
                85                  90                  95

Ile Val Val Ser Gln Leu Arg Ile Thr Ser Leu Gln Leu Ser Asp Thr
            100                 105                 110

Gly Gln Tyr Gln Cys Leu Val Phe Leu Gly His Gln Thr Phe Val Ser
        115                 120                 125

Gln Pro Gly Tyr Val Gly Leu Glu Gly Leu Pro Tyr Phe Leu Glu Glu
    130                 135                 140

Pro Glu Asp Arg Thr Val Ala Ala Asn Thr Pro Phe Asn Leu Ser Cys
145                 150                 155                 160

Gln Ala Gln Gly Pro Pro Glu Pro Val Asp Leu Leu Trp Leu Gln Asp
                165                 170                 175

Ala Val Pro Leu Ala Thr Ala Pro Gly His Gly Pro Gln Arg Ser Leu
            180                 185                 190

His Val Pro Gly Leu Asn Lys Thr Ser Ser Phe Ser Cys Glu Ala His
        195                 200                 205

Asn Ala Lys Gly Val Thr Thr Ser Arg Thr Ala Thr Ile Thr Val Leu
    210                 215                 220

Pro Gln Gln Pro Arg Asn Leu His Leu Val Ser Arg Gln Pro Thr Glu
225                 230                 235                 240

Leu Glu Val Ala Trp Thr Pro Gly Leu Ser Gly Ile Tyr Pro Leu Thr
                245                 250                 255

His Cys Thr Leu Gln Ala Val Leu Ser Asn Asp Gly Met Gly Ile Gln
            260                 265                 270

Ala Gly Glu Pro Asp Pro Pro Glu Pro Leu Thr Ser Gln Ala Ser
        275                 280                 285

Val Pro Pro His Gln Leu Arg Leu Gly Ser Leu His Pro His Thr Pro
    290                 295                 300

Tyr His Ile Arg Val Ala Cys Thr Ser Ser Gln Gly Pro Ser Ser Trp
```

```
                305                 310                 315                 320
        Thr His Trp Leu Pro Val Glu Thr Pro Glu Gly Val Pro Leu Gly Pro
                        325                 330                 335

Pro Glu Asn Ile Ser Ala Thr Arg Asn Gly Ser Gln Ala Phe Val His
                        340                 345                 350

Trp Gln Glu Pro Arg Ala Pro Leu Gln Gly Thr Leu Leu Gly Tyr Arg
                        355                 360                 365

Leu Ala Tyr Gln Gly Gln Asp Thr Pro Glu Val Leu Met Asp Ile Gly
                        370                 375                 380

Leu Arg Gln Glu Val Thr Leu Glu Leu Gln Gly Asp Gly Ser Val Ser
        385                 390                 395                 400

Asn Leu Thr Val Cys Val Ala Ala Tyr Thr Ala Ala Gly Asp Gly Pro
                        405                 410                 415

Trp Ser Leu Pro Val Pro Leu Glu Ala Trp Arg Pro Gly Gln Ala Gln
                        420                 425                 430

Pro Val His Gln Leu Val Lys Glu Pro Ser Thr Pro Ala Phe Ser Trp
                        435                 440                 445

Pro Trp Trp
                450

<210> SEQ ID NO 32
<211> LENGTH: 426
<212> TYPE: PRT
<213> ORGANISM: homo sapiens
<220> FEATURE:
<221> NAME/KEY: misc_feature
<223> OTHER INFORMATION: extracellular domain of the protein Axl
      (without the peptide signal)

<400> SEQUENCE: 32

Ala Pro Arg Gly Thr Gln Ala Glu Glu Ser Pro Phe Val Gly Asn Pro
        1               5                   10                  15

Gly Asn Ile Thr Gly Ala Arg Gly Leu Thr Gly Thr Leu Arg Cys Gln
                        20                  25                  30

Leu Gln Val Gln Gly Glu Pro Pro Glu Val His Trp Leu Arg Asp Gly
                        35                  40                  45

Gln Ile Leu Glu Leu Ala Asp Ser Thr Gln Thr Gln Val Pro Leu Gly
                50                  55                  60

Glu Asp Glu Gln Asp Asp Trp Ile Val Val Ser Gln Leu Arg Ile Thr
        65                  70                  75                  80

Ser Leu Gln Leu Ser Asp Thr Gly Gln Tyr Gln Cys Leu Val Phe Leu
                        85                  90                  95

Gly His Gln Thr Phe Val Ser Gln Pro Gly Tyr Val Gly Leu Glu Gly
                        100                 105                 110

Leu Pro Tyr Phe Leu Glu Glu Pro Glu Asp Arg Thr Val Ala Ala Asn
                        115                 120                 125

Thr Pro Phe Asn Leu Ser Cys Gln Ala Gln Gly Pro Pro Glu Pro Val
                        130                 135                 140

Asp Leu Leu Trp Leu Gln Asp Ala Val Pro Leu Ala Thr Ala Pro Gly
        145                 150                 155                 160

His Gly Pro Gln Arg Ser Leu His Val Pro Gly Leu Asn Lys Thr Ser
                        165                 170                 175

Ser Phe Ser Cys Glu Ala His Asn Ala Lys Gly Val Thr Thr Ser Arg
                        180                 185                 190

Thr Ala Thr Ile Thr Val Leu Pro Gln Gln Pro Arg Asn Leu His Leu
                        195                 200                 205
```

```
Val Ser Arg Gln Pro Thr Glu Leu Glu Val Ala Trp Thr Pro Gly Leu
    210                 215                 220
Ser Gly Ile Tyr Pro Leu Thr His Cys Thr Leu Gln Ala Val Leu Ser
225                 230                 235                 240
Asn Asp Gly Met Gly Ile Gln Ala Gly Glu Pro Asp Pro Pro Glu Glu
                245                 250                 255
Pro Leu Thr Ser Gln Ala Ser Val Pro Pro His Gln Leu Arg Leu Gly
            260                 265                 270
Ser Leu His Pro His Thr Pro Tyr His Ile Arg Val Ala Cys Thr Ser
        275                 280                 285
Ser Gln Gly Pro Ser Ser Trp Thr His Trp Leu Pro Val Glu Thr Pro
    290                 295                 300
Glu Gly Val Pro Leu Gly Pro Pro Glu Asn Ile Ser Ala Thr Arg Asn
305                 310                 315                 320
Gly Ser Gln Ala Phe Val His Trp Gln Glu Pro Arg Ala Pro Leu Gln
                325                 330                 335
Gly Thr Leu Leu Gly Tyr Arg Leu Ala Tyr Gln Gly Gln Asp Thr Pro
            340                 345                 350
Glu Val Leu Met Asp Ile Gly Leu Arg Gln Glu Val Thr Leu Glu Leu
        355                 360                 365
Gln Gly Asp Gly Ser Val Ser Asn Leu Thr Val Cys Val Ala Ala Tyr
    370                 375                 380
Thr Ala Ala Gly Asp Gly Pro Trp Ser Leu Pro Val Pro Leu Glu Ala
385                 390                 395                 400
Trp Arg Pro Gly Gln Ala Gln Pro Val His Gln Leu Val Lys Glu Pro
                405                 410                 415
Ser Thr Pro Ala Phe Ser Trp Pro Trp Trp
            420                 425

<210> SEQ ID NO 33
<211> LENGTH: 4
<212> TYPE: PRT
<213> ORGANISM: artificial
<220> FEATURE:
<223> OTHER INFORMATION: Tetrapeptide

<400> SEQUENCE: 33

Gly Phe Leu Gly
1

<210> SEQ ID NO 34
<211> LENGTH: 4
<212> TYPE: PRT
<213> ORGANISM: artificial
<220> FEATURE:
<223> OTHER INFORMATION: Tetrapeptide

<400> SEQUENCE: 34

Ala Leu Ala Leu
1

<210> SEQ ID NO 35
<211> LENGTH: 5
<212> TYPE: PRT
<213> ORGANISM: artificial
<220> FEATURE:
<223> OTHER INFORMATION: Pentapeptide

<400> SEQUENCE: 35
```

```
Pro Val Gly Val Val
1               5
```

ANTIGEN BINDING PROTEIN AND ITS USE AS ADDRESSING PRODUCT FOR THE TREATMENT OF CANCER

CROSS-REFERENCE TO RELATED APPLICATIONS

This application is a continuation-in-part of International Application No. PCT/EP2012/071832, filed Nov. 5, 2012, and claims the priority of European Patent Application No. EP 11306416.6, filed Nov. 3, 2011, the content of all of which is incorporated herein by reference.

The present invention relates to a novel antigen binding protein, in particular a monoclonal antibody, capable of binding specifically to the protein Axl as well as the amino and nucleic acid sequences coding for said protein. From one aspect, the invention relates to a novel antigen binding protein, or antigen binding fragments, capable of binding specifically to Axl and, by inducing internalization of Axl, being internalized into the cell. The invention also comprises the use of said antigen binding protein as an addressing product in conjugation with other anti-cancer compounds, such as toxins, radio-elements or drugs, and the use of same for the treatment of certain cancers. The invention relates more particularly to a novel antibody-drug conjugate for the treatment of cancer.

"Axl" (also referred to as "Ufo", "Ark" or "Tyro7") was cloned from patients with chronic myeloid leukemia as an oncogene triggering the transformation when overexpressed by mouse NIH3T3. It belongs to a family of receptor tyrosine kinases (RTKs) called the TAM (Tyro3, Axl, Mer) family, which includes Tyro3 (Rse, Sky, Dtk, Etk, Brt, Tif), Axl, and Mer (Eyk, Nyk, Tyro-12) [Lemke G. Nat. Rev. Immunol. (2008). 8, 327-336].

The human protein Axl is a 894 amino acids protein which sequence is represented in the sequence listing as SEQ ID NO. 29. Amino acids 1-25 corresponding to the signal peptide, the human protein Axl, without the said peptide signal, is represented in the sequence listing as SEQ ID NO. 30.

Gas6, originally isolated as growth arrest-specific gene, is the common ligand for the members of the TAM family [Varnum B. C. et al. Nature (1995). 373, 623-626]. Gas6 exhibits the highest affinity for Axl, followed by Tyro3 and finally by Mer [Nagata K. et al. J. Biol. Chem. (1996). 271, 30022-30027]. Gas6 consists in a γ-carboxyglutamate (Gla)-rich domain that mediates binding to phospholipid membranes, four epidermal growth factor-like domains, and two laminin G-like (LG) domains [Manfioletti G., Brancolini, C., Avanzi, G. & Schneider, C. Mol. Cell. Biol. (1993). 13, 4976-4985]. As many other RTKs, ligand binding results in receptor dimerization and autophosphorylation of tyrosine residues (tyrosine residues 779, 821 and 866 for the receptor Axl) which serve as docking sites for a variety of intracellular signaling molecules [Linger R. M. Adv. Cancer Res. (2008). 100, 35-83]. Moreover, the Axl receptor can be activated through a ligand-independent process. This activation can occur when the Axl receptor is overexpressed.

Gas6/Axl signaling has been shown to regulate various cellular processes including cell proliferation, adhesion, migration and survival in a large variety of cells in vitro [Hafizi S. & Dahlback, B. FEBS J. (2006). 273, 5231-5244]. In addition, the TAM receptors are involved in the control of innate immunity; they inhibit the inflammatory responses to pathogens in dendritic cells (DCs) and macrophages. They also drive phagocytosis of apoptotic cells by these immune cells and they are required for the maturation and killing activity of natural killer (NK) cells [Lemke G. Nat. Rev. Immunol. (2008). 8, 327-336].

Weakly expressed on normal cells, it is predominantly observed in fibroblasts, myeloid progenitor cells, macrophages, neural tissues, cardiac and skeletal muscle where it supports mainly cell survival. The Gas6/Axl system plays an important role in vascular biology by regulating vascular smooth muscle cell homeostasis [Korshunov V. A., Mohan, A. M., Georger, M. A. & Berk, B. C. Circ. Res. (2006). 98, 1446-1452; Korshunov V. A., Daul, M., Massett, M. P. & Berk, B. C. Hypertension (2007). 50, 1057-1062].

In tumor cells, Axl plays an important role in regulating cellular invasion and migration. Over-expression of Axl is associated not only with poor prognosis but also with increased invasiveness of various human cancers as reported for breast, colon, esophageal carcinoma, hepatocellular, gastric, glioma, lung, melanoma, osteosarcoma, ovarian, prostate, rhabdomyosarcoma, renal, thyroid and uterine endometrial cancer [Linger R. M. Adv. Cancer Res. (2008). 100, 35-83 and Verma A. Mol. Cancer. Ther. (2011). 10, 1763-1773, for reviews]. In breast cancer, Axl appears to be a strong effector of the Epithelial-to-mesenchymal transition (EMT); EMT program contributes actively to migration and dissemination of cancer cells in the organism [Thiery J. P. Curr. Opin. Cell Biol. (2003). 15, 740-746].

Axl has also been shown to regulate angiogenesis. Indeed knockdown of Axl in endothelial cells impaired tube formation and migration [Holland S. J. et al. Cancer Res. (2005). 65, 9294-9303] as well as disturbed specific angiogenic signaling pathways [Li Y. et al. Oncogene (2009). 28, 3442-3455].

More recently several studies on a range of cellular models described the involvement of an Axl overexpression in drug resistance phenomena. The following table 1 summarized these studies.

TABLE 1

| Reference | Cancer type | Therapeutic agent | Cellular model |
| --- | --- | --- | --- |
| Macleod et al., 2005 | Ovarian cancer | Cisplatin | PE01/PE01CDDP |
| Mahadevan et al., 2007 | GIST | Imatinib inhibitor of c-kit/PDGFR | GIST882 > GIST-R |
| Lay et al., 2007 | NSCLC | Doxorubicin | CL-1 clones CL1-5F4 clones |
| Hong et al., 2008 | AML | Doxorubicin/Cisplatin | U937 |
| Liu et al., 2009 | Breast Cancer | Lapatinib (HER1 and HER2 inhibitor) | HER2 (+) BT474 (J4) |
| Keating et al., 2010 | Astrocytoma | Temozolomide Carboplatin Vincristin | G12 A172 |
| Ye et al., 2010 | NSCLC | Erlotinib | HCC827 |

Complete references cited in table 1 above are as follow:
Macleod, K. et al. Cancer Res. (2005). 65, 6789-6800
Mahadevan D. et al. Oncogene (2007). 26, 3909-3919
Lay J. D. et al. Cancer Res. (2007). 67, 3878-3887
Hong C. C. et al. Cancer Lett. (2008). 268, 314-324
Liu L. et al. Cancer Res. (2009). 69, 6871-6878
Keating A. K. et al. Mol. Cancer. Ther. (2010). 9, 1298-1307
Ye X. et al. Oncogene (2010). 29, 5254-5264

In such a context the Axl RTK is considered as an interesting target in oncology. Several groups already developed anti-tumoral strategies targeting the gas6/Axl axis, either using naked monoclonal antibodies or targeted small molecules [Verma A. Mol. Cancer Ther. (2011). 10, 1763-1773].

In a first embodiment, the invention relates to an antigen binding protein, or an antigen binding fragment thereof, which i) specifically binds to the human protein Axl, and ii) is internalized following its binding to said human protein Axl.

More generally, the invention relates to the use of the protein Axl for the selection of an antigen binding protein, or an antigen binding fragment thereof, capable of being internalized following its binding to the said target Axl. More particularly, the said target is the extracellular domain of Axl.

In this particular aspect, the present invention is thus directed to an in vitro method for the screening of a compound, or a binding fragment thereof, capable of delivering or internalizing a molecule of interest into mammalian cells, said molecule of interest being covalently linked to said compound, wherein said method comprises the following steps of:
  a) selecting a compound which is capable of specifically binding the Axl protein, or the extracellular domain (ECD) thereof, or an epitope thereof;
  b) optionally, covalently linking said molecule of interest, or a control molecule, to said compound selected in step a) to form a complex;
  c) contacting said compound selected in step a), or said complex obtained in step b), with a mammal cell, preferably viable cell, expressing at its surface the Axl protein, or a functional fragment thereof;
  d) determining whether said compound, or said molecule of interest or said complex, has been intracellularly delivered or internalized into said mammalian cell; and
  e) selecting said compound as a compound capable of delivering or internalizing a molecule of interest into a viable mammalian cell.

In a preferred embodiment, said compound capable of delivering or internalizing a molecule of interest into a viable mammalian cell is a protein (also designated herein polypeptide or peptide) or a protein-like compound comprising a peptidic structure, particularly an amino-acid sequence of at least 5, 10, 15 or more amino acids residues, said amino-acid residue(s) can be glycosylated.

When said compound capable of delivering or internalizing a molecule of interest into a viable mammalian cell is a protein or a protein-like compound, said compound is also called herein an "antigen binding protein", said antigen binding protein, or binding fragment thereof, can:
  i) specifically binds to the protein Axl, preferably the human Axl protein, and
  ii) is internalized into a mammalian cell following its binding to said protein Axl when said Axl protein is expressed at the surface of said mammalian cell.

In a preferred embodiment, said mammalian viable cell is a human cell, preferably a cell naturally expressing the Axl protein receptor.

In a particular embodiment, the mammalian viable cells in step c) are mammalian cells which express recombinant Axl protein(s) at their surface.

In an also preferred embodiment, said molecule of interest is a cytotoxic molecule (also designated herein as cytoxic or cytostatic agent).

In an also preferred embodiment, said molecule of interest is covalently linked to said compound capable of binding the Axl protein using a linker, more preferably a peptidic linker, more preferably a cleavable peptidic linker, more preferably a linker which can be cleaved by natural intracellular compounds contained in the mammalian cell, particularly in the cytosol of said mammalian cell.

In an also preferred embodiment, said compound capable of binding the Axl protein is an antibody, or functional binding fragment thereof, which is specifically directed against the Axl protein, or against an epitope thereof located into the Axl EDC domain.

The selection step of e) can be realized by any method known by the person skilled in the art for the evaluation of the intracellular delivering or internalization. Assay or test capable of demonstrating or evaluating the presence, absence, or the activity of said compound capable of specifically binding the Axl protein, or of said complex formed by said compound and said molecule of interest, or of said molecule of interest which is covalently linked to said compound, are well known by the skilled person (see some examples of such test or assay disclosed hereinafter, without limiting these tests to these following test examples).

More particularly, these tests or assays can be realized by FACS, Immunofluorescence, flow cytometry, western-blot, cytotoxicity/cytostatic evaluations, etc. . . .

In this aspect, the present invention is also directed to an in vitro method for the preparation of a cytotoxic or cytostatic complex capable of delivering a cytotoxic compound into a mammalian cell, preferably a viable cell, said method comprising the step of:
  covalently linked a cytotoxic agent to a compound which is:
    i) capable of specifically binding the Axl protein, preferably the human Axl protein, and
    ii) is internalized into a mammalian cell following its binding to said protein Axl when said Axl protein is expressed at the surface of said mammalian cell.

In a preferred embodiment, in said in vitro method for the preparation of a cytotoxic or cytostatic complex, said antigen binding capable of specifically binding the Axl protein and internalized into a mammalian cell following its binding to said protein Axl when said Axl protein is expressed at the surface of said mammalian cell, is an antigen binding protein selected by an in vitro method for the screening of a compound, or a binding fragment thereof, capable of delivering or internalizing a molecule of interest into mammalian cells according to the present invention.

Preferably said compound is a protein-like protein, more preferably an antibody which is specifically directed against the Axl protein, or against an epitope thereof located into the Axl EDC domain, or a functional binding fragment of said antibody.

In preferred embodiment, said cytotoxic agent is covalently linked to the said anti-Axl antibody or functional fragment thereof, using a linker, more preferably a peptidic linker, more preferably a cleavable peptidic linker, more preferably a linker which can be cleaved, as non limitative example by natural intracellular compounds.

Like the other members of the TAM family, the Axl extracellular domain (ECD) has an organization closed to those of cell adhesion molecules. Axl ECD is characterized by a combination of two immunoglobulin-like domains followed by two adjacent fibronectin type III-like domains [O'Bryan J. P. et al. Mol. Cell. Biol. (1991). 11, 5016-5031]. The two N-terminal immunoglobulin-like domains are sufficient for Gas6 ligand binding [Sasaki T. et al. EMBO J. (2006). 25, 80-87].

The ECD of the human protein Axl is a 451 amino acids fragment, corresponding to amino acids 1-451 of the sequence SEQ ID NO. 29, which sequence is represented in the sequence listing as SEQ ID NO. 31. Amino acids 1-25 corresponding to the signal peptide, the ECD of the human protein Axl without the signal peptide corresponds to the amino acids 26-451 of the sequence SEQ ID NO.29, represented by the sequence SEQ ID NO. 32.

To date different modes of internalization have been identified. They orientate the becoming the internalized proteins or proteic complex in the cell. After endocytosis, most membranes proteins or lipids returns to the cell surface (recycling), but some membrane components are delivered to late endosomes or the Golgi [Maxfield F. R. & McGraw, T. E. Nat. Rev. Mol. Cell. Biol. (2004). 5, 121-132].

In a preferred embodiment, the invention relates to an antigen binding protein, or an antigen binding fragment thereof, which i) specifically binds to the human protein Axl, and ii) is internalized following its binding to said human protein Axl, said antigen binding protein comprising at least an amino acid sequence selected from the group consisting of SEQ ID NOs. 1 to 14, or any sequence exhibiting at least 80%, preferably 85%, 90%, 95% and 98% identity with SEQ ID NOs. 1 to 14.

In a most preferred embodiment, the invention relates to an antigen binding protein, or an antigen binding fragment thereof, which
i) specifically binds to the human protein Axl, preferably having the sequence SEQ ID NO. 29 or 30 or natural variant sequence thereof, and
ii) is internalized following its binding to said human protein Axl,
said antigen binding protein comprising at least an amino acid sequence selected from the group consisting of SEQ ID NOs. 1 to 14.

A "binding protein" or "antigen binding protein" is a peptidic chain having a specific or general affinity with another protein or molecule (generally referred as antigen). Proteins are brought into contact and form a complex when binding is possible. The antigen binding protein of the invention can preferably be, without limitation, an antibody, a fragment or derivative of an antibody, a protein or a peptide.

By "antigen binding fragment" of an antigen binding protein according to the invention, it is intended to indicate any peptide, polypeptide, or protein retaining the ability to specifically bind to the target (also generally referred as antigen) of the antigen binding protein and comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of the antigen binding protein.

In a preferred embodiment wherein the antigen binding protein is an antibody, such "antigen binding fragments" are selected in the group consisting of Fv, scFv (sc for single chain), Fab, F(ab')$_2$, Fab', scFv-Fc fragments or diabodies, or any fragment of which the half-life time would have been increased by chemical modification, such as the addition of poly(alkylene) glycol such as poly(ethylene) glycol ("PEGylation") (pegylated fragments called Fv-PEG, scFv-PEG, Fab-PEG, F(ab')$_2$-PEG or Fab'-PEG) ("PEG" for Poly(Ethylene) Glycol), or by incorporation in a liposome, said fragments having at least one of the characteristic CDRs of the antibody according to the invention. Preferably, said "antigen binding fragments" will be constituted or will comprise a partial sequence of the heavy or light variable chain of the antibody from which they are derived, said partial sequence being sufficient to retain the same specificity of binding as the antibody from which it is descended and a sufficient affinity, preferably at least equal to 1/100, in a more preferred manner to at least 1/10, of the affinity of the antibody from which it is descended, with respect to the target. Such a functional fragment will contain at the minimum 5 amino acids, preferably 10, 15, 25, 50 and 100 consecutive amino acids of the sequence of the antibody from which it is descended.

The term "epitope" is a region of an antigen that is bound by an antigen binding protein, including antibodies. Epitopes may be defined as structural or functional. Functional epitopes are generally a subset of the structural epitopes and have those residues that directly contribute to the affinity of the interaction. Epitopes may also be conformational, that is, composed of non-linear amino acids. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics.

In the present application, the epitope is localized into the extracellular domain of the human protein Axl.

According to a preferred embodiment of the invention, the antigen binding protein, or an antigen binding fragment thereof, specifically binds to an epitope localized into the human protein Axl extracellular domain, preferably having the sequence SEQ ID NO. 31 or 32 or natural variant sequence thereof.

By "specifically binding", "specifically binds", or the like, it is intended that the antigen binding protein, or antigen-binding fragment thereof, forms a complex with an antigen that is relatively stable under physiologic conditions. Specific binding can be characterized by an equilibrium dissociation constant of at least about $1.10^{-6}$ M or less. Methods for determining whether two molecules specifically bind are well known in the art and include, for example, equilibrium dialysis, surface plasmon resonance, and the like. For the avoidance of doubt, it does not mean that the said antigen binding fragment could not bind or interfere, at a low level, to another antigen. Nevertheless, as a preferred embodiment, the said antigen binding fragment binds only to the said antigen.

In this sense, "$EC_{50}$" refers to 50% effective concentration. More precisely the term half maximal effective concentration ($EC_{50}$) corresponds to the concentration of a drug, antibody or toxicant which induces a response halfway between the baseline and maximum after some specified exposure time. It is commonly used as a measure of drug's potency. The $EC_{50}$ of a graded dose response curve therefore represents the concentration of a compound where 50% of its maximal effect is observed. The $EC_{50}$ of a quantal dose response curve represents the concentration of a compound where 50% of the population exhibits a response, after specified exposure duration. Concentration measures typically follow a sigmoidal curve, increasing rapidly over a relatively small change in concentration. This can be determined mathematically by derivation of the best-fit line.

As a preferred embodiment, the $EC_{50}$, determined in the present invention characterized the potency of antibody binding on the Axl ECD exposed on human tumor cells. The $EC_{50}$ parameter is determined using FACS analysis. The $EC_{50}$ parameter reflects the antibody concentration for which 50% of the maximal binding on the human Axl expressed on human tumor cells is obtained. Each $EC_{50}$ value was calculated as the midpoint of the dose response curve using a four-parameter regression curve fitting program (Prism Software). This parameter has been selected as to be representative of physiological/pathological conditions.

In an embodiment of the invention, the antigen binding protein, or an antigen binding fragment thereof, binds to its epitope with an $EC_{50}$ of at least $10^{-9}$ M, preferentially between $10^{-9}$ and $10^{-12}$ M.

Another embodiment of the invention is a process or method for the selection of an antigen binding protein, or an antigen binding fragment thereof, capable of being intracellularly internalizing into a mammalian cell, preferably into a human cell, preferably a viable cell, comprising the steps of:

i) selecting antigen binding protein which specifically binds to Axl, preferably to its EDC domain or to an epitope thereof; and ii) selecting said antigen binding protein from previous step i) which is internalized into a mammalian cell following their binding to an Axl protein expressed at the surface of said mammalian cell.

In a particular embodiment, said mammalian cell naturally expresses the Axl protein receptor at their surface or are mammalian cells which express recombinant Axl protein at their surface, preferably human cells.

Such method or process can comprise the steps of i) selecting antigen binding protein which specifically bind to Axl with an $EC^{50}$ of at least $10^{-9}$ M and ii) selecting antigen binding protein from previous step which are internalized following their binding to Axl. The selection step of ii) can be realized by any method known by the person skilled in the art for the evaluation of the internalization. More particularly, tests can be realized by FACS, Immunofluorescence, flow cytometry, western-blot, cytotoxicity evaluations, etc. . . .

Another characteristic of the antigen binding protein according to the invention is that it does not have any significant activity on the proliferation of tumor cells. More particularly, as illustrated in the following examples, the antigen binding protein according to the invention does not have any significant in vitro activity on the proliferation SN12C model.

In oncology, there are multiple mechanisms by which mAbs can exert therapeutic efficacy, but often their activity is not sufficient to produce a lasting benefit. Hence several strategies have been employed to enhance their activity particularly by combining them with drugs as chemotherapeutic agents. As an efficient alternative to combination protocols, immunotoxins become a novel therapeutic option for treating cancer [Beck A. et al. Discov. Med. (2010). 10, 329-339; Alley S. C. et al. J. Pharmacol. Exp. Ther. (2009). 330, 932-938]. Antibody-drug conjugates (ADCs) represent one approach where the ability to harness mAbs specificity and target the delivery of a cytotoxic agent to the tumor may significantly enhance both mAbs and drug activities. Ideally the mAb will specifically bind to an antigen with substantial expression on tumor cells but limited expression on normal cells.

In the present description or figures the terms "Axl antibody" and "anti-Axl antibody" have the same meaning and designate antibodies directed against Axl and/or capable of binding specifically the Axl protein.

The present invention focused on a specific anti-Axl binding protein, and more particularly on a specific anti-Axl antibody, presenting a high ability to be internalized following Axl binding. Such antigen binding protein is interesting as one of the immuno-drug-conjugate components, so it addresses the linked cytotoxic into the targeted cancer cells. Once internalized the cytotoxic triggers cancer cell death.

Important keys to success with immunoconjugate therapy are thought to be the target antigen specificity and the internalization of the antigen-binding protein complexes into the cancer cells. Obviously non-internalizing antigens are less effective than internalizing antigens to delivers cytotoxic agents. Internalization processes are variable across antigens and depend on multiple parameters that can be influenced by binding proteins. Cell-surface RTKs constitute an interesting antigens family to investigate for such an approach.

In the biomolecule, the cytotoxic brings the cytotoxic activity and the used antigen binding protein brings its specificity against cancer cells, as well as a vector for entering within the cells to correctly address the cytotoxic.

Thus to improve the immunoconjugate molecule, the carrier-binding protein must exhibit high ability to internalize into the targeted cancer cells. The efficiency with which the binding proteins mediated internalisation differs significantly depending on the epitope targeted. Selection of potent internalizing Axl binding proteins requires various experimental data studying not only Axl downregulation but also following Axl binding proteins becoming into the cells.

In a preferred embodiment, the internalization of the antigen binding protein according to the invention can be evaluated preferably by immunofluorescence (as exemplified hereinafter in the present application) or any method or process known by the person skilled in the art specific for the internalization mechanism.

In another preferred embodiment, as the complex Axl-antigen binding protein, according to the invention, is internalized after the binding of the binding protein of the invention to the ECD of said Axl, a reduction in the quantity of Axl at the surface of the cells is induced. This reduction can be quantified by any method known by the person skilled in the art (western-blot, FACS, immunofluorescence, etc. . . . ).

In an embodiment of the invention, this reduction, thus reflecting the internalization, can be preferably measured by FACS and expressed as the difference or delta between the Mean Fluorescence Intensity (MFI) measured on untreated cells with the MFI measured with cells treated with the antigen binding protein according to the invention.

As non limitative example of the present invention, this delta is determined based on MFIs obtained with untreated cells and cells treated with the antigen binding protein of the invention as described in example 9 using i) human renal tumor SN12C cells after a 24 hour incubation period with the antigen binding protein of the invention and ii) a secondary antibody labelled with Alexa488. This parameter is defined as calculated with the following formula:

$$\Delta(MFI_{24h}\text{ untreated cells} - MFI_{24h}\text{ antigen binding protein treated cells})$$

This difference between MFIs reflects the Axl downregulation as MFIs are proportional of Axl expressed on the cell-surface.

In a more preferred and advantageous aspect, the antigen binding protein, or an antigen binding fragment thereof, of the invention consists of a monoclonal antibody, preferably an isolated Mab, triggering a Δ (MFI$_{24h}$ untreated cells–MFI$_{24h}$ treated cells) of at least 200, preferably of at least 300.

The antigen binding protein, or an antigen binding fragment thereof, according to the invention, induces a reduction of MFI of at least 200.

In more details, the above mentioned delta can be measured according to the following process, which must be considered as an illustrative and non limitative example:

a) Treating and incubating tumoral cells of interest with the antigen binding protein of the invention;
b) Treating the treated cells of step a) and, in parallel, untreated cells with the antigen binding protein of the invention,
c) Measuring the MFI (representative of the quantity of Axl present at the surface) for the treated and the non treated cells with a secondary labeled antibody capable of binding to the antigen binding protein, and
d) Calculating the delta as the subtraction of the MFI obtained with the treated cells from the MFI obtained with the non treated cells.

The terms "antibody", "antibodies" or "immunoglobulin" are used interchangeably in the broadest sense and include monoclonal antibodies, preferably isolated Mab, (e.g., full length or intact monoclonal antibodies), polyclonal antibodies, multivalent antibodies or multispecific antibodies (e.g., bispecific antibodies so long as they exhibit the desired biological activity).

More particularly, such molecule consists of a glycoprotein comprising at least two heavy (H) chains and two light (L) chains inter-connected by disulfide bonds. Each heavy chain comprises a heavy chain variable region (or domain) (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g. effector cells) and the first component (Clq) of the classical complement system.

Antibodies in the sense of the invention also include certain antibody fragments, thereof. The said antibody fragments exhibit the desired binding specificity and affinity, regardless of the source or immunoglobulin type (i.e., IgG, IgE, IgM, IgA, etc.), i.e., they are capable of binding specifically the Axl protein with an affinity comparable to the full-length antibodies of the invention.

In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988) or to the technique of preparation from hybridomas described by Kohler and Milstein (Nature, 256:495-497, 1975).

The term "monoclonal antibody" or "Mab" as used herein refers to an antibody molecule that is directed against a specific antigen and which may be produced by a single clone of B cells or hybridoma. Monoclonal antibodies may also be recombinant, i.e. produced by protein engineering. In addition, in contrast with preparations of polyclonal antibodies which typically include various antibodies directed against various determinants, or epitopes, each monoclonal antibody is directed against a single epitope of the antigen. The invention relates to antibodies isolated or obtained by purification from natural sources or obtained by genetic recombination or chemical synthesis.

An embodiment of the invention is an antigen binding protein, or an antigen binding fragment thereof, comprising or consisting of an antibody selected in the group consisting of 1A4, 11D12, 320G10, 427B7, 517F1, 530C8, 534G9, 535F7, 547A1, 1023F10, 1613F12 or 1614G5.

A preferred embodiment of the invention is an antigen binding protein, or an antigen binding fragment thereof, comprising or consisting of an antibody, said antibody comprising the three light chain CDRs comprising the sequences SEQ ID NOs. 1, 2 and 3, or any sequence exhibiting at least 80%, preferably 85%, 90%, 95% and 98% identity with SEQ ID NOs. 1, 2 and 3; and the three heavy chain CDRs comprising the sequences SEQ ID NOs. 4, 5 and 6, or any sequence exhibiting at least 80%, preferably 85%, 90%, 95% and 98% identity with SEQ ID NOs. 4, 5 and 6.

In a more preferred embodiment of the invention, the antigen binding protein, or an antigen binding fragment thereof, consists of an antibody, said antibody comprising the three light chain CDRs comprising the sequences SEQ ID NOs. 1, 2 and 3; and the three heavy chain CDRs comprising the sequences SEQ ID NOs. 4, 5 and 6.

In a preferred aspect, by CDR regions or CDR(s), it is intended to indicate the hypervariable regions of the heavy and light chains of the immunoglobulins as defined by IMGT. Without any contradictory mention, the CDRs will be defined in the present specification according to the IMGT numbering system.

The IMGT unique numbering has been defined to compare the variable domains whatever the antigen receptor, the chain type, or the species [Lefranc M.-P., Immunology Today 18, 509 (1997)/Lefranc M.-P., The Immunologist, 7, 132-136 (1999)/Lefranc, M.-P., Pommié, C., Ruiz, M., Giudicelli, V., Foulquier, E., Truong, L., Thouvenin-Contet, V. and Lefranc, Dev. Comp. Immunol., 27, 55-77 (2003)]. In the IMGT unique numbering, the conserved amino acids always have the same position, for instance cystein 23 (1st-CYS), tryptophan 41 (CONSERVED-TRP), hydrophobic amino acid 89, cystein 104 (2nd-CYS), phenylalanine or tryptophan 118 (J-PHE or J-TRP). The IMGT unique numbering provides a standardized delimitation of the framework regions (FR1-IMGT: positions 1 to 26, FR2-IMGT: 39 to 55, FR3-IMGT: 66 to 104 and FR4-IMGT: 118 to 128) and of the complementarity determining regions: CDR1-IMGT: 27 to 38, CDR2-IMGT: 56 to 65 and CDR3-IMGT: 105 to 117. As gaps represent unoccupied positions, the CDR-IMGT lengths (shown between brackets and separated by dots, e.g. [8.8.13]) become crucial information. The IMGT unique numbering is used in 2D graphical representations, designated as IMGT Colliers de Perles [Ruiz, M. and Lefranc, M.-P., Immunogenetics, 53, 857-883 (2002)/Kaas, Q. and Lefranc, M.-P., Current Bioinformatics, 2, 21-30 (2007)], and in 3D structures in IMGT/3Dstructure-DB [Kaas, Q., Ruiz, M. and Lefranc, M.-P., T cell receptor and MHC structural data. Nucl. Acids. Res., 32, D208-D210 (2004)].

It must be understood that, without contradictory specification in the present specification, complementarity-determining regions or CDRs, mean the hypervariable regions of the heavy and light chains of immunoglobulins as defined according to the IMGT numbering system.

Nevertheless, CDRs can also be defined according to the Kabat numbering system (Kabat et al., Sequences of proteins of immunological interest, 5$^{th}$ Ed., U.S. Department of Health and Human Services, NIH, 1991, and later editions). There are three heavy-chain CDRs and three light-chain CDRs. Here, the terms "CDR" and "CDRs" are used to indicate, depending on the case, one or more, or even all, of the regions containing the majority of the amino acid residues responsible for the antibody's binding affinity for the antigen or epitope it recognizes.

According to the Kabat numbering system, the present invention relates to an antigen binding protein, or an antigen binding fragment thereof, consisting of an antibody, said antibody comprising the three light chain CDRs, as defined according to Kabat numbering system, comprising the sequences SEQ ID NOs. 9, 10 and 11, or any sequence exhibiting at least 80%, preferably 85%, 90%, 95% and 98% identity with SEQ ID NOs. 9, 10 and 11; and the three heavy chain CDRs, as defined according to Kabat numbering system, comprising the sequences SEQ ID NOs. 12, 13 and 14, or any sequence exhibiting at least 80%, preferably 85%, 90%, 95% and 98% identity with SEQ ID NOs. 12, 13 and 14.

In the sense of the present invention, the "percentage identity" between two sequences of nucleic acids or amino acids means the percentage of identical nucleotides or amino acid residues between the two sequences to be compared, obtained after optimal alignment, this percentage being purely statistical and the differences between the two sequences being distributed randomly along their length. The comparison of two nucleic acid or amino acid sequences is traditionally carried out by comparing the sequences after having optimally aligned them, said comparison being able to be conducted by segment or by using an "alignment window". Optimal alignment of the sequences for comparison can be carried out, in addition to comparison by hand, by means of the local homology algorithm of Smith and Waterman (1981) [Ad. App. Math. 2:482], by means of the local homology algorithm of Neddleman and Wunsch (1970) [J. Mol. Biol. 48:443], by means of the similarity search method of Pearson and Lipman (1988) [Proc. Natl. Acad. Sci. USA 85:2444] or by means of computer software using these algorithms (GAP, BESTFIT, FASTA and TFASTA in the Wisconsin Genetics Software Package, Genetics Computer Group, 575 Science Dr., Madison, Wis., or by the comparison software BLAST NR or BLAST P).

The percentage identity between two nucleic acid or amino acid sequences is determined by comparing the two optimally-aligned sequences in which the nucleic acid or amino acid sequence to compare can have additions or deletions compared to the reference sequence for optimal alignment between the two sequences. Percentage identity is calculated by determining the number of positions at which the amino acid nucleotide or residue is identical between the two sequences, preferably between the two complete sequences, dividing the number of identical positions by the total number of positions in the alignment window and multiplying the result by 100 to obtain the percentage identity between the two sequences.

For example, the BLAST program, "BLAST 2 sequences" (Tatusova et al., "Blast 2 sequences—a new tool for comparing protein and nucleotide sequences", FEMS Microbiol., 1999, Lett. 174:247-250) available on the site http://www.ncbi.nlm.nih.gov/gorf/b12.html, can be used with the default parameters (notably for the parameters "open gap penalty": 5, and "extension gap penalty": 2; the selected matrix being for example the "BLOSUM 62" matrix proposed by the program); the percentage identity between the two sequences to compare is calculated directly by the program.

For the amino acid sequence exhibiting at least 80%, preferably 85%, 90%, 95% and 98% identity with a reference amino acid sequence, preferred examples include those containing the reference sequence, certain modifications, notably a deletion, addition or substitution of at least one amino acid, truncation or extension. In the case of substitution of one or more consecutive or non-consecutive amino acids, substitutions are preferred in which the substituted amino acids are replaced by "equivalent" amino acids. Here, the expression "equivalent amino acids" is meant to indicate any amino acids likely to be substituted for one of the structural amino acids without however modifying the biological activities of the corresponding antibodies and of those specific examples defined below.

Equivalent amino acids can be determined either on their structural homology with the amino acids for which they are substituted or on the results of comparative tests of biological activity between the various antigen binding proteins likely to be generated.

As a non-limiting example, table 2 below summarizes the possible substitutions likely to be carried out without resulting in a significant modification of the biological activity of the corresponding modified antigen binding protein; inverse substitutions are naturally possible under the same conditions.

TABLE 2

| Original residue | Substitution(s) |
| --- | --- |
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (E) | Asp |
| Gly (G) | Ala |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

An embodiment of the invention relates to an antigen binding protein, or an antigen binding fragment thereof, comprising the three light chain CDRs comprising the sequences SEQ ID NOs. 1, 2 and 3, or any sequence exhibiting at least 80%, preferably 85%, 90%, 95% and 98% identity with SEQ ID NOs.1, 2 and 3; and a heavy chain variable domain of sequence SEQ ID NO. 8, or any sequence exhibiting at least 80%, preferably 85%, 90%, 95% and 98% identity with SEQ ID NO. 8.

According to a preferred embodiment of the invention, the antigen binding protein, or an antigen binding fragment thereof comprises the three light chain CDRs comprising the sequences SEQ ID NOs. 1, 2 and 3; and a heavy chain variable domain of sequence SEQ ID NO. 8, or any sequence exhibiting at least 80% identity with SEQ ID NO.8.

According to another preferred embodiment of the invention, the antigen binding protein, or an antigen binding fragment thereof comprises a heavy chain variable domain of sequence SEQ ID NO. 8, or any sequence exhibiting at least 80% identity with SEQ ID NO.8.

By "any sequence exhibiting at least 80% identity with SEQ ID NO. 8", its is intended to designate the sequence exhibiting the three heavy chain CDRs SEQ ID NOs. 4, 5 and 6 and, in addition, exhibiting at least 80% identity with the full sequence SEQ ID NO. 8 outside the sequences corresponding to the CDRs, i.e. SEQ ID NOs. 4, 5 and 6.

Another embodiment of the invention relates to an antigen binding protein, or an antigen binding fragment thereof, comprising a light chain variable domain of sequence SEQ ID NO. 7, or any sequence exhibiting at least 80%, preferably 85%, 90%, 95% and 98% identity with SEQ ID NO. 7; and the three heavy chain CDRs comprising the sequences SEQ ID NOs. 4, 5 and 6, or any sequence exhibiting at least 80%, preferably 85%, 90%, 95% and 98% identity with SEQ ID NOs. 4, 5 and 6.

According to a preferred embodiment of the invention, the antigen binding protein, or an antigen binding fragment thereof, comprises a light chain variable domain of sequence SEQ ID NO. 7, or any sequence exhibiting at least 80% identity with SEQ ID NO.7; and the three heavy chain CDRs comprising the sequences SEQ ID NOs. 4, 5 and 6.

According to another preferred embodiment of the invention, the antigen binding protein, or an antigen binding fragment thereof, comprises a light chain variable domain of sequence SEQ ID NO. 7, or any sequence exhibiting at least 80% identity with SEQ ID NO.7.

By "any sequence exhibiting at least 80% identity with SEQ ID NO. 7", its is also intended to designate the sequence exhibiting the three light chain CDRs SEQ ID NOs. 1, 2 and 3 and, in addition, exhibiting at least 80% identity with the full sequence SEQ ID NO. 7 outside the sequences corresponding to the CDRs, i.e. SEQ ID NOs. 1, 2 and 3.

Another embodiment of the invention relates to an antigen binding protein, or an antigen binding fragment thereof, comprising a light chain variable domain of sequence SEQ ID NO. 7, or any sequence exhibiting at least 80%, preferably 85%, 90%, 95% and 98% identity with SEQ ID NO. 7; and a heavy chain variable domain of sequence SEQ ID NO. 8, or any sequence exhibiting at least 80%, preferably 85%, 90%, 95% and 98% identity with SEQ ID NO. 8.

According to a preferred embodiment of the invention, the antigen binding protein, or an antigen binding fragment thereof, comprises a light chain variable domain of sequence SEQ ID NO. 7, or any sequence exhibiting at least 80% identity with SEQ ID NO. 7 and a heavy chain variable domain of sequence SEQ ID NO. 8, or any sequence exhibiting at least 80% identity with SEQ ID NO. 8.

For more clarity, table 3 below summarizes the various amino acid sequences corresponding to the antigen binding protein of the invention (with Mu.=murine).

TABLE 3

| | CDR numbering | Heavy chain | Light chain | SEQ ID NO. |
|---|---|---|---|---|
| 1613F12 | IMGT | | CDR-L1 | 1 |
| | | | CDR-L2 | 2 |
| | | | CDR-L3 | 3 |
| | | CDR-H1 | | 4 |
| | | CDR-H2 | | 5 |
| | | CDR-H3 | | 6 |
| | Kabat | | CDR-L1 | 9 |
| | | | CDR-L2 | 10 |
| | | | CDR-L3 | 11 |
| | | CDR-H1 | | 12 |
| | | CDR-H2 | | 13 |
| | | CDR-H3 | | 14 |
| | | | Mu. variable domain | 7 |
| | | Mu. variable domain | | 8 |

A specific aspect of the present invention relates to a murine antibody, or its derived compounds or antigen binding fragments, characterized in that said antibody also comprises light-chain and heavy-chain constant regions derived from an antibody of a species heterologous with the mouse, notably man.

Another specific aspect of the present invention relates to a chimeric antibody, or its derived compounds or antigen binding fragments, characterized in that said antibody also comprises light-chain and heavy-chain constant regions derived from an antibody of a species heterologous with the mouse, notably human.

Yet another specific aspect of the present invention relates to a humanized antibody, or its derived compounds or antigen binding fragments, characterized in that the constant regions of the light-chain and the heavy-chain derived from human antibody are, respectively, the lambda or kappa region and the gamma-1, gamma-2 or gamma-4 region.

Another aspect of the invention is an antigen binding protein consisting of the monoclonal antibody 1613F12 derived from the hybridoma I-4505 deposited at the CNCM, Institut Pasteur, France, on the 28 Jul. 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Jul. 28, 2011, under number I-4505. Said hybridoma was obtained by the fusion of Balb/C immunized mice splenocytes/lymphocytes and cells of the myeloma Sp 2/O-Ag 14 cell line.

According to another aspect, the invention relates to a murine hybridoma capable of secreting an antibody comprising the three light chain CDRs comprising the sequences SEQ ID NOs. 1, 2 and 3; and the three heavy chain CDRs comprising the sequences SEQ ID NOs. 4, 5 and 6, said hybridoma being filed at the CNCM, Pasteur Institute, Paris, France, on Jul. 28, 2011, under number I-4505. Said hybridoma was obtained by the fusion of Balb/C immunized mice splenocytes/lymphocytes and cells of the myeloma Sp 2/O-Ag 14 cell line.

An object of the invention is the murine hybridoma I-4505 deposited at the CNCM, Institut Pasteur, France, on the 28 Jul. 2011.

Another aspect of the invention is an antigen binding protein consisting of the monoclonal antibody 1A4 derived from the hybridoma I-3947 deposited at the CNCM, Institut Pasteur, France, on Mar. 12, 2008, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Mar. 12, 2008, under number I-3947. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 11D12 derived from the hybridoma I-4116 deposited at the CNCM, Institut Pasteur, France, on Jan. 27, 2009, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Jan. 27, 2009, under number I-4116. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 320G10 derived from the hybridoma I-4514 deposited at the CNCM, Institut Pasteur, France, on Sep. 15, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Sep. 15, 2011, under number I-4514. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 427B7 derived from the hybridoma I-4518 deposited at the CNCM, Institut Pasteur, France, on Sep. 15, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Sep. 15, 2011, under number I-4518. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 517F1 derived from the hybridoma I-4502 deposited at the CNCM, Institut Pasteur, France, on Jul. 28, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Jul. 28, 2011, under number I-4502. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 530C8 derived from the hybridoma I-4728 deposited at the CNCM, Institut Pasteur, France, on Apr. 4, 2013, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Apr. 4, 2013, under number I-4728. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 534G9 derived from the hybridoma I-4729 deposited at the CNCM, Institut Pasteur, France, on Apr. 4, 2013, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Apr. 4, 2013, under number I-4729. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 535F7 derived from the hybridoma I-4510 deposited at the CNCM, Institut Pasteur, France, on Jul. 28, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Jul. 28, 2011, under number I-4510. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 547A1 derived from the hybridoma I-4506 deposited at the CNCM, Institut Pasteur, France, on Jul. 28, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Jul. 28, 2011, under number I-4506. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 1023F10 derived from the hybridoma I-4507 deposited at the CNCM, Institut Pasteur, France, on Jul. 28, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Jul. 28, 2011, under number I-4507. Said hybridoma was obtained by the fusion of Balb/C immunized mice splenocytes/lymphocytes and cells of the myeloma Sp 2/O-Ag 14 cell line.

Another aspect of the invention is an antigen binding protein consisting of the monoclonal antibody 1614G5 derived from the hybridoma I-4519 deposited at the CNCM, Institut Pasteur, France, on Sep. 15, 2011, or an antigen binding fragment thereof.

According to another aspect, the invention relates to a murine hybridoma capable of secreting an antigen binding protein according to the invention, notably the hybridoma of murine origin filed with the French collection for microorganism cultures (CNCM, Pasteur Institute, Paris, France) on Sep. 15, 2011, under number I-4519. Said hybridoma was obtained by the fusion of Balb/C immunized mice splenocytes/lymphocytes and cells of the myeloma Sp 2/O-Ag 14 cell line.

The antigen binding protein of the invention also comprises chimeric or humanized antibodies.

A chimeric antibody is one containing a natural variable region (light chain and heavy chain) derived from an antibody of a given species in combination with constant regions of the light chain and the heavy chain of an antibody of a species heterologous to said given species.

The antibodies, or chimeric fragments of same, can be prepared by using the techniques of recombinant genetics. For example, the chimeric antibody could be produced by cloning recombinant DNA containing a promoter and a sequence coding for the variable region of a nonhuman monoclonal antibody of the invention, notably murine, and a sequence coding for the human antibody constant region. A chimeric antibody according to the invention coded by one such recombinant gene could be, for example, a mouse-human chimera, the specificity of this antibody being determined by the variable region derived from the murine DNA and its isotype determined by the constant region derived from human DNA. Refer to Verhoeyn et al. (BioEssays, 8:74, 1988) for methods for preparing chimeric antibodies.

In another aspect, the invention describes a binding protein which consists of a chimeric antibody.

In a particular preferred embodiment, the chimeric antibody, or an antigen binding fragment of same, of the invention comprises a light chain variable domain sequence comprising the amino acid sequence SEQ ID NO. 7, and in that it comprises a heavy chain variable domain sequence comprising the amino acid sequence SEQ ID NO. 8.

In another aspect, the invention describes a binding protein which consists of a humanized antibody.

"Humanized antibodies" means an antibody that contains CDR regions derived from an antibody of nonhuman origin, the other parts of the antibody molecule being derived from one (or several) human antibodies. In addition, some of the skeleton segment residues (called FR) can be modified to preserve binding affinity (Jones et al., Nature, 321:522-525, 1986; Verhoeyen et al., Science, 239:1534-1536, 1988; Riechmann et al., Nature, 332:323-327, 1988).

The humanized antibodies of the invention or fragments of same can be prepared by techniques known to a person skilled in the art (such as, for example, those described in the documents Singer et al., J. Immun, 150:2844-2857, 1992; Mountain et al., Biotechnol. Genet. Eng. Rev., 10:1-142, 1992; and Bebbington et al., Bio/Technology, 10:169-175, 1992). Such humanized antibodies are preferred for their use in methods involving in vitro diagnoses or preventive and/or therapeutic treatment in vivo. Other humanization techniques, also known to a person skilled in the art, such as, for example, the "CDR grafting" technique described by PDL in patents EP 0 451 261, EP 0 682 040, EP 0 939 127, EP 0 566 647 or U.S. Pat. No. 5,530,101, U.S. Pat. No. 6,180,370, U.S. Pat. No. 5,585,089 and U.S. Pat. No. 5,693,761. U.S. Pat. Nos. 5,639, 641 or 6,054,297, 5,886,152 and 5,877,293 can also be cited.

In addition, the invention also relates to humanized antibodies arising from the murine antibodies described above.

In a preferred manner, constant regions of the light-chain and the heavy-chain derived from human antibody are, respectively, the lambda or kappa and the gamma-1, gamma-2 or gamma-4 region.

A novel aspect of the present invention relates to an isolated nucleic acid characterized in that it is selected among the following nucleic acids (including any degenerate genetic code):

a) a nucleic acid coding for an antigen binding protein, or for an antigen binding fragment of same, according to the invention;

b) a nucleic acid comprising:
a nucleic acid sequence selected from the group consisting of SEQ ID NOs. 15 to 28, or
a nucleic acid sequence comprising the 6 nucleic acid sequences SEQ ID NOs.: 15 to 20, or
a nucleic acid sequence comprising the two nucleic acid sequences SEQ ID NOs.: 21, 22;

c) a nucleic acid complementary to a nucleic acid as defined in a) or b); and d) a nucleic acid, preferably having at least 18 nucleotides, capable of hybridizing under highly stringent conditions with a nucleic acid sequence as defined in part a) or b), or with a sequence with at least 80%, preferably 85%, 90%, 95% and 98% identity after optimal alignment with a nucleic acid sequence as defined in part a) or b).

Table 4 below summarizes the various nucleotide sequences concerning the binding protein of the invention (with Mu.=Murine).

TABLE 4

| | CDR numbering | Heavy chain | Light chain | SEQ ID NO. |
|---|---|---|---|---|
| 1613F12 | IMGT | | CDR-L1 | 15 |
| | | | CDR-L2 | 16 |
| | | | CDR-L3 | 17 |
| | | CDR-H1 | | 18 |
| | | CDR-H2 | | 19 |
| | | CDR-H3 | | 20 |
| | Kabat | | CDR-L1 | 23 |
| | | | CDR-L2 | 24 |
| | | | CDR-L3 | 25 |
| | | CDR-H1 | | 26 |
| | | CDR-H2 | | 27 |
| | | CDR-H3 | | 28 |
| | | | Mu. variable domain | 21 |
| | | Mu. variable domain | | 22 |

The terms "nucleic acid", "nucleic sequence", "nucleic acid sequence", "polynucleotide", "oligonucleotide", "polynucleotide sequence" and "nucleotide sequence", used interchangeably in the present description, mean a precise sequence of nucleotides, modified or not, defining a fragment or a region of a nucleic acid, containing unnatural nucleotides or not, and being either a double-strand DNA, a single-strand DNA or transcription products of said DNAs.

The sequences of the present invention have been isolated and/or purified, i.e., they were sampled directly or indirectly, for example by a copy, their environment having been at least partially modified. Isolated nucleic acids obtained by recombinant genetics, by means, for example, of host cells, or obtained by chemical synthesis should also be mentioned here.

"Nucleic sequences exhibiting a percentage identity of at least 80%, preferably 85%, 90%, 95% and 98%, after optimal alignment with a preferred sequence" means nucleic sequences exhibiting, with respect to the reference nucleic sequence, certain modifications such as, in particular, a deletion, a truncation, an extension, a chimeric fusion and/or a substitution, notably punctual. Preferably, these are sequences which code for the same amino acid sequences as the reference sequence, this being related to the degeneration of the genetic code, or complementarity sequences that are likely to hybridize specifically with the reference sequences, preferably under highly stringent conditions, notably those defined below.

Hybridization under highly stringent conditions means that conditions related to temperature and ionic strength are selected in such a way that they allow hybridization to be maintained between two complementarity DNA fragments. On a purely illustrative basis, the highly stringent conditions of the hybridization step for the purpose of defining the polynucleotide fragments described above are advantageously as follows.

DNA-DNA or DNA-RNA hybridization is carried out in two steps: (1) prehybridization at 42° C. for three hours in phosphate buffer (20 mM, pH 7.5) containing 5×SSC (1×SSC corresponds to a solution of 0.15 M NaCl+0.015 M sodium citrate), 50% formamide, 7% sodium dodecyl sulfate (SDS), 10× Denhardt's, 5% dextran sulfate and 1% salmon sperm DNA; (2) primary hybridization for 20 hours at a temperature depending on the length of the probe (i.e.: 42° C. for a probe >100 nucleotides in length) followed by two 20-minute washings at 20° C. in 2×SSC+2% SDS, one 20-minute washing at 20° C. in 0.1×SSC+0.1% SDS. The last washing is carried out in 0.1×SSC+0.1% SDS for 30 minutes at 60° C. for a probe >100 nucleotides in length. The highly stringent hybridization conditions described above for a polynucleotide of defined size can be adapted by a person skilled in the art for longer or shorter oligonucleotides, according to the procedures described in Sambrook, et al. (Molecular cloning: a laboratory manual, Cold Spring Harbor Laboratory; 3rd edition, 2001).

The invention also relates to a vector comprising a nucleic acid as described in the invention.

The invention notably targets cloning and/or expression vectors that contain such a nucleotide sequence.

The vectors of the invention preferably contain elements which allow the expression and/or the secretion of nucleotide sequences in a given host cell. The vector thus must contain a promoter, translation initiation and termination signals, as well as suitable transcription regulation regions. It must be able to be maintained in a stable manner in the host cell and may optionally have specific signals which specify secretion of the translated protein. These various elements are selected and optimized by a person skilled in the art according to the host cell used. For this purpose, the nucleotide sequences can be inserted in self-replicating vectors within the chosen host or be integrative vectors of the chosen host.

Such vectors are prepared by methods typically used by a person skilled in the art and the resulting clones can be introduced into a suitable host by standard methods such as lipofection, electroporation, heat shock or chemical methods.

The vectors are, for example, vectors of plasmid or viral origin. They are used to transform host cells in order to clone or express the nucleotide sequences of the invention.

The invention also comprises isolated host cells transformed by or comprising a vector as described in the present invention.

The host cell can be selected among prokaryotic or eukaryotic systems such as bacterial cells, for example, but also yeast cells or animal cells, notably mammal cells (with the exception of human). Insect or plant cells can also be used.

The invention also relates to animals, other than human, that have a transformed cell according to the invention.

Another aspect of the invention relates to a method for the production of an antigen binding protein according to the invention, or an antigen binding fragment thereof, characterized in that said method comprises the following steps:

a) the culture in a medium with the suitable culture conditions for a host cell according to the invention; and b) the recovery of the antigen binding protein, or one of its antigen binding fragments, thus produced from the culture medium or from said cultured cells.

The transformed cells according to the invention are of use in methods for the preparation of recombinant antigen binding proteins according to the invention. Methods for the preparation of antigen binding proteins according to the invention in recombinant form, characterized in that said methods use a vector and/or a cell transformed by a vector according to the invention, are also comprised in the present invention. Preferably, a cell transformed by a vector according to the invention is cultured under conditions that allow the expression of the aforesaid antigen binding protein and recovery of said recombinant protein.

As already mentioned, the host cell can be selected among prokaryotic or eukaryotic systems. In particular, it is possible to identify the nucleotide sequences of the invention that facilitate secretion in such a prokaryotic or eukaryotic system. A vector according to the invention carrying such a sequence can thus be used advantageously for the production of recombinant proteins to be secreted. Indeed, the purification of these recombinant proteins of interest will be facilitated by the fact that they are present in the supernatant of the cellular culture rather than inside host cells.

The antigen binding protein of the invention can also be prepared by chemical synthesis. One such method of preparation is also an object of the invention. A person skilled in the art knows methods for chemical synthesis, such as solid-phase techniques (see notably Steward et al., 1984, Solid phase peptides synthesis, Pierce Chem. Company, Rockford, 111, 2nd ed., pp 71-95) or partial solid-phase techniques, by condensation of fragments or by conventional synthesis in solution. Polypeptides obtained by chemical synthesis and capable of containing corresponding unnatural amino acids are also comprised in the invention.

The antigen binding protein, or the antigen binding fragments of same, likely to be obtained by the method of the invention are also comprised in the present invention.

According to a particular aspect, the invention concerns an antigen binding protein, or an antigen binding fragment thereof, as above described for use as an addressing product for delivering a cytotoxic agent at a host target site, said host target site consisting of an epitope localized into the protein Axl extracellular domain, preferably the human protein Axl extracellular domain, more preferably the human protein Axl extracellular domain having the sequence SEQ ID NO. 31 or 32, or natural variant sequence thereof.

In a preferred embodiment, said host target site is a target site of a mammalian cell, more preferably of a human cell, more preferably cells which naturally or by way of genetical recombination, express the Axl protein.

The invention relates to an immunoconjugate comprising the antigen binding protein as described in the present specification conjugated to a cytotoxic agent.

In the sense of the present invention, the expression "immunoconjugate" or "immuno-conjugate" refers generally to a compound comprising at least an addressing product physically linked with a one or more therapeutic agent(s), thus creating a highly targeted compound.

In a preferred embodiment, such therapeutic agents consist of cytotoxic agents.

By "cytotoxic agent" or "cytotoxic", it is intended an agent which, when administered to a subject, treats or prevents the development of cell proliferation, preferably the development of cancer in the subject's body, by inhibiting or preventing a cellular function and/or causing cell death.

Many cytotoxic agents have been isolated or synthesized and make it possible to inhibit the cells proliferation, or to destroy or reduce, if not definitively, at least significantly the tumour cells. However, the toxic activity of these agents is not limited to tumour cells, and the non-tumour cells are also effected and can be destroyed. More particularly, side effects are observed on rapidly renewing cells, such as haematopoietic cells or cells of the epithelium, in particular of the mucous membranes. By way of illustration, the cells of the gastrointestinal tract are largely effected by the use of such cytotoxic agents.

One of the aims of the present invention is also to be able to provide a cytotoxic agent which makes it possible to limit the side effects on normal cells while at the same time conserving a high cytotoxicity on tumour cells.

More particularly, the cytotoxic agent may preferably consist of, without limitation, a drug (i.e "antibody-drug conjugate"), a toxin (i.e. "immunotoxin" or "antibody-toxin conjugate"), a radioisotope (i.e. "radioimmunoconjugate" or "antibody-radioisotope conjugate"), etc.

In a first preferred embodiment of the invention, the immunoconjugate consists of a binding protein linked to at least a drug or a medicament. Such an immunoconjugate is referred as an antibody-drug conjugate (or "ADC") when the binding protein is an antibody, or an antigen binding fragment thereof.

In a first embodiment, such drugs can be described regarding their mode of action. As non limitative example, it can be mentioned alkylating agents such as nitrogen mustard, alkyle-sulfonates, nitrosourea, oxazophorins, aziridines or imine-ethylenes, anti-metabolites, anti-tumor antibiotics, mitotic inhibitors, chromatin function inhibitors, anti-angiogenesis agents, anti-estrogens, anti-androgens, chelating agents, Iron absorption stimulant, Cyclooxygenase inhibitors, Phosphodiesterase inhibitors, DNA inhibitors, DNA synthetis inhibitors, Apopstotis stimulants, Thymidylate inhibitors, T cell inhibitors, Interferon agonists, Ribonucleoside triphosphate reductase inhibitors, Aromatase inhibitors, Estrogen receptor antagonists, Tyrosine kinase inhibitors, Cell cycle inhibitors, Taxane, Tubulin inhibitors, angiogenesis inhibitors, macrophage stimulants, Neurokinin receptor antagonists, Cannabinoid receptor agonists, Dopamine receptor agonists, granulocytes stimulating factor agonists, Erythropoietin receptor agonists, somatostatin receptor agonists, LHRH agonists, Calcium sensitizers, VEGF receptor antagonists, interleukin receptor antagonists, osteoclast inhibitors, radical formation stimulants, endothelin receptor antagonists, Vinca alkaloid, anti-hormone or immunomodulators or any other new drug that fullfills the activity criteria of a cytotoxic or a toxin.

Such drugs are, for example, cited in the VIDAL 2010, on the page devoted to the compounds attached to the cancerology and hematology column "Cytotoxics", these cytotoxic compounds cited with reference to this document are cited here as preferred cytotoxic agents.

More particularly, without limitation, the following drugs are preferred according to the invention: mechlorethamine, chlorambucol, melphalen, chlorydrate, pipobromen, prednimustin, disodic-phosphate, estramustine, cyclophosphamide, altretamine, trofosfamide, sulfofosfamide, ifosfamide, thiotepa, triethylenamine, altetramine, carmustine, streptozocin, fotemustin, lomustine, busulfan, treosulfan, improsulfan, dacarbazine, cis-platinum, oxaliplatin, lobaplatin, heptaplatin, miriplatin hydrate, carboplatin, methotrexate, pemetrexed, 5-fluoruracil, floxuridine, 5-fluorodeoxyuridine, capecitabine, cytarabine, fludarabine, cytosine arabinoside, 6-mercaptopurine (6-MP), nelarabine, 6-thioguanine (6-TG), chlorodesoxyadenosine, 5-azacytidine, gemcitabine, cladribine, deoxycoformycin, tegafur, pentostatin, doxorubicin, daunorubicin, idarubicin, valrubicin, mitoxantrone, dactinomycin, mithramycin, plicamycin, mitomycin C, bleomycin, procarbazine, paclitaxel, docetaxel, vinblastine, vincristine, vindesine, vinorelbine, topotecan, irinotecan, etoposide, valrubicin, amrubicin hydrochloride, pirarubicin, elliptinium acetate, zorubicin, epirubicin, idarubicin and teniposide, razoxin, marimastat, batimastat, prinomastat, tanomastat, ilomastat, CGS-27023A, halofuginon, COL-3, neovastat, thalidomide, CDC 501, DMXAA, L-651582, squalamine, endostatin, SU5416, SU6668, interferon-alpha, EMD121974, interleukin-12, IM862, angiostatin, tamoxifen, toremifene, raloxifene, droloxifene, iodoxyfene, anastrozole, letrozole, exemestane, flutamide, nilutamide, sprironolactone, cyproterone acetate, finasteride, cimitidine, bortezomid, Velcade, bicalutamide, cyproterone, flutamide, fulvestran, exemestane, dasatinib, erlotinib, gefitinib, imatinib, lapatinib, nilotinib, sorafenib, sunitinib, retinoid, rexinoid, methoxsalene, methylaminolevulinate, aldesleukine, OCT-43, denileukin diflitox, interleukin-2, tasonermine, lentinan, sizofilan, roquinimex, pidotimod, pegademase, thymopentine, poly I:C, procodazol, Tic BCG, *corynebacterium parvum*, NOV-002, ukrain, levamisole, 1311-chTNT, H-101, celmoleukin, interferon alfa2a, interferon alfa2b, interferon gamma1a, interleukin-2, mobenakin, Rexin-G, teceleukin, aclarubicin, actinomycin, arglabin, asparaginase, carzinophilin, chromomycin, daunomycin, leucovorin, masoprocol, neocarzinostatin, peplomycin, sarkomycin, solamargine, trabectedin, streptozocin, testosterone, kunecatechins, sinecatechins, alitretinoin, belotecan hydrocholoride, calusterone, dromostanolone, elliptinium acetate, ethinyl estradiol, etoposide, fluoxymesterone, formestane, fosfetrol, goserelin acetate, hexyl aminolevulinate, histrelin, hydroxyprogesterone, ixabepilone, leuprolide, medroxyprogesterone acetate, megesterol acetate, methylprednisolone, methyltestosterone, miltefosine, mitobronitol, nadrolone phenylpropionate, norethindrone acetate, prednisolone, prednisone, temsirrolimus, testolactone, triamconolone, triptorelin, vapreotide acetate, zinostatin stimalamer, amsacrine, arsenic trioxide, bisantrene hydrochloride, chlorambucil, chlortrianisene, cis-diaminedichloroplatinium, cyclophosphamide, diethylstilbestrol, hexamethylmelamine, hydroxyurea, lenalidomide, lonidamine, mechlorethanamine, mitotane, nedaplatin, nimustine hydrochloride, pamidronate, pipobroman, porfimer sodium, ranimustine, razoxane, semustine, sobuzoxane, mesylate, triethylenemelamine, zoledronic acid, camostat mesylate, fadrozole HCl, nafoxidine, aminoglutethimide, carmofur, clofarabine, cytosine arabinoside, decitabine, doxifluridine, enocitabine, fludarabne phosphate, fluorouracil, ftorafur, uracil mustard, abarelix, bexarotene, raltiterxed, tamibarotene, temozolomide, vorinostat, megastrol, clodronate disodium, levamisole, ferumoxytol, iron isomaltoside, celecoxib, ibudilast, bendamustine, altretamine, mitolactol, temsirolimus, pralatrexate, TS-1, decitabine, bicalutamide, flutamide, letrozole, clodronate disodium, degarelix, toremifene citrate, histamine dihydrochloride, DW-166HC, nitracrine, decitabine, irinoteacn hydrochloride, amsacrine, romidepsin, tretinoin, cabazitaxel, vandetanib, lenalidomide, ibandronic acid, miltefosine, vitespen, mifamurtide, nadroparin, granisetron, ondansetron, tropisetron, alizapride, ramosetron, dolasetron mesilate, fosaprepitant dimeglumine, nabilone, aprepitant, dronabinol, TY-10721, lisuride hydrogen maleate, epiceram, defibrotide, dabigatran etexilate, filgrastim, pegfilgrastim, reditux, epoetin, molgramostim, oprelvekin, sipuleucel-T, M-Vax, acetyl L-carnitine, donepezil hydrochloride, 5-aminolevulinic acid, methyl aminolevulinate, cetrorelix acetate, icodextrin, leuprorelin, methylphenidate, octreotide, amlexanox, plerixafor, menatetrenone, anethole dithiolethione, doxercalciferol, cinacalcet hydrochloride, alefacept, romiplostim, thymoglobulin, thymalfasin, ubenimex, imiquimod, everolimus, sirolimus, H-101, lasofoxifene, trilostane, incadronate, gangliosides, pegaptanib octasodium, vertoporfin, minodronic acid, zoledronic acid, gallium nitrate, alendronate sodium, etidronate disodium, disodium pamidronate, dutasteride, sodium stibogluconate, armodafinil, dexrazoxane, amifostine, WF-10, temoporfin, darbepoetin alfa, ancestim, sargramostim, palifermin, R-744, nepidermin, oprelvekin, denileukin diftitox, crisantaspase, buserelin, deslorelin, lanreotide, octreotide, pilocarpine, bosentan, calicheamicin, maytansinoids and ciclonicate.

For more detail, the person skilled in the art could refer to the manual edited by the "Association Française des Enseignants de Chimie Thérapeutique" and entitled "traité de chimie thérapeutique, vol. 6, Médicaments antitumoraux et perspectives dans le traitement des cancers, edition TEC & DOC, 2003".

In a second preferred embodiment of the invention, the immunoconjugate consists of a binding protein linked to at least a radioisotope. Such an immunoconjugate is referred as an antibody-radioisotope conjugate (or "ARC") when the binding protein is an antibody, or an antigen binding fragment thereof.

For selective destruction of the tumor, the antibody may comprise a highly radioactive atom. A variety of radioactive isotopes are available for the production of ARC such as, without limitation, $At^{211}$, $C^{13}$, $N^{15}$, $O^{17}$, $Fl^{19}$, $I^{123}$, $I^{131}$, $I^{125}$, $In^{111}$, $Y^{90}$, $Re^{186}$, $Re^{188}$, $Sm^{153}$, $tc^{99}m$, $Bi^{212}$, $P^{32}$, $Pb^{212}$, radioactive isotopes of Lu, gadolinium, manganese or iron.

Any methods or processes known by the person skilled in the art can be used to incorporate such radioisotope in the ARC (see, for example "Monoclonal Antibodies in Immunoscintigraphy", Chatal, CRC Press 1989). As non limitative example, $tc^{99}m$ or $I^{123}$, $Re^{186}$, $Re^{188}$ and $In^{111}$ can be attached via a cysteine residue. $Y^{90}$ can be attached via a lysine residue. $I^{123}$ can be attached using the IODOGEN method (Fraker et al (1978) Biochem. Biophys. Res. Commun 80: 49-57).

Several examples can be mentioned to illustrate the knowledge of the person skilled in the art in the field of ARC such as Zevalin® which is an ARC composed of an anti-CD20 monoclonal antibody and $In^{111}$ or $Y^{90}$ radioisotope bound by a thiourea linker-chelator (Wiseman et at (2000) Eur. Jour. Nucl. Med. 27(7):766-77; Wiseman et al (2002) Blood 99(12):4336-42; Witzig et at (2002) J. Clin. Oncol. 20(10): 2453-63; Witzig et al (2002) J. Clin. Oncol. 20(15):3262-69); or Mylotarg® which is composed of an anti-CD33 antibody linked to calicheamicin, (U.S. Pat. Nos. 4,970,198; 5,079, 233; 5,585,089; 5,606,040; 5,693,762; 5,739,116; 5,767,285; 5,773,001). More recently, it can also be mentioned the ADC referred as Adcetris (corresponding to the Brentuximab vedotin) which has been recently accepted by the FDA in the treatment of Hodgkin's lymphoma (Nature, vol. 476, pp 380-381, 25 Aug. 2011).

In a third preferred embodiment of the invention, the immunoconjugate consists of a binding protein linked to at least a toxin. Such an immunoconjugate is referred as an antibody-toxin conjugate (or "ATC") when the binding protein is an antibody, or an antigen binding fragment thereof.

Toxins are effective and specific poisons produced by living organisms. They usually consist of an amino acid chain which can vary in molecular weight between a couple of hundred (peptides) and one hundred thousand (proteins). They may also be low-molecular organic compounds. Toxins are produced by numerous organisms, e.g., bacteria, fungi, algae and plants. Many of them are extremely poisonous, with a toxicity that is several orders of magnitude greater than the nerve agents.

Toxins used in ATC can include, without limitation, all kind of toxins which may exert their cytotoxic effects by mechanisms including tubulin binding, DNA binding, or topoisomerase inhibition.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

Small molecule toxins, such as dolastatins, auristatins, a trichothecene, and CC1065, and the derivatives of these toxins that have toxin activity, are also contemplated herein. Dolastatins and auristatins have been shown to interfere with microtubule dynamics, GTP hydrolysis, and nuclear and cellular division and have anticancer and antifungal activity.

"Linker", "Linker Unit", or "link" means a chemical moiety comprising a covalent bond or a chain of atoms that covalently attaches a binding protein to at least one cytotoxic agent.

Linkers may be made using a variety of bifunctional protein coupling agents such as N-succinimidyl-3-(2-pyridyldithio) propionate (SPDP), succinimidyl-4-(N-maleimidomethyl)cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Carbon-14-labeled 1-isothiocyanatobenzyl-3-methyldiethylene triaminepentaacetic acid (MX-DTPA) is an exemplary chelating agent for conjugation of cyctotoxic agents to the addressing system. Other cross-linker reagents may be BMPS, EMCS, GMBS, HBVS, LC-SMCC, MBS, MPBH, SBAP, SIA, STAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

The linker may be a "non cleavable" or "cleavable".

In a preferred embodiment, it consists in a "cleavable linker" facilitating release of the cytotoxic agent in the cell. For example, an acid-labile linker, peptidase-sensitive linker, photolabile linker, dimethyl linker or disulfide-containing linker may be used. The linker is, in a preferred embodiment, cleavable under intracellular conditions, such that cleavage of the linker releases the cytotoxic agent from the binding protein in the intracellular environment.

For example, in some embodiments, the linker is cleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease. Typically, the peptidyl linker is at least two amino acids long or at least three amino acids long. Cleaving agents can include cathepsins B and D and plasmin, all of which are known to hydrolyze dipeptide drug derivatives resulting in the release of active drug inside target cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). In specific embodiments, the peptidyl linker cleavable by an intracellular protease is a Val-Cit linker or a Phe-Lys linker. One advantage of using intracellular proteolytic release of the cytotoxic agent is that the agent is typically attenuated when conjugated and the serum stabilities of the conjugates are typically high.

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT.

As non limitative example of non-cleavable or "non reductible" linkers, it can be mentioned the immunoconjugate Trastuzumab-DM1 (TDM1) which combines trastuzumab with a linked chemotherapy agent, maytansine (Cancer Research 2008; 68: (22). Nov. 15, 2008).

In a preferred embodiment, the immunoconjugate of the invention may be prepared by any method known by the person skilled in the art such as, without limitation, i) reaction of a nucleophilic group of the antigen binding protein with a bivalent linker reagent followed by reaction with the cytotoxic agent or ii) reaction of a nucleophilic group of a cytotoxic agent with a bivalent linker reagent followed by reaction with the nucleophilic group of the antigen binding protein.

Nucleophilic groups on antigen binding protein include, without limitation, N-terminal amine groups, side chain amine groups, e.g. lysine, side chain thiol groups, and sugar hydroxyl or amino groups when the antigen binding protein is glycosylated. Amine, thiol, and hydroxyl groups are nucleophilic and capable of reacting to form covalent bonds with electrophilic groups on linker moieties and linker reagents including, without limitation, active esters such as NHS esters, HOBt esters, haloformates, and acid halides; alkyl and benzyl halides such as haloacetamides; aldehydes, ketones, carboxyl, and maleimide groups. The antigen binding protein may have reducible interchain disulfides, i.e. cysteine bridges. The antigen binding proteins may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into the antigen binding protein through any reaction known by the person skilled in the art. As non limitative example, reactive thiol groups may be introduced into the antigen binding protein by introducing one or more cysteine residues.

Immunoconjugates may also be produced by modification of the antigen binding protein to introduce electrophilic moieties, which can react with nucleophilic substituents on the linker reagent or cytotoxic agent. The sugars of glycosylated antigen binding protein may be oxidized to form aldehyde or ketone groups which may react with the amine group of linker reagents or cytotoxic agent. The resulting imine Schiff base groups may form a stable linkage, or may be reduced to form stable amine linkages. In one embodiment, reaction of the carbohydrate portion of a glycosylated antigen binding protein with either galactose oxidase or sodium meta-periodate may yield carbonyl (aldehyde and ketone) groups in the protein that can react with appropriate groups on the drug. In another embodiment, proteins containing N-terminal serine or threonine residues can react with sodium meta-periodate, resulting in production of an aldehyde in place of the first amino acid.

In certain preferred embodiments, the linker unit may have the following general formula:

-Ta-Ww-Yywherein:
-T- is a stretcher unit;
a is 0 or 1;
-W- is an amino acid unit;
w is independently an integer ranging from 1 to 12;
-Y- is a spacer unit;
y is 0, 1 or 2.

The stretcher unit (-T-), when present, links the antigen binding protein to an amino acid unit (-W-). Useful functional groups that can be present on the antigen binding protein, either naturally or via chemical manipulation, include sulfhydryl, amino, hydroxyl, the anomeric hydroxyl group of a carbohydrate, and carboxyl. Suitable functional groups are sulfhydryl and amino Sulfhydryl groups can be generated by reduction of the intramolecular disulfide bonds of the antigen binding protein, if present. Alternatively, sulfhydryl groups can be generated by reaction of an amino group of a lysine moiety of the antigen binding protein with 2-iminothiolane or other sulfhydryl generating reagents. In specific embodiments, the antigen binding protein is a recombinant antibody and is engineered to carry one or more lysines. More preferably, the antigen binding protein can be engineered to carry one or more Cysteines (cf. ThioMabs).

In certain specific embodiments, the stretcher unit forms a bond with a sulfur atom of the antigen binding protein. The sulfur atom can be derived from a sulfhydryl (—SH) group of a reduced antigen binding protein.

In certain other specific embodiments, the stretcher unit is linked to the antigen binding protein via a disulfide bond between a sulfur atom of the antigen binding protein and a sulfur atom of the stretcher unit.

In other specific embodiments, the reactive group of the stretcher contains a reactive site that can be reactive to an amino group of the antigen binding protein. The amino group can be that of an arginine or a lysine. Suitable amine reactive sites include, but are not limited to, activated esters such as succinimide esters, 4-nitrophenyl esters, pentafluorophenyl esters, anhydrides, acid chlorides, sulfonyl chlorides, isocyanates and isothiocyanates.

In yet another aspect, the reactive function of the stretcher contains a reactive site that is reactive to a modified carbohydrate group that can be present on the antigen binding protein. In a specific embodiment, the antigen binding protein is glycosylated enzymatically to provide a carbohydrate moiety (to be noticed that, when the antigen binding protein is an antibody, said antibody is generally naturally glycosylated). The carbohydrate may be mildly oxidized with a reagent such as sodium periodate and the resulting carbonyl unit of the oxidized carbohydrate can be condensed with a stretcher that contains a functionality such as a hydrazide, an oxime, a reactive amine, a hydrazine, a thiosemicarbazide, a hydrazine carboxylate, or an arylhydrazide.

The amino acid unit (-W-) links the stretcher unit (-T-) to the Spacer unit (-Y-) if the spacer unit is present, and links the stretcher unit to the cytotoxic agent if the spacer unit is absent.

As above mentioned, -Ww- may be a dipeptide, tripeptide, tetrapeptide, pentapeptide, hexapeptide, heptapeptide, octapeptide, nonapeptide, decapeptide, undecapeptide or dodecapeptide unit In some embodiments, the amino acid unit may comprise amino acid residues such as, without limitation, alanine, valine, leucine, isoleucine, methionine, phenylalanine, tryptophan, proline, lysine protected with acetyl or formyl, arginine, arginine protected with tosyl or nitro groups, histidine, ornithine, ornithine protected with acetyl or formyl and citrulline. Exemplary amino acid linker components include preferably a dipeptide, a tripeptide, a tetrapeptide or a pentapeptide.

Exemplary dipeptides include: Val-Cit, Ala-Val, Lys-Lys, Cit-Cit, Val-Lys, Ala-Phe, Phe-Lys, Ala-Lys, Phe-Cit, Leu-Cit, Ile-Cit, Trp-Cit, Phe-Ala, Phe-$N^9$-tosyl-Arg, Phe-$N^9$-Nitro-Arg.

Exemplary tripeptides include: Val-Ala-Val, Ala-Asn-Val, Val-Leu-Lys, Ala-Ala-Asn, Phe-Phe-Lys, Gly-Gly-Gly, D-Phe-Phe-Lys, Gly-Phe-Lys.

Exemplary tetrapeptide include: Gly-Phe-Leu-Gly (SEQ ID NO. 33), Ala-Leu-Ala-Leu (SEQ ID NO. 34).

Exemplary pentapeptide include: Pro-Val-Gly-Val-Val (SEQ ID NO. 35).

Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzyme, for example, a tumor-associated protease, cathepsin B, C and D, or a plasmin protease.

The amino acid unit of the linker can be enzymatically cleaved by an enzyme including, but not limited to, a tumor-associated protease to liberate the cytotoxic agent.

The amino acid unit can be designed and optimized in its selectivity for enzymatic cleavage by a particular tumor-associated protease. The suitable units are those whose cleavage is catalyzed by the proteases, cathepsin B, C and D, and plasmin.

The spacer unit (-Y-), when present, links an amino acid unit to the cytotoxic agent. Spacer units are of two general types: self-immolative and non self-immolative. A non self-immolative spacer unit is one in which part or all of the spacer unit remains bound to the cytotoxic agent after enzymatic cleavage of an amino acid unit from the immunoconjugate. Examples of a non self-immolative spacer unit include, but are not limited to a (glycine-glycine) spacer unit and a glycine spacer unit. To liberate the cytotoxic agent, an independent hydrolysis reaction should take place within the target cell to cleave the glycine-drug unit bond.

In another embodiment, a non self-immolative the spacer unit (-Y-) is -Gly-.

In one embodiment, the immunoconjugate lacks a spacer unit (y=0). Alternatively, an immunoconjugate containing a self-immolative spacer unit can release the cytotoxic agent without the need for a separate hydrolysis step. In these embodiments, -Y- is a p-aminobenzyl alcohol (PAB) unit that is linked to -Ww- via the nitrogen atom of the PAB group, and connected directly to -D via a carbonate, carbamate or ether group.

Other examples of self-immolative spacers include, but are not limited to, aromatic compounds that are electronically equivalent to the PAB group such as 2-aminoimidazol-5-methanol derivatives and ortho or para-aminobenzylacetals. Spacers can be used that undergo facile cyclization upon amide bond hydrolysis, such as substituted and unsubstituted 4-aminobutyric acid amides, appropriately substituted bicyclo[2.2.1] and bicyclo[2.2.2] ring systems and 2-aminophenylpropionic acid amides.

In an alternate embodiment, the spacer unit is a branched bis(hydroxymethyl)styrene (BHMS) unit, which can be used to incorporate additional cytotoxic agents.

An embodiment of the invention is an immunoconjugate comprising an antigen binding protein which i) specifically binds to the human protein Axl, preferably having the sequence SEQ ID NO. 29 or 30 or natural variant sequence thereof, and ii) is internalized following its binding to said human protein Axl, said antigen binding protein being conjugated to at least one drug, toxin or radioisotope.

An embodiment of the invention relates to an immunoconjugate having formula (I)

$$Ab\text{-}(L\text{-}D)_n \qquad (I)$$

or a pharmaceutically acceptable salt or solvate thereof, wherein:

Ab is an antigen binding protein which i) specifically binds to the protein Axl, and ii) is internalized into a mammalian cell following its binding to said protein Axl when said Axl protein is expressed at the surface of said mammalian cell;

L is a linker;
D is a drug, a toxin and/or a radioisotope;
n is 1 to 12.

In a particular embodiment, the immunoconjugate of the invention has the formula (I)

$$Ab\text{-}(L\text{-}D)_n \qquad (I)$$

or a pharmaceutically acceptable salt or solvate thereof, wherein:

Ab is an antigen binding protein which i) specifically binds to the protein Axl with an $EC_{50}$ of at least $10^{-9}$ M, preferentially between $10^{-9}$ and $10^{-12}$ M., and ii) is internalized into a mammalian cell following its binding to said protein Axl when said Axl protein is expressed at the surface of said mammalian cell;

L is a linker;
D is a drug, a toxin and/or a radioisotope;
n is 1 to 12.

In another particular embodiment, the immunoconjugate of the invention has the formula (I)

$$Ab\text{-}(L\text{-}D)_n \qquad (I)$$

or a pharmaceutically acceptable salt or solvate thereof, wherein:

Ab is an antigen binding protein which i) specifically binds to the protein Axl, and ii) induces a reduction of MFI of at least 200;

L is a linker;
D is a drug, a toxin and/or a radioisotope;
n is 1 to 12.

In a particular embodiment, the immunoconjugate of the invention has the formula (I)

$$Ab\text{-}(L\text{-}D)_n \qquad (I)$$

or a pharmaceutically acceptable salt or solvate thereof, wherein:

Ab is an antigen binding protein which i) specifically binds to the protein Axl with an $EC_{50}$ of at least $10^{-9}$ M, preferentially between $10^{-9}$ and $10^{-12}$ M., and ii) induces a reduction of MFI of at least 200;

L is a linker;
D is a drug, a toxin and/or a radioisotope;
n is 1 to 12.

In an embodiment of the invention, the antigen binding protein of the immunoconjugate of the present invention is selected by the method for the screening of a compound, or a binding fragment thereof, capable of delivering or internalizing a molecule of interest into mammalian cells according to the present invention In an embodiment of the invention, the antigen binding protein induces a reduction of MFI of at least 200 as measured on SN12C cells.

In an embodiment of the invention, the antigen binding protein binds to the protein Axl with an $EC_{50}$ of at least $10^{-9}$ M, preferentially between $10^{-9}$ and $10^{-12}$ M, as measured on SN12C cells.

For the avoidance of doubt, the linker L can be selected through any linkers known by the person skilled in the art. As non limitative example, the linker L is selected in the group of linkers described above in the present specification.

For the avoidance of doubt, the Drug D can be selected through any drug, a toxin and/or a radioisotope known by the person skilled in the art. As non limitative example, the Drug D is selected in the group of drugs, toxins or radioisotopes described above in the present specification.

Finally, the invention relates to an immunoconjugate as above described for use in the treatment of cancer.

Cancers can be preferably selected through Axl-related cancers including tumoral cells expressing or over-expressing whole or part of the protein Axl at their surface.

More particularly, said cancers are breast, colon, esophageal carcinoma, hepatocellular, gastric, glioma, lung, melanoma, osteosarcoma, ovarian, prostate, rhabdomyosarcoma, renal, thyroid, uterine endometrial cancer, mesothelioma, oral squamous carcinoma and any drug resistance phenomena. Another object of the invention is a pharmaceutical composition comprising the immunoconjugate as described in the specification.

More particularly, the invention relates to a pharmaceutical composition comprising the immunoconjugate of the invention with at least an excipient and/or a pharmaceutical acceptable vehicle.

In the present description, the expression "pharmaceutically acceptable vehicle" or "excipient" is intended to indicate a compound or a combination of compounds entering into a pharmaceutical composition not provoking secondary reactions and which allows, for example, facilitation of the administration of the active compound(s), an increase in its lifespan and/or in its efficacy in the body, an increase in its solubility in solution or else an improvement in its conservation. These pharmaceutically acceptable vehicles and excipients are well known and will be adapted by the person skilled in the art as a function of the nature and of the mode of administration of the active compound(s) chosen.

Preferably, these immunoconjugates will be administered by the systemic route, in particular by the intravenous route, by the intramuscular, intradermal, intraperitoneal or subcutaneous route, or by the oral route. In a more preferred manner, the composition comprising the immunoconjugates according to the invention will be administered several times, in a sequential manner.

Their modes of administration, dosages and optimum pharmaceutical forms can be determined according to the criteria generally taken into account in the establishment of a treatment adapted to a patient such as, for example, the age or the body weight of the patient, the seriousness of his/her general condition, the tolerance to the treatment and the secondary effects noted.

Other characteristics and advantages of the invention appear in the continuation of the description with the examples and the figures whose legends are represented below.

FIGURE LEGENDS

FIG. 1: in vitro cytotoxicity assay using Mab-zap conjugated secondary antibody on SN12C cells.

Figure 2A:
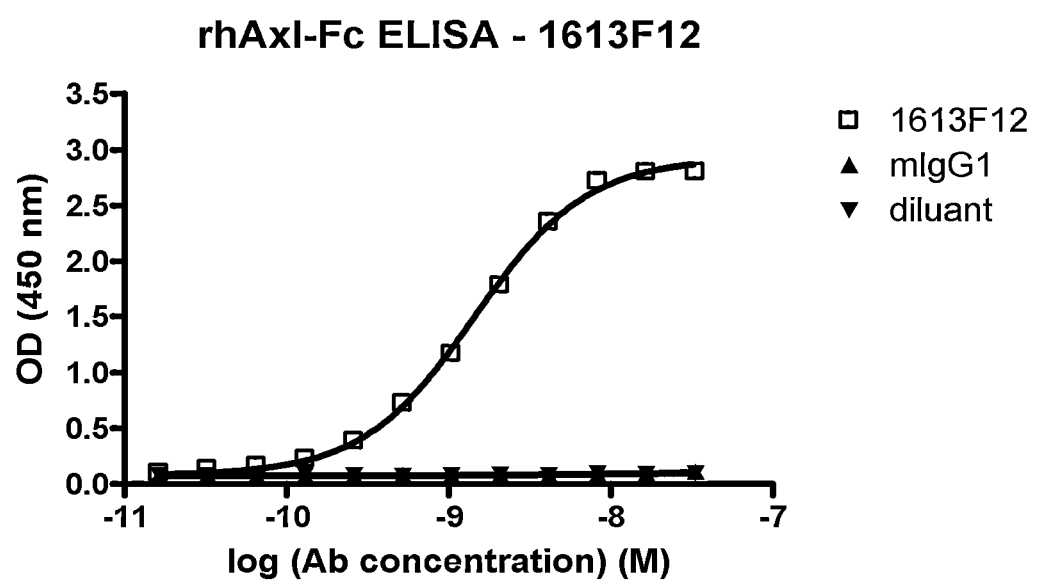
Figure 2B:
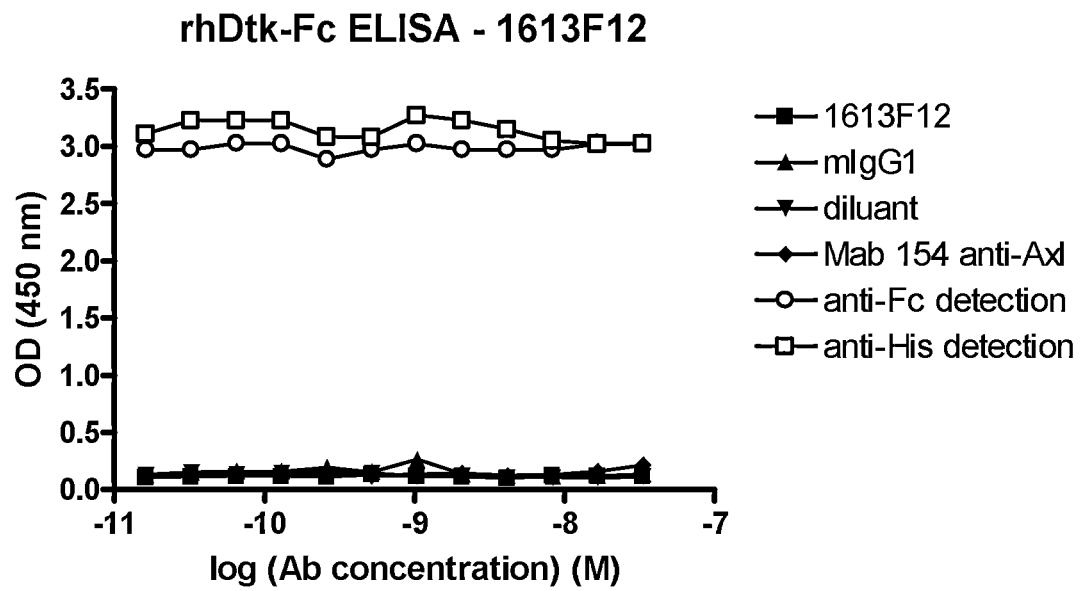
Figure 2C:
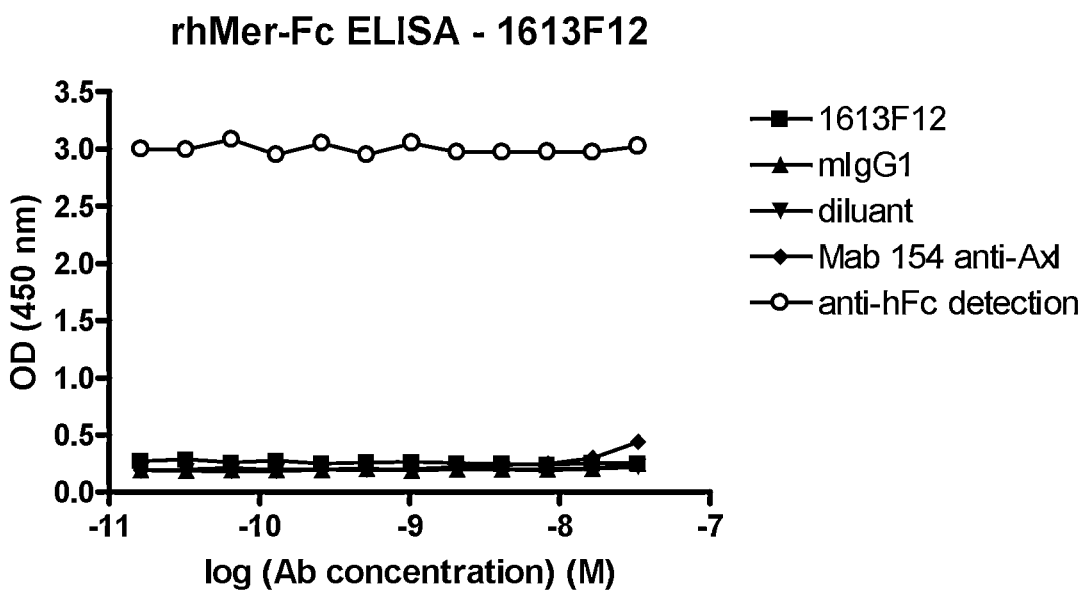

FIGS. 2A, 2B and 2C: Binding specificity of 1613F12 on the immobilized rhAxl-Fc protein (2A), rhDtk-Fc (2B) or rhMer-Fc (2C) proteins by ELISA.

Figure 3:
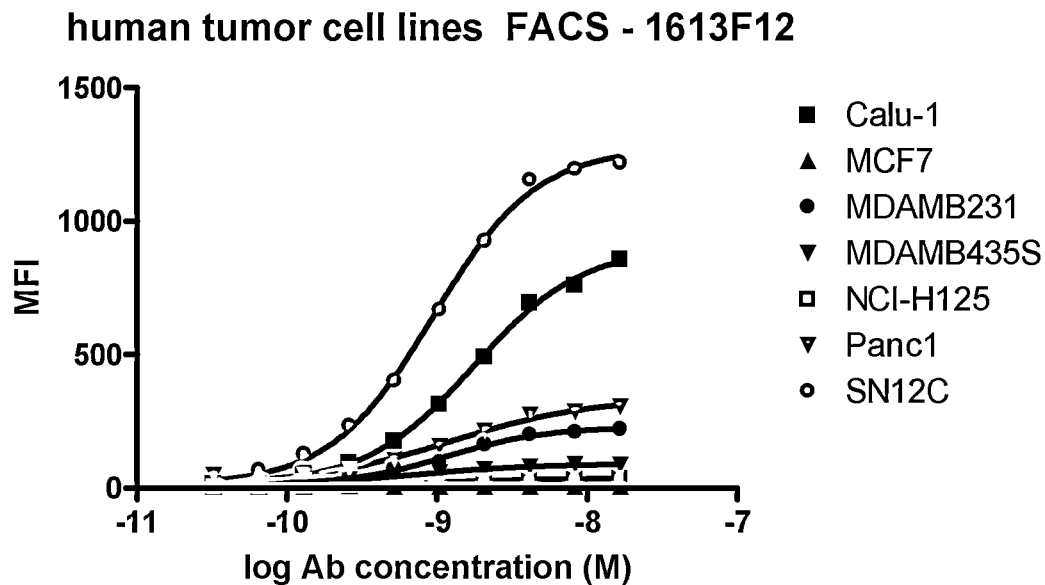

FIG. 3: FACS analysis of the 1613F12 binding on human tumor cells

Figure 4:
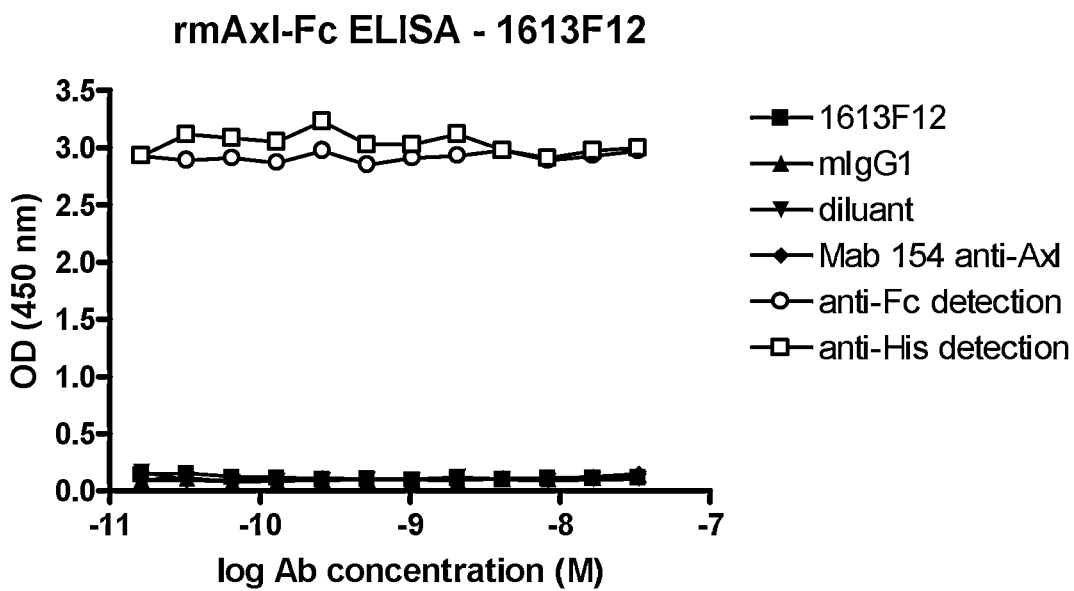

FIG. 4: ELISA on the immobilized rmAxl-Fc protein ("rm" for murine recombinant).

Figure 5:
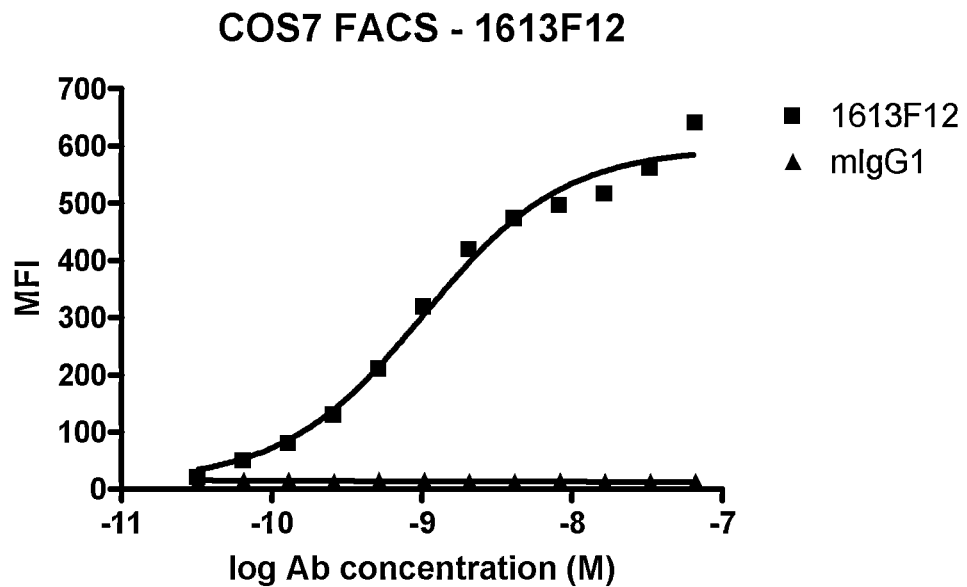

FIG. 5: 1613F12 binding on COS7 cells as determined by indirect labelling protocol using flow cytometry method.

Figure 6:
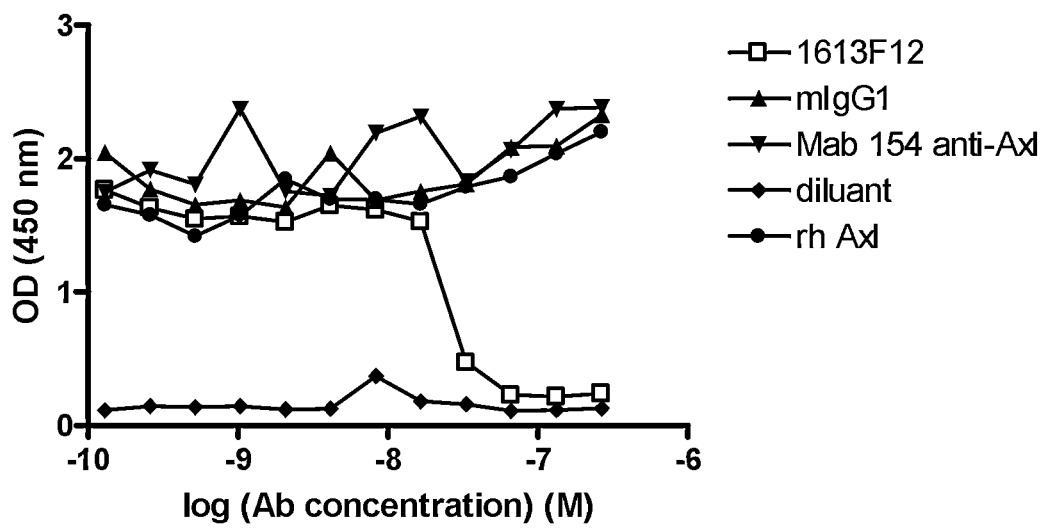

FIG. 6: Competition ELISA of Gas6 binding using 1613F12.

Figure 7:
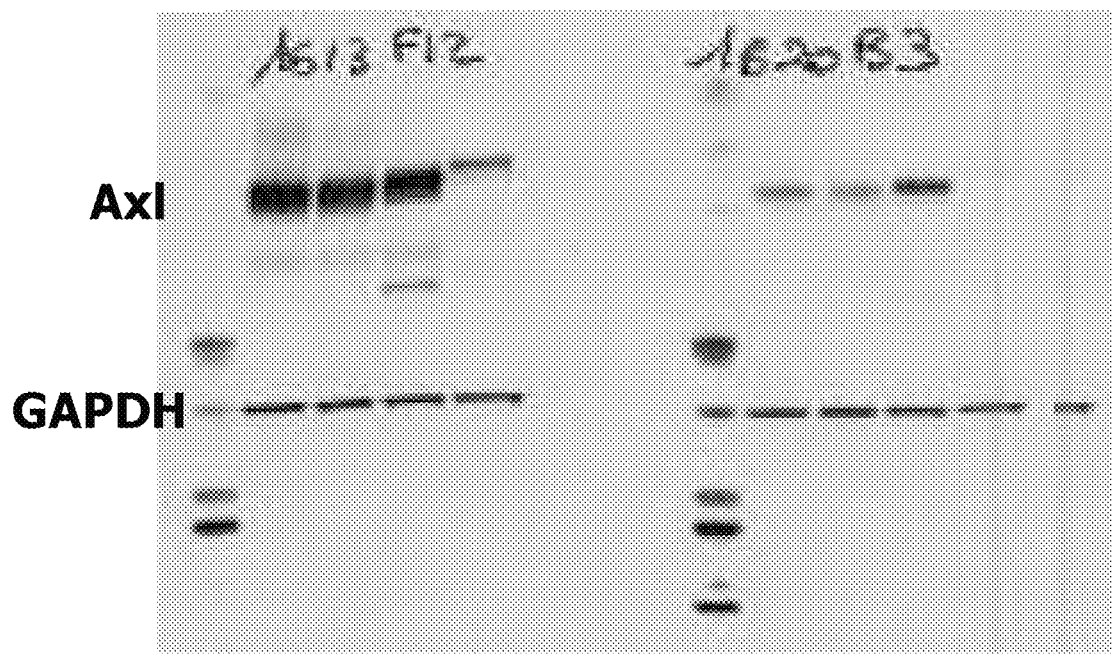

FIG. 7: Epitope binding analysis by western Blot using SN12C cell lysate. NH (no heat); NR (no reduction); H (heat); R (reduction). GAPDH detection attests to the correct sample loading on the gel.

Figure 8A:
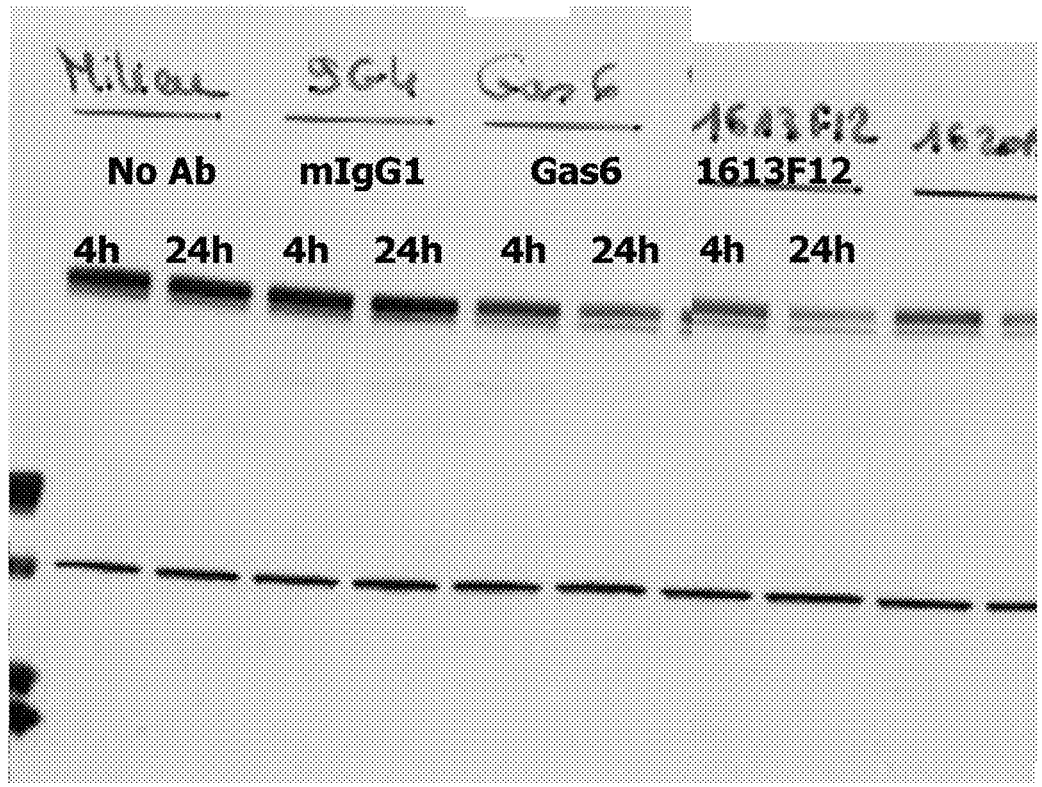
Figure 8B:
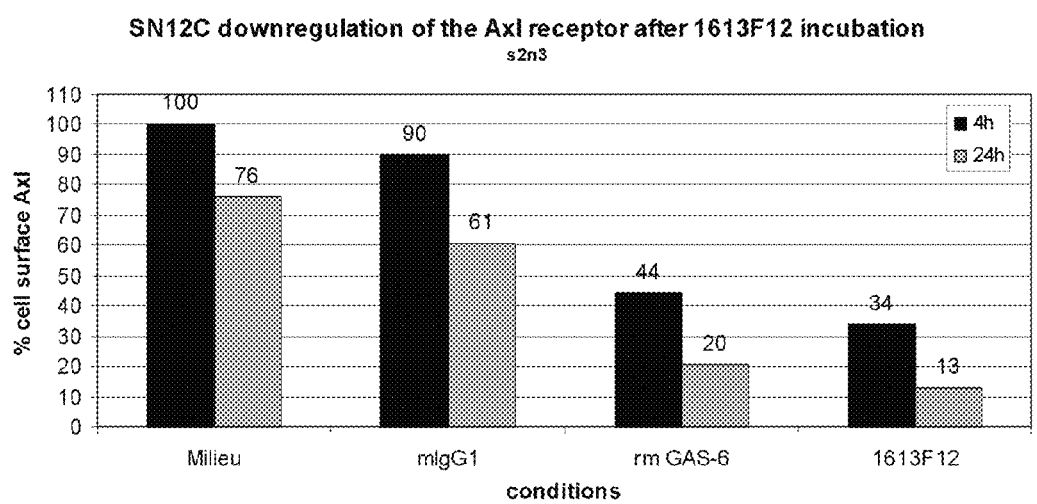

FIGS. 8A and 8B: Study of Axl downregulation after 1613F12 binding on SN12C cells by Western Blot with FIG. 8A—Western blot image representative of the 3 independent experiments performed (The western blot analysis was performed after a 4 h and 24 h incubation of the 1613F12 on SN12C cells); and FIG. 8B—Optical density quantification of the presented film using "QuantityOne" software.

Figure 9A:
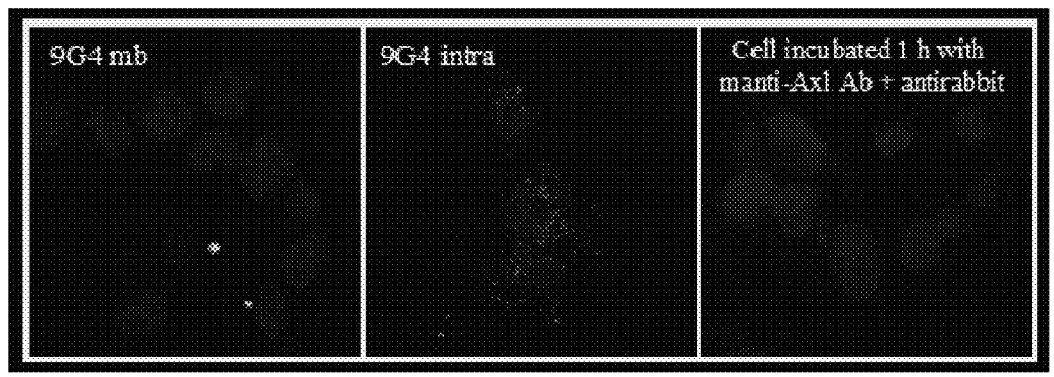
Figure 9B:
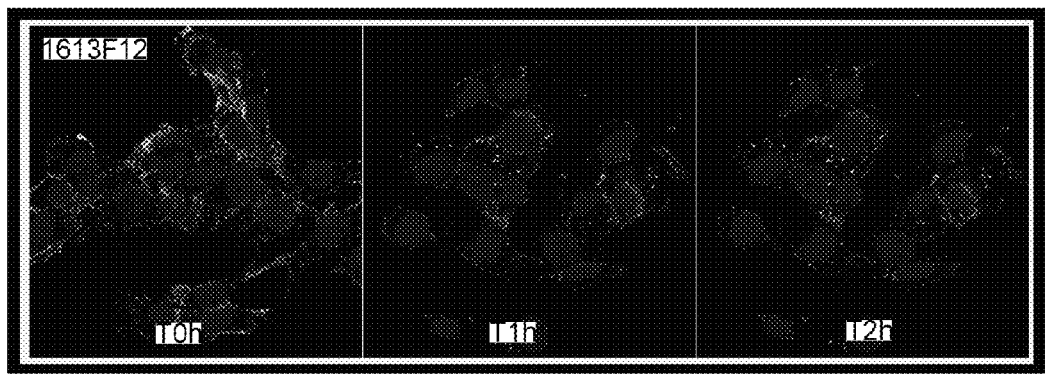
Figure 9C:
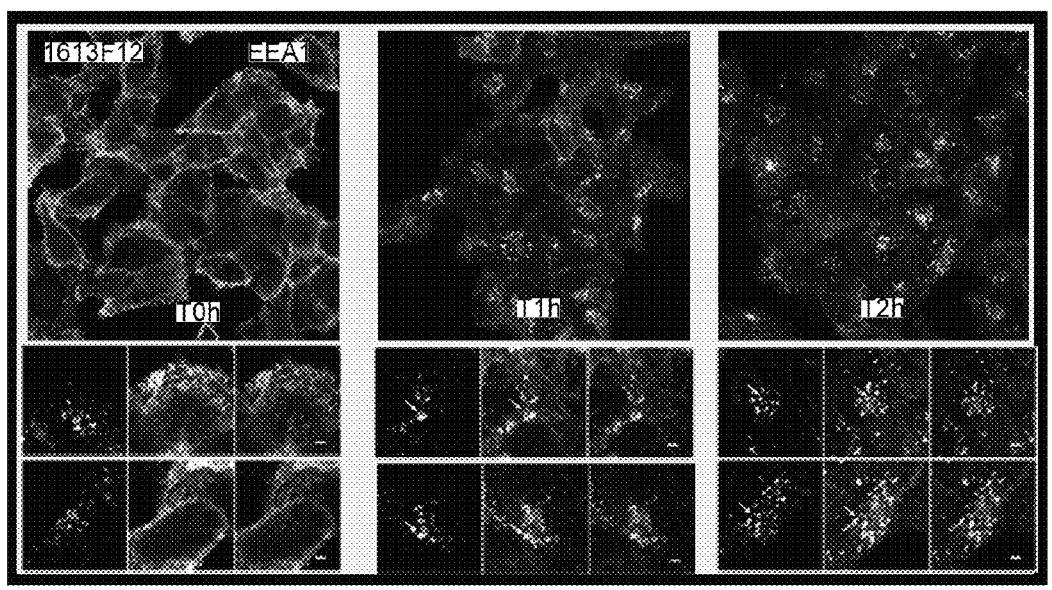

FIGS. 9A, 9B and 9C: Immunofluorescence microscopy of SN12C cells after incubation with the 1613F12 FIG. 9A—Photographs of the mIgG1 isotype control conditions both for the membrane and the intracellular staining FIG. 9B—Membrane staining FIG. 9C—Intracellular staining of both Axl receptor using the 1613F12 and of the early endosome marker EEA1. Image overlays are presented bellow and co-localizations visualized are indicated by the arrows.

Figure 10:
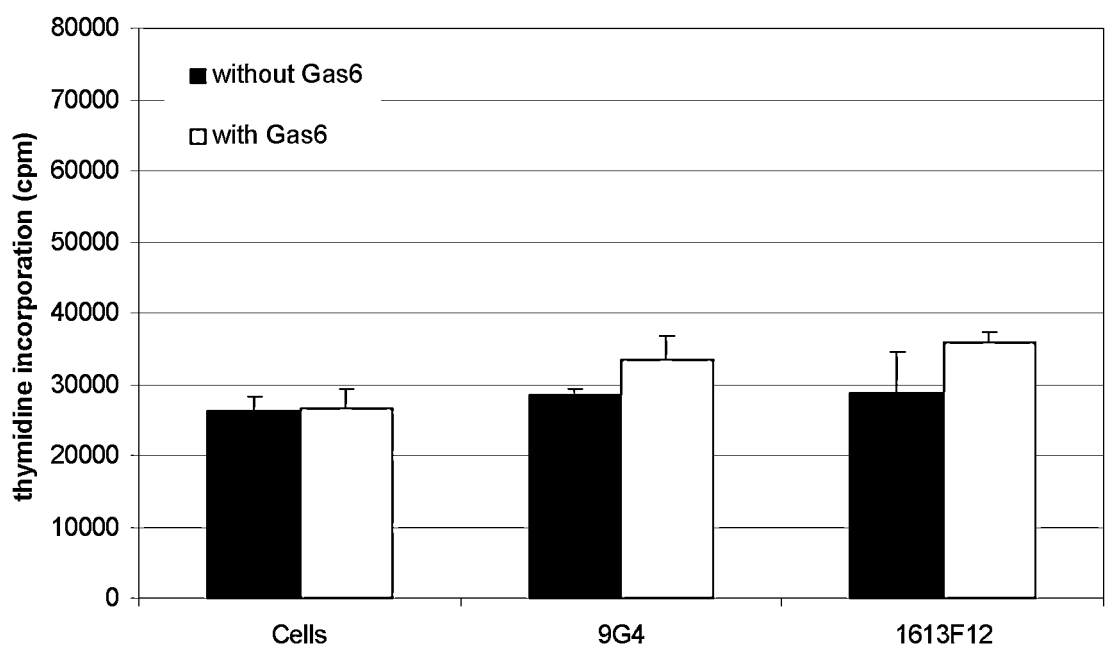
Figures 11A, 11B, 11C, 11D, 11E, 11F, 11G, 11H, 11I, 11J, 11K:
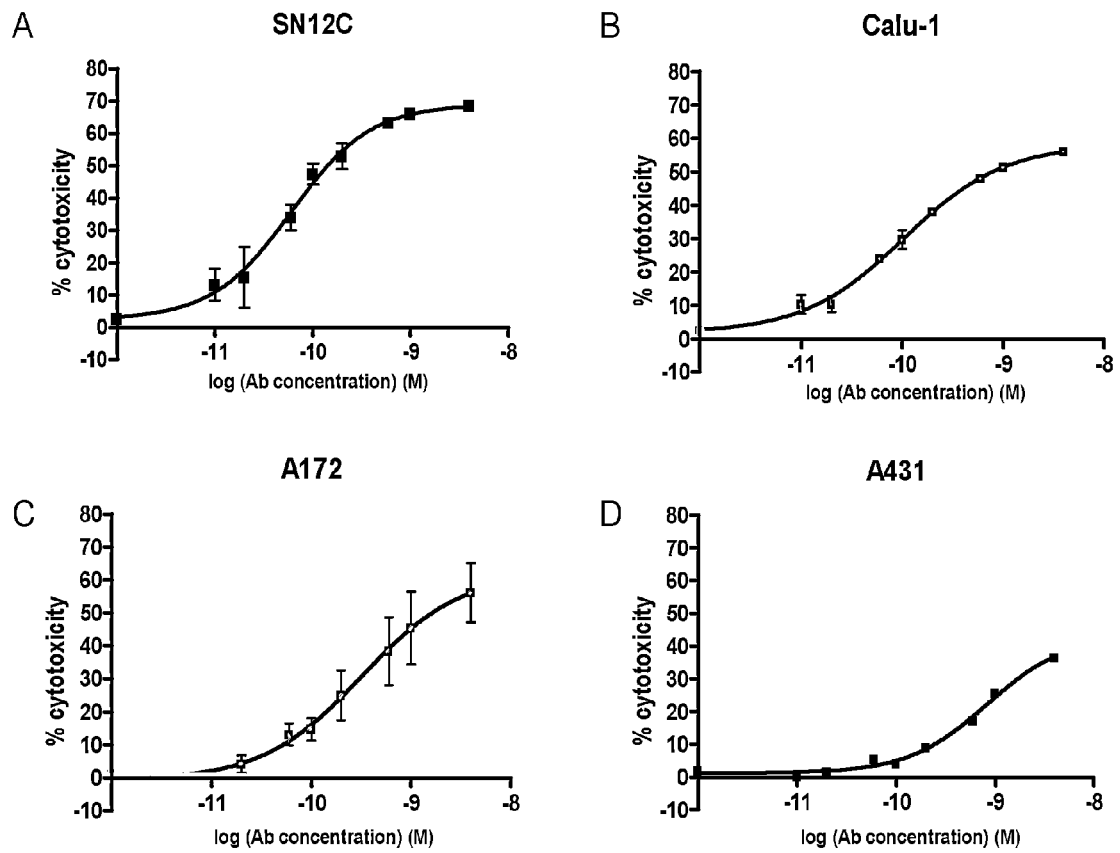

FIG. 10: Effect of 1613F12 on in vitro SN12C cells proliferation compared to the effect of the mIgG1 isotype control antibody.

FIGS. 11A-11K: Direct cytotoxicity assays of the 1613F12-saporin immunoconjugate using various human tumor cell lines. A-SN12C, B-Calu-1, C-A172, D-A431, E-DU145, F-MDA-MB435S, G-MDA-MB231, H-PC3, I-NCI-H226, J-NCI-H125, K-Panc1.

Figure 12:
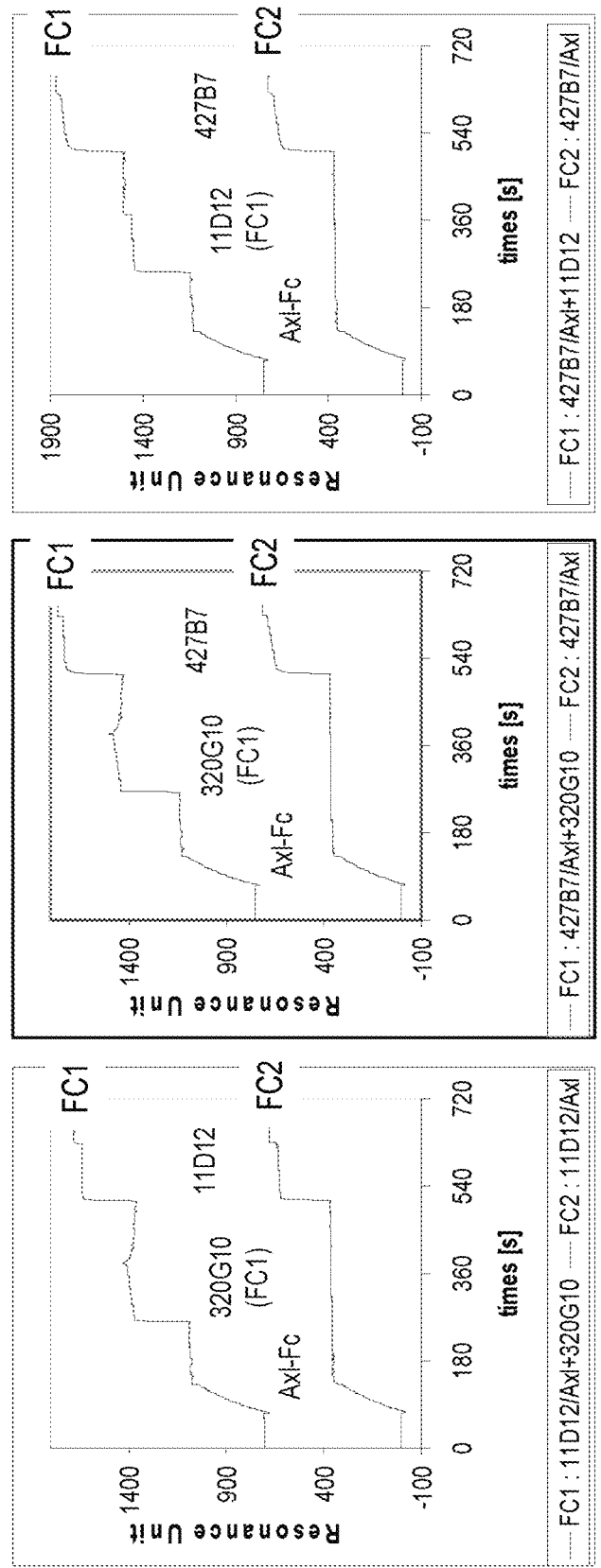

FIG. 12: Antibody binding competition between 427B7, 11D12 and 320G10 obtained by Biacore.

Figure 13:
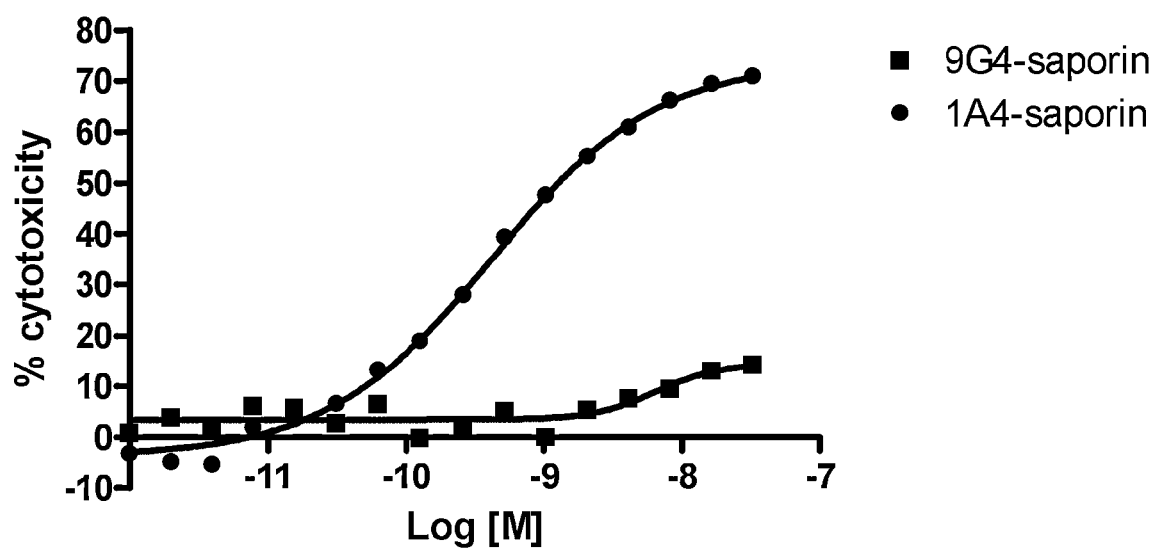

FIG. 13: Direct cytotoxicity assays using SN12C cells (in presence of 1A4-saporin immunoconjugate and an isotype control coupled to saporin).

EXAMPLES

Example 1

Axl Receptor Internalization

As an immunoconjugate approach is more efficient when the targeted antigen is an internalizing protein, Axl receptor internalization using Mab-Zap cytotoxicity assay on human tumor cell lines was studied. More precisely, the Mab-Zap reagent is a chemical conjugate including an affinity purified goat anti-mouse IgG and the ribosome-inactivating protein, saporin. If internalization of the immune complex occurs, saporin breaks away from the targeting agent and inactivates the ribosomes, resulting in protein synthesis inhibition and, ultimately, cell death. Cell viability determination after 72 hours of incubation with the anti-Axl antibody or with mIgG1 isotype control antibody on Axl-positive cells allows concluding on the anti-Axl antibody-induced Axl receptor internalization. For this study, several other murine anti-Axl antibodies were tested.

For this example highly Axl-positive cells, as determined using Qifikit reagent (Dako), were used. Data are presented in the following table 5.

TABLE 5

Antigen binding capacity of the MAB154 anti-Axl commercial antibody determined for the human renal cancer SN12C cells

| Cell line | RTK Antibody | AXL MAB154 |
|---|---|---|
| SN12C | | >100 000 |

In the following example, the SN12C cells were used as non limitative example. Any other cell line expressing appropriate level of Axl receptor on its cell surface could be used.

Concentration ranges of either the 1613F12 or any other tested murine anti-Axl antibody or the mIgG1 isotype control antibody were pre-incubated with 100 ng of Mab-Zap (Advanced targeting systems) secondary antibody in cell culture medium for 30 min at RT. These mixtures were loaded on sub-confluent SN12C cells plated in white 96-well plate microplate. Plates were incubated for 72 h at 37° C. in presence of 5% $CO_2$. Cell viability was determined using a Cell Titer Glo cell proliferation method according to the manufacturer's instructions (Promega). Several controls are performed: i) without any secondary immunoconjugate and ii) without primary antibody. In parallel, assays are performed with a mIgG1 isotype control.

Data obtained with the 1613F12 antibody are presented in the FIG. 1 and the data obtained with the other murine anti-Axl antibodies are presented in Table 6. The 1613F12 shows a maximal cytotoxic effect on the SN12C cells of ~36%. The percentages of maximum cytotoxicity obtained with other anti-Axl antibodies are listed in Table 6.

No cytotoxic effect was observed in presence of the 9G4 antibody, considered as mIgG1 isotype control in the experiment. No cytotoxicity was observed in wells containing only primary antibodies (data not shown).

Using different anti-Axl antibodies, maximal cytotoxicity percentages are comprised between 36.3% and 69% after 3 days of incubation with the antibodies.

Referring to the obtained cytotoxicity effect in this experiment, the Axl receptor appears to be a convenient antigen to target for an immunoconjugate approach as the various immune complexes comprising Axl-Axl anti-antibody-MabZap can trigger an effective cytotoxicity of the targeted cells.

Thus the Axl receptor appears to be a convenient antigen to target for an immunoconjugate approach as the immune complex comprising Axl-1613F12-MabZap, or all other anti-Axl antibodies of the invention, triggers an effective cytotoxicity of the targeted cells.

TABLE 6

Percentages of the maximum cytotoxicity obtained in indirect SN12C cytotoxicity assays

| | % cytotoxicity max |
|---|---|
| 1A4 | direct* |
| 11D12 | 54.2% |
| 320G10 | 41.4% |
| 427B7 | 36.3% |
| 517F1 | 66.5% |
| 530C8 | 50.2% |
| 534G9 | 49.9% |
| 535F7 | 55.6% |
| 547A1 | 69.0% |
| 1023F10 | 49.7% |
| 1614G5 | 65.1% |

*Axl antibody tested in direct in vitro SN12C cytotoxicity assay

Example 2

Generation of an Antibody Against rhAxl-ECD

Various strategies were used to generate murine antibodies targeting the human Axl extracellular domain.

The detailed protocol used to obtain the 1613F12 antibody is described bellow.

To generate murine monoclonal antibodies (Mabs) against human extracellular domain (ECD) of the Axl receptor, 5 BALB/c mice were immunized 5-times s.c. with 15-20.10$^6$ CHO-Axl cells and twice with 20 µg of the rh Axl-ECD. The first immunization was performed in presence of Complete Freund Adjuvant (Sigma, St Louis, Md., USA). Incomplete Freund adjuvant (Sigma) was added for following immunizations.

Three days prior to the fusion, immunized mice were boosted with both 20.10$^6$ CHO-Axl cells and 20 µg of the rhAxl-ECD with IFA.

To generate hybridomas, splenocytes and lymphocytes were prepared by perfusion of the spleen and by mincing of the proximal lymph nodes, respectively, harvested from 1 out of the 5 immunized mice (selected after sera titration) and fused to SP2/0-Ag14 myeloma cells (ATCC, Rockville, Md., USA). The fusion protocol is described by Kohler and Milstein (Nature, 256:495-497, 1975). Fused cells are then subjected to HAT selection. In general, for the preparation of monoclonal antibodies or their functional fragments, especially of murine origin, it is possible to refer to techniques which are described in particular in the manual "Antibodies" (Harlow and Lane, Antibodies: A Laboratory Manual, Cold Spring Harbor Laboratory, Cold Spring Harbor N.Y., pp. 726, 1988).

Approximately 10 days after the fusion, colonies of hybrid cells were screened. For the primary screen, supernatants of hybridomas were evaluated for the secretion of Mabs raised against the Axl ECD protein using an ELISA. In parallel, a FACS analysis was performed to select Mabs able to bind to the cellular form of Axl present on the cell surface of both wt CHO and Axl expressing CHO cells (ATCC).

As soon as possible, selected hybridomas were cloned by limit dilution and subsequently screened for their reactivity against the Axl ECD protein. Cloned Mabs were then isotyped using an Isotyping kit (cat #5300.05, Southern Biotech, Birmingham, Ala., USA). One clone obtained from each hybridoma was selected and expanded. Once produced the anti-Axl antibodies were further studied for their ability to be internalized following Axl binding on the cell-surface. In parallel, the hybridomas are deposited at the CNCM.

ELISA assays are performed as followed either using pure hybridoma supernatant or, when IgG content in supernatants was determined, titration was realized starting at 5 µg/ml. Then a ½ serial dilution was performed in the following 11 rows. Briefly, 96-well ELISA plates (Costar 3690, Corning, N.Y., USA) were coated 50 µl/well of the rh Axl-Fc protein (R and D Systems, cat N° 154-AL) or rhAxl-ECD at 2 µg/ml in screened by ELISA for their binding specificity for the extracellular domain of the rh Axl-ECD protein. Three clones of each code were expanded and isotyped. Once produced the anti-Axl antibodies were further studied for their ability to be internalized following Axl binding on the cell-surface.

The protocols applied to give rise to the other anti-Axl antibodies are summarized in Table 7.

TABLE 7

Immunization protocols

| Injections | Immunogen | Site of injection | Organ source | Hybridoma screen | Antibody |
|---|---|---|---|---|---|
| 3-5 immunizations + 1 boost (i.v or i.p.) | 5-20 µg of rh Axl protein (monomeric or dimeric) | s.c. | spleen proximal lymph nodes | ELISA rhAxl FACS DU145 | 1A4, 320G10, 11D12, 517F1, 530C8, 534G9, 535F7, 547A1, 427B7, 1023F10 |
| 5 immunizations 2 immunization + 1 boost (i.v or i.p.) | 15-20 $10^6$ CHO-Axl cells 20 µg rhAxl protein | s.c. | spleen proximal lymph nodes | ELISA rh Axl FACS CHO Axl/CHO wt | 1613F12 1614G5 |

PBS overnight at 4° C. The plates were then blocked with PBS containing 0.5% gelatin (#22151, Serva Electrophoresis GmbH, Heidelberg, Germany) for 2 h at 37° C. Once the saturation buffer discarded by flicking plates, 50 µl of pure hybridoma cell supernatants or 50 µl of a 5 µg/ml solution were added to the ELISA plates and incubated for 1 h at 37° C. After three washes, 50 µl horseradish peroxidase-conjugated polyclonal goat anti-mouse IgG (#115-035-164, Jackson Immuno-Research Laboratories, Inc., West Grove, Pa., USA) was added at a 1/5000 dilution in PBS containing 0.1% gelatin and 0.05% Tween 20 (w:w) for 1 h at 37° C. Then, ELISA plates were washed 3-times and the TMB (#UP664782, Uptima, Interchim, France) substrate was added. After a 10 min incubation time at room temperature, the reaction was stopped using 1 M sulfuric acid and the optical density at 450 nm was measured.

For the selection by flow cytometry, $10^5$ cells (CHO wt or CHO-Axl) were plated in each well of a 96 well-plate in PBS containing 1% BSA and 0.01% sodium azide (FACS buffer) at 4° C. After a 2 min centrifugation at 2000 rpm, the buffer was removed and hybridoma supernatants or purified Mabs (1 µg/ml) to be tested were added. After 20 min of incubation at 4° C., cells were washed twice and an Alexa 488-conjugated goat anti-mouse antibody 1/500° diluted in FACS buffer (#A11017, Molecular Probes Inc., Eugene, USA) was added and incubated for 20 min at 4° C. After a final wash with FACS buffer, cells were analyzed by FACS (Facscalibur, Becton-Dickinson) after addition of propidium iodide to each tube at a final concentration of 40 ng/ml. Wells containing cells alone and cells incubated with the secondary Alexa 488-conjugated antibody were included as negative controls. Isotype controls were used in each experiment (Sigma, ref M90351MG). At least 5000 cells were assessed to calculate the mean value of fluorescence intensity (MFI).

More precisely, the fusion was performed with $300.10^6$ of harvested splenocytes and $300.10^6$ myeloma cells (1:1 ratio). Two hundred thousand cells of the resulting cell suspension were then plated at $2.10^6$ cell/ml in 30 96-well plates.

A first screen (around Day 14 after fusion) both by ELISA on the rhAxl-ECD protein and by FACS analysis using the both wt CHO and Axl expressing CHO cells allowed to select 10 hybridomas presenting optical densities (ODs) above 1 on the rh Axl-ECD coating and MFI bellow 50 on wt CHO cells and above 200 on CHO-Axl cells.

These 10 hybridomas were expanded and cloned by limit dilution. One 96-well plate was prepared for each code. Nine days after plating, supernatants from cloning plates were first Moreover, the isotype of the anti-Axl antibodies are given in the following Table 8.

In addition, the epitope diversity of the obtained Axl antibodies was assessed by antibody binding competition. Epitope clustering experiments were run out on a Biacore X device. This instrument based on the optical phenomenon of surface plasmon resonance (SPR) enables the detection and measurement of protein-protein interactions in real time, without any labelling.

Briefly, the experiments were realized using a sensor chip CM5 as the biosensor. An anti-polyhistidine mouse IgG1 antibody (R and D Systems, MAB050) was coupled on both flow cells (FC1 and FC2) using amine coupling chemistry.

The experiments were carried out at a flow rate of 10-20 µl/min in a HBS-EP buffer at 25° C. The recombinant hAxl-Fc chimera protein (R and D Systems, 154-AL-100) was injected during one minute at the concentration of 5-10-20 µg/ml on both flowcells. Typically, this injection captured between 300 to 500 RU of protein. A first antibody (culture supernatant or purified antibody at the concentration of 50 µg/ml) is injected on the flowcell 1 during 1-2 min. in order to reach a saturation of the captured antigen. The second antibody was the injected on both flowcells (culture supernatant or purified antibody at the concentration of 50 µg/ml) during 60 s. Both antibodies are classed in the same epitopic group when the signal of the second antibody on the flowcell 1 is at least 10 times lower than the response on the flowcell 2.

At the end of each cycle, the surfaces are regenerated by injecting a 10 mM glycine hydrochloride pH 1.5 solution during 30 s.

The epitopic group of the anti-Axl antibodies is precised in Table 8.

Examples of Biacore data are reported in FIG. 12 which illustrates the competition between 427B7, 11D12 and 320G10. The same way of analysis was applied for the other anti-Axl antibodies of the invention.

TABLE 8

Isotype and Epitopic group of the Axl antibodies.

| | Isotype | Epitopic group | CNCM |
|---|---|---|---|
| 1A4 | IgG1 K | group #B | I-3947 |
| 11D12 | IgG1 K | group #B | I-4116 |
| 320G10 | IgG1 K | group #C | I-4514 |

TABLE 8-continued

Isotype and Epitopic group of the Axl antibodies.

| | Isotype | Epitopic group | CNCM |
|---|---|---|---|
| 427B7 | IgG1 K | group #A | I-4518 |
| 517F1 | IgG1 K | group #B | I-4502 |
| 530C8 | IgG1 K | group #B1 | I-4728 |
| 534G9 | IgG1 K | group #B2 | I-4729 |
| 535F7 | IgG1 K | group #B | I-4510 |
| 547A1 | IgG1 K | group #B | I-4506 |
| 1023F10 | IgG1 K | group #B | I-4507 |
| 1613F12 | IgG1 K | group #B | I-4505 |
| 1614G5 | IgG1 K | group #A | I-4519 |

They spread over 5 epitopic clusters.

Example 3

Axl Binding Specificity

In this example, the binding of the anti-Axl antibodies was first studied on the rhAxl-Fc protein. Then, their binding on the two other members of the TAM family, rhDtk-Fc and rhMer-Fc, was studied.

Briefly, the recombinant human Axl-Fc (R and D systems, cat N° 154AL/CF), rhDtk (R and D Systems, cat N° 859-DK) or rhMer-Fc (R and D Systems, cat N° 891-MR) proteins were coated overnight at 4° C. to Immulon II 96-well plates and, after a 1 h blocking step with a 0.5% gelatine solution, purified anti-Axl antibodies were added for an additional 1 h at 37° C. at starting concentration of 5 µg/ml ($3.33 \times 10^{-8}$M). Then ½ serial dilutions were done over 12 columns. Plates were washed and a goat anti-mouse (Jackson) specific IgG-HRP was added for 1 h at 37° C. Reaction development was performed using the TMB substrate solution. The commercial anti-Axl Mab 154 antibody was also used in parallel (data not shown). Coating controls were performed in presence of a goat anti-human IgG Fc polyclonal serum labelled with HRP (Jackson, ref 109-035-098) and/or in presence of a HRP-coupled anti-Histidine antibody (R and D Systems, ref: MAB050H). No non specific binding was observed in absence of primary antibody (diluant). Results obtained with the 1613F12 antibody are graphically represented in FIGS. 2A, 2B and 2C, respectively. Data obtained for the other anti-Axl antibodies are reported in the Table 9.

TABLE 9

Binding specificty of the Axl antibodies assessed by ELISA using human recombinant proteins*

| | rhAxl-Fc | rhMer-Fc | rhDtk-Fc |
|---|---|---|---|
| 1A4 | 2.816 | 0.298 | 0.142 |
| 11D12 | 2.994 | 0.281 | 0.104 |
| 320G10 | 2.737 | 0.287 | 0.107 |
| 427B7 | 2.840 | 0.284 | 0.144 |
| 517F1 | 2.862 | 0.300 | 0.112 |
| 530C8 | 2.712 | 0.250 | 0.115 |
| 534G9 | 2.629 | 0.226 | 0.108 |
| 535F7 | 2.721 | 0.235 | 0.115 |
| 547A1 | 2.691 | 0.227 | 0.099 |
| 1023F10 | 2.676 | 0.247 | 0.114 |
| 1613F12 | 2.806 | 0.252 | 0.121 |
| 1614G5 | 2.592 | 0.275 | 0.122 |

*Values of ODs (450 nm) obtained in presence of a 5 µg/ml concentration of Axl antibody are reported here.

This example shows that the 1613F12 antibody only binds to the rhAxl-Fc protein and does not bind on the two other members of the TAM family, rhDtk or rhMer. No cross-specificity of binding of the 1613F12 antibody is observed between TAM members. Similar results are observed for all the other tested anti-Axl antibodies. Indeed, they present a specificity of binding restricted to Axl; they do not recognize the other members of the TAM family.

Example 4

1613F12 and Other Anti-Axl Antibodies Recognized the Cellular Form of Axl Expressed on Tumor Cells Cell surface Axl expression level on human tumor cells was first established using a commercial Axl antibody (R and D Systems, ref: MAB 154) in parallel of calibration beads to allow the quantification of the Axl expression level. Then, binding of the cell-surface Axl was studied using the anti-Axl antibodies of the invention. In both cases, the experimental conditions were as briefly described bellow.

For cell surface binding studies, two fold serial dilutions of a 10 µg/ml ($6.66 \times 10^{-8}$ M) primary antibody solution (anti-Axl antibodies, MAB154 anti-Axl commercial antibody or mIgG1 isotype control 9G4 Mab) are prepared on 10 points and applied on $2.10^5$ cells for 20 min at 4° C. After 3 washes in phosphate-buffered saline (PBS) supplemented with 1% BSA and 0.01% $NaN_3$, cells were incubated with the secondary Goat anti-mouse Alexa 488 antibody (1/500° dilution) for 20 minutes at 4° C. After 3 additional washes in PBS supplemented with 1% BSA and 0.1% $NaN_3$, cells were analyzed by FACS (FACS, Becton-Dickinson). At least 5000 cells were assessed to calculate the mean value of fluorescence intensity.

For quantitative ABC determination using the MAB154 Axl antibody, QIFIKIT® calibration beads are used. In parallel with the QIFIKIT® beads, cells are incubated, with a Polyclonal Goat Anti-Mouse Immunoglobulins/FITC (Goat F(ab')$_2$) at a saturating concentration. The number of antigenic sites on the studied cells is then determined by interpolation of the calibration curve (the fluorescence intensity of the individual bead populations against the number of Mab molecules on the beads).

4.1. Quantification of Cell-Surface Axl Expression Level

Axl expression level on the surface of human tumor cells was determined by flow cytometry using indirect immunofluorescence assay (QIFIKIT® method (Dako, Denmark), a quantitative flow cytometry kit for assessing cell surface antigens. A comparison of the mean fluorescence intensity (MFI) of the known antigen levels of the beads via a calibration graph permits determination of the antibody binding capacity (ABC) of the cell lines.

Table 10 presents Axl expression level detected on the surface of various human tumor cell lines (SN12C, Calu-1, A172, A431, DU145, MDA-MB435S, MDA-MB231, PC3, NCI-H226, NCI-H125, MCF7, Panc1) (ATCC, NCI) as determined using QIFIKIT® using the Axl commercial antibody MAB154 (R and D Systems). Values are given as Antigen Binding Complex (ABC).

TABLE 10

| | MCF7 | NCI-H125 | MDA-MB-435S | Panc1 | MDA-MB-231 | Calu-1 | SN12C |
|---|---|---|---|---|---|---|---|
| Tumor type/organ | Breast | NSCLC | Breast | Pancreas | Breast | Lung | Renal |
| ABC (Qifikit) | 71 | 5 540 | 17 814 | 36 809 | 61 186 | >100 000 | >100 000 |

| | A172 | A431 | DU-145 | PC3 | NCI-H226 |
|---|---|---|---|---|---|
| Tumor type/organ | glioblastoma | Epidermoid carcinoma | Prostate | prostate | NSCLC |
| ABC (Qifikit) | 52421 | 3953 | 55268 | 8421 | 32142 |

Results obtained with a commercial Axl monoclonal antibody (MAB154) showed that Axl receptor is expressed at various levels depending of the considered human tumor cell.

4.2. Axl Detection by 1613F12 and Anti-Axl Antibodies According to the Invention on Human Tumor Cells Axl binding obtained using the 1613F12 was studied more extensively on a panel of different human tumor cells. Data are graphically presented in FIG. 3.

The binding of the other anti-Axl antibodies was documented using the SN12C human renal tumor cells only.

Anti-Axl antibody dose response curves were run. MFIs obtained with the 1613F12 antibody using the various human tumor cells were then analysed with Prism software. Data obtained with the 1613F12 are presented in FIG. 3. The $EC_{50}$ of the binding on SN12C cells obtained for the other tested anti-Axl antibodies are reported in Table 11.

TABLE 11

Binding of the Axl antibodies on SN12c cells studied by flow cytometry

| | $EC_{50}$ SN12C binding (M) |
|---|---|
| 1A4 | 1.E-09 |
| 11D12 | 2.E-10 |
| 320G10 | 4.E-10 |
| 427B7 | 5.E-10 |
| 517F1 | 7.E-10 |
| 530C8 | 1.E-09 |
| 534G9 | 4.E-10 |
| 535F7 | 8.E-11 |
| 547A1 | 2.E-10 |
| 1023F10 | 1.E-09 |
| 1614G5 | 9.E-10 |

As illustrated in FIG. 3, data indicate that the 1613F12 binds specifically to the membrane Axl receptor as attested by the saturation curve profiles. Similar profiles were obtained with the other tested antibodies (data not shown). The values of the $EC_{50}$ of anti-Axl antibody binding on SN12C cells are comprised between $10^{-9}$M and $10^{-12}$ M.

Example 5

1613F12 Inter-Species Crosspecificity

To address the species cross-specificity of the 1613F12, two species were considered: mouse and monkey. First the binding on the recombinant mouse (rm) Axl receptor is studied by ELISA (FIG. 4). Then flow cytometry experiments were performed using monkey COS7 cells as these cells express the Axl receptor on their surface (FIG. 5). The COS7 cell line was obtained by immortalizing a CV-1 cell line derived from kidney cells of the African green monkey with a version of the SV40 genome that can produce large T antigen but has a defect in genomic replication.

rmAxl-Fc ELISA

Briefly, the recombinant mouse Axl-Fc (R and D systems, cat N° 854-AX/CF) proteins were coated overnight at 4° C. to Immulon II 96-well plates and, after a 1 h blocking step with a 0.5% gelatine solution, the 1613F12 purified antibody was added for one additional hour at 37° C. at starting concentration of 5 µg/ml (3.33 $10^{-8}$M). Then ½ serial dilutions were done over 12 columns. Plates were then washed and a goat anti-mouse (Jackson) specific IgG HRP was added for 1 h at 37° C. Reaction development was performed using the TMB substrate solution. The commercial mouse anti-Axl Mab 154 antibody is also used in parallel. Coating controls are performed in presence of a goat anti-human IgG Fc polyclonal serum coupled with HRP (Jackson, ref 109-035-098) and/or in presence of a HRP-coupled anti-Histidine antibody (R and D Systems, ref: MAB050H). No specific binding is observed in the absence of primary antibody (diluant).

Results are represented in FIG. 4. This figure shows that the 1613F12 Mab described in the present invention does not bind to the murine Axl ECD domain.

FACS COS7

For 1613F12 cellular binding studies using COS7 cells, $2.10^5$ cells were incubated with an antibody concentration range prepared by ½ serial dilution (12 points) of a 10 µg/ml (6.66 $10^{-8}$ M) antibody solution of 1613F12 or m9G4 (mIgG1 isotype control Mab) for 20 min at 4° C. After 3 washes in phosphate-buffered saline (PBS) supplemented with 1% BSA and 0.01% $NaN_3$, cells were incubated with secondary antibody goat anti-mouse Alexa 488 (dilution 1/500) for 20 minutes at 4° C. After 3 additional washes in PBS supplemented with 1% BSA and 0.1% $NaN_3$, cells were analyzed by FACS (Facscalibur, Becton-Dickinson). At least 5000 cells were assessed to calculate the mean value of fluorescence intensity. Data are analyzed using Prism software.

Results are represented in FIG. 5. The titration curve established on COS7 cells using either 1613F12 or mIgG1 isotype control confirms that 1613F12 is able to recognize the monkey cellular form of the Axl receptor expressed on the surface of the COS7 cells. Plateau is reached for 1613F12 concentrations above 0.625 µg/ml (4.2 $10^{-10}$ M). As expected no binding is observed in presence of the mIgG1 isotype control.

This example illustrates the fact that the 1613F12 does not cross-react with the mouse Axl receptor. In contrast it strongly binds to the monkey Axl receptor expressed on the surface of COST cells.

Example 6

Gas6 Competition Experiments Performed in Presence of the 1613F12

To further characterize the anti-Axl Mabs, Gas6 competition assays were performed. In this assay, the free rhAxl-Fc protein and the anti-Axl antibody are incubated to form antigen-antibody complex and then the complexes are loaded on Gas6-coated surface in the assay plate. The unbound antibody-antigen complexes are washed out before adding enzyme-linked secondary antibody against the human Fc portion of the rhAxl-Fc protein. The substrate is then added and the antigen concentration can be determined by the signal strength elicited by the enzyme-substrate reaction.

Briefly reaction mixture comprising the rhAxl-Fc protein in the presence or not of the anti-Axl Mabs to be tested, are prepared on a separate saturated (0.5% gelatin in PBS 1×) plate. Serial 1:2 dilutions (starting from 80 µg/ml on 12 columns) of murine anti-Axl antibodies are performed. Then 0.5 µg/ml of the rhAxl-Fc protein is added (R and D Systems, ref 154AL/CF), except to the negative control line that contains only ELISA diluant (0.1% gelatin, 0.05% Tween 20 in PBS 1×). After homogenisation, the competition samples are loaded on Gas6-coated plates with a 6 µg/ml rhGas6 solution in PBS (R and D systems cat N° 885-GS-CS/CF). After incubation and several washes, bound rhAxl-Fc proteins are detected using a goat anti-Human IgG-HRP (Jackson, ref 109-035-098). Once bound, the TMB substrate is added to the plates. The reaction is stopped by addition of 1M $H_2SO_4$ acid solution and the obtained optical densities read at 450 nm using a microplate reader instrument.

This experiment (FIG. 6) shows that the 1613F12 is able to compete with the rhAxl-Fc binding on its immobilized ligand. Competition with Gas6 binding occurs in presence of 1613F12 antibody concentrations above 2.5 µg/ml ($1.67\ 10^{-8}$ M). No more binding of the rhAxl-Fc on the immobilized Gas6 is observed in presence of a 1613F12 concentration above 10 µg/ml ($6.67\ 10^{-8}$ M). The 1613F12 blocks Gas6 binding to rhAxl-Fc.

Example 7

Epitope Recognition by Western Blot

To determine if the 1613F12 recognizes a linear or a conformational epitope, western blot analysis was done using SN12C cell lysates. Samples were differently treated to be in reducing or non reducing conditions. If a band is visualized with reduced sample, the tested antibody targets a linear epitope of the ECD domain; If not, it is raised against a conformation epitope of the Axl ECD.

SN12C cells were seeded in RPMI+10% heat inactivated FBS+2 mM L-glutamine at $5.10^4$ cells/cm² in T162 cm² flasks for 72 h at 37° C. in a 5% $CO_2$ atmosphere. Then the cells were washed twice with phosphate buffered saline (PBS) and lysed with 1.5 ml of ice-cold lysis buffer [50 mM Tris-HCl (pH7.5); 150 mM NaCl; 1% Nonidet P40; 0.5% deoxycholate; and 1 complete protease inhibitor cocktail tablet plus 1% antiphosphatases]. Cell lysates were shaken for 90 min at 4° C. and cleared at 15000 rpm for 10 min. Protein concentration was quantified using BCA. Various samples were loaded. First 10 µg of whole cell lysate (10 µg in 20 µl) were prepared in reducing conditions (1× sample buffer (BIORAD)+1× reducing agent (BIORAD)) and loaded on a SDS-PAGE after 2 min incubation at 96° C. Secondly two other samples of 10 µg of whole cell lysate were prepared in non-reducing conditions (in 1× sample buffer (BIORAD) only). Prior to be loaded on the SDS-PAGE gel, one of these two last samples is heated 2 min incubation at 96° C.; the other one is kept on ice. After migration, the proteins are transferred to nitrocellulose membrane. Membranes were saturated for 1 h at RT with TBS-tween 20 0.1% (TBST), 5% non-fat milk and probed with the 1613F12 at 10 µg/ml overnight at 4° C. Antibodies were diluted in Tris-buffered saline-0.1% tween 20 (v/v) (TBST) with 5% non-fat dry milk. Then membranes were washed with TBST and incubated with peroxydase-conjugated secondary antibody (dilution 1/1000) for 1 h at RT. Immunoreactive proteins were visualized with ECL (Pierce #32209). After Axl visualization, membranes were washed once again with TBST and incubated for 1 h at RT with mouse anti-GAPDH antibody (dilution 1/200 000). Then membranes were washed in TBST and incubated with peroxydase-conjugated secondary antibodies, for 1 h at RT. Membranes were washed and GAPDH was revealed using ECL.

Results are represented in FIG. 7.

The 1613F12 mainly recognizes a conformational epitope as a specific band is essentially observed in non-reduced conditions. However a faint signal is detected in the denaturating migrating condition of the SN12C cell lysate indicating 1613F12 is able to weakly bind to a linear epitope.

Example 8

Measurement of Axl Down-Regulation Triggered by the 1613F12 and Other Anti-Axl Antibodies by Western Blot In the following example, the human renal cell carcinoma cell line SN12C (ATCC) was selected to address the activity of Axl antibodies on Axl receptor expression. The SN12C cell line overexpresses the Axl receptor. The Axl down-regulation was studied by Western-Blot on whole cell extracts.

SN12C cells were seeded in RPMI+10% heat inactivated FBS+2 mM L-glutamine at $6.10^4$ cells/cm² in six-well plates for 48 h at 37° C. in a 5% $CO_2$ atmosphere. After two washes with phosphate buffer saline (PBS), cells were serum-starved in a medium containing either 800 ng/ml recombinant mouse gas6 ligand (R and D Systems, ref: 986-GS/CF) or 10 µg/ml of a mIgG1 isotype control antibody (9G4) or 10 µg/ml of the Axl antibody of the present invention and incubated for 4 h or 24 additional hours. Then the medium was gently removed and cells washed twice with cold PBS. Cells were lysed with 200 µl of ice-cold lysis buffer [50 mM Tris-HCl (pH7.5); 150 mM NaCl; 1% Nonidet P40; 0.5% deoxycholate; and 1 complete protease inhibitor cocktail tablet plus 1% antiphosphatases]. Cell lysates were shaken for 90 min at 4° C. and cleared at 15 000 rpm for 10 min. Protein concentration was quantified using BCA method. Whole cell lysates (10 µg in 20 µl) were separated by SDS-PAGE and transferred to nitrocellulose membrane. Membranes were saturated for 1 h at RT with TBS-Tween 20 0.1% (TBST), 5% non-fat milk and probed with a commercial M02 Axl antibody at 0.5 µg/ml (AbNova H00000558-M02) overnight at 4° C. Antibodies were diluted in Tris-buffered saline-0.1% tween 20 (v/v) (TBST) with 5% non-fat dry milk. Then membranes were washed with TBST and incubated with peroxydase-conjugated secondary antibody (dilution 1/1000) for 1 h at RT. Immunoreactive proteins were visualized with ECL (Pierce #32209). After Axl visualization, membranes were washed once again with TBST and incubated for 1 h at RT with mouse anti-GAPDH antibody (dilution 1/200000). Then membranes were washed in TBST and incubated with peroxydase-conjugated secondary antibodies, for 1 h at RT. Membranes were washed and GAPDH was revealed using ECL. Band intensity was quantified by densitometry.

Experimental data describing the effect of the isotype control, rmGas6 and the 1613F12 antibody are provided in FIGS. 8A-8B. They are representative of 3 independent experiments. Then the percentage of downregulated Axl receptor in the SN12C cell extract at 24 h obtained in presence of other Axl antibodies is given in Table 12.

The results show that 1613F12 is able to down-regulate Axl in an Axl-overexpressing human tumor cell line. At 4 h, the 1613F12 triggers a 66% Axl down-regulation, and up to 87% after a 24 hour incubation with the 1613F12. For the other tested anti-Axl antibodies, the percentage of downregulated Axl in SN12C cells after a 24 h incubation of Axl antibody is comprised between 48.7% and 89%.

TABLE 12

Axl downregulation after Axl antibody binding on SN12C cells studied by Western Blot

|  | % downregulated Axl at 24 h |
|---|---|
| 1A4 | 69.0 |
| 11D12 | 64.4 |
| 320G10 | 71.0 |
| 427B7 | 62.0 |
| 517F1 | 68.0 |
| 530C8 | 48.7 |
| 534G9 | 64.5 |
| 535F7 | 80.0 |
| 547A1 | 80.0 |
| 1023F10 | 70.0 |
| 1614G5 | 63.0 |

Example 9

Flow Cytometry Study of the 1613F12 and Other Anti-Axl Antibodies Effect on Cell Surface Axl Expression Flow cytometry technique allows labelling of cell-surface Axl receptor. The use of this technique can highlight the effect of antibody on the membrane Axl expression. Human renal tumor SN12C cells that express high levels of Axl were used in this example.

SN12C tumor cell line was cultured in RMPI1640 with 1% L-glutamine and 10% of FCS for 3 days before experiment. Cells were then detached using trypsin and plated in 6-multiwell plate in RPMI1640 with 1% L-glutamine and 5% FBS. The next day, antibodies of interest were added at 10 μg/ml. Untreated wells were also included. The cells are incubated at 37° C., 5% $CO_2$. Twenty four hours later, cells were washed with PBS, detached and incubated with the same antibodies of interest in FACS buffer (PBS, 1% BSA, 0.01% sodium azide). Untreated wells were also stained with the same antibody in order to compare the signal intensity obtained with the same Mab on the treated and the non-treated cells. Cells were incubated for 20 minutes at 4° C. and washed three times with FACS buffer. An Alexa 488-labeled goat anti-mouse IgG antibody was incubated for 20 minutes and cells were washed three times before FACS analysis on propidium iodide negative cell population.

Two parameters are determined: (i) the difference of the fluorescent signal detected on the surface of untreated (no Ab) cells compared to the Ab-treated cells at T24 h and (ii) the percentage of remaining Axl on the cell surface. The percentage of remaining Axl is calculated as follows:

% remaining $Axl = (MFI_{Ab\ 24\ h}/MFI_{no\ Ab\ 24\ h}) \times 100$

Data from one representative experiment (out of 3) are presented in Table 13a. The results were reproduced in three independent experiments.

The difference of MFI between the staining of a Mab in the untreated cell and the treated condition with the same antibody reflects a down-regulation of the Axl protein on the cell surface of the cells due to the binding of the considered Mab. Conditions without antibody gave similar results to conditions in presence of the isotype control antibody (m9G4).

TABLE 13a

| Labelling | Treatment | MFI at T24 h | Δ ($MFI_{No\ Ab\ 24\ h}$ − $MFI_{Ab\ 24\ h}$) | % remaining Axl |
|---|---|---|---|---|
| 1613F12 | No Ab | 938 | 514 | 45.2 |
|  | 1613F12 | 424 |  |  |
| 9G4 | No Ab | 11 | −2 | 117 |
|  | 9G4 | 13 |  |  |
| MAB154 | No Ab | 950 | ND | ND |
|  | 9G4 | ND |  |  |

The data demonstrate that the mean fluorescence intensity detected on the surface of the cells treated with 1613F12 for 24 hours is reduced (−514) compared to the MFIs obtained with untreated cells labelled with the 1613F12. After a 24 h incubation with the 1613F12 antibody, 45.2% of the cell-surface Axl receptor remains at the SN12C cell-surface.

Data obtained with other anti-Axl antibodies are presented in Table 13b.

TABLE 13b

Antibody internalization study by flow cytometry usnig SN12C cells

|  | ΔMFI |
|---|---|
| 1A4 | 497 |
| 11D12 | 438 |
| 320G10 | 355 |
| 427B7 | 256 |
| 517F1 | 303 |
| 530C8 | 334 |
| 534G9 | 257 |
| 535F7 | 352 |
| 547A1 | 473 |
| 1023F10 | 380 |
| 1614G5 | 305 |

Example 10

Anti-Axl Antibodies Internalization Study Using Fluorescent Immunocytochemistry Labelling Complementary internalization results are obtained by confocal microscopy using indirect fluorescent labelling method.

Briefly, SN12C tumor cell line was cultured in RMPI1640 with 1% L-glutamine and 10% of FCS for 3 days before experiment. Cells were then detached using trypsin and plated in 6-multiwell plate containing coverslide in RPMI1640 with 1% L-glutamine and 5% FCS. The next day, the anti-Axl antibody was added at 10 μg/ml. Cells treated with an irrelevant antibody were also included. The cells were then incubated for 1 h and 2 h at 37° C., 5% $CO_2$. For T 0 h, cells were incubated for 30 minutes at 4° C. to determine antibody binding on cell surface. Cells were washed with PBS and fixed with paraformaldehyde for 15 minutes. Cells were rinsed and incubated with a goat anti-mouse IgG Alexa 488 antibody for 60 minutes at 4° C. to identify remaining antibody on the cell surface. To follow antibody penetration into the cells, cells were fixed and permeabilized with saponin. A goat anti-mouse IgG Alexa 488 (Invitrogen) was used to stained both the membrane and the intracellular antibody. Early endosomes were identified using a rabbit polyclonal antibody against EEA1 revealed with a goat anti-rabbit IgG-Alexa 555 antibody (Invitrogen). Cells were washed three times and nuclei were stained using Draq5. After staining, cells were mounted in Prolong Gold mounting medium (Invitrogen) and analyzed by using a Zeiss LSM 510 confocal microscope.

Photographs are presented in FIGS. 9A-9C.

Images were obtained by confocal microscopy. In presence of the mIgG1 isotype control (9G4), neither membrane staining nor intracellular labelling is observed (FIG. 9A). A progressive loss of the membrane anti-Axl labelling is observed as soon as after 1 h incubation of the SN12C cells with the 1613F12 (FIG. 9B). Intracellular accumulation of the 1613F12 Axl antibody is clearly observed at 1 h and 2 h (FIG. 9C). Intracellular antibody co-localizes with EEA1, an early endosome marker. These photographs confirm the internalization of the 1613F12 into SN12C cells.

Example 11

In Vitro Anti-Axl Mediated Anti-Tumoral Activity

SN12C Proliferation Assay

Ten thousand SN12C cells per well were seeded in FCS-free medium on 96 well plates over night at 37° C. in a 5% $CO_2$ atmosphere. The next day, cells were pre-incubated with 10 µg/ml of each antibody for 1 h at 37° C. Cells were treated with or without rmGas6 (R and D Systems, cat N° 986-GS/CF), by adding the ligand directly to the well, and then left to grown for 72 h. Proliferation was measured following $^3H$ thymidine incorporation.

Data are presented in FIG. 10. No effect was observed with the 1613F12 which is silent when added to SN12C cells.

Example 12

Cytotoxicity Potency of 1613F12-Saporin and of 1A4-Saporin Immunoconjugates in Various Human Tumor Cell Line In the present example, is first documented the cytotoxicity potency of the saporin coupled-1613F12. For this purpose direct in vitro cytotoxicity assays using a large panel of human tumor cell lines were performed (FIGS. 11A-11K). This tumor cell line panel offers various Axl expression levels. Secondly, is evaluated another anti-Axl targeting immunoconjugate, 1A4-saporin for its direct cytotoxic effect on human SN12C renal tumor cells (FIG. 13).

Briefly, 5000 cells were seeded in 96 well culture plates in 100 µl of 5% FBS adequate culture medium. After 24 hour incubation in a 5% $CO_2$ atmosphere at 37° C., a range of concentrations of the anti-Axl antibody or the immunoconjugate (anti-Axl antibody-saporin or 9G4-saporin or the naked anti-Axl antibody or 9G4) is applied to the cells. The immunoconjugates were used in a large range of concentrations. Culture plates are then incubated at 37° C. in a humidified 5% $CO_2$ incubator for 72 hours.

At D4, the cell viability is assessed using the CellTiter-Glo® Luminescent Cell Viability kit (Promega Corp., Madison, Wis.) that allows determining the number of viable cells in culture based on quantification of the ATP present, an indicator of metabolically active cells. Luminescent emissions are recorded by a luminometer device.

From luminescence output is calculated the percentage of cytotoxicity using the following formula:

% cytotoxicity=100−[($RLU_{Ab-sap}$×100)/$RLU_{No\ Ab}$]

On FIGS. 11A-11K are put together graphs presenting cytotoxicity percentage in function of the immunoconjugate concentration obtained in distinct in vitro cell cytotoxicity assays with (A) SN12C, (B) Calu-1, (C) A172, (D) A431, (E) DU145, (F) MDA-MB-4355, (G) MDA-MB-231, (H) PC3, (I) NCI-H226, (J) NCI-H125 or (K) Panc1 tumor cells treated with a range of 1613F12-saporin immunoconjugate concentrations.

FIGS. 11A-11K shows that the 1613F12-saporin immunoconjugate triggered cytotoxicity in these different human tumor cell lines. The potency of the resulting cytotoxicity effect depends on the human tumor cell line.

FIG. 13 presents the cytotoxicity activity triggered by the 1A4-saporin immunoconjugate using SN12C human renal cells. This Axl-targeting immunoconjugate exhibited a dose-dependent cytotoxic effect with a maximum cytotoxic effect of 71%, Example 13

Binding Kinetics of Axl Antibodies to Human Axl ECD

Affinity measurement of the 1613F12 was then determined using Biacore.

A Biacore X is used to measure the binding kinetics of Axl antibodies on human Axl ECD.

The instrument based on the optical phenomenon of surface plasmon resonance (SPR) used by Biacore systems enables the detection and measurement of protein-protein interactions in real time, without the use of labels.

Briefly, the experiments were realized using a sensor chip CM5 as the biosensor. Rabbit IgGs were immobilized on the flow cells 1 and 2 (FC1 and FC2) of a CM5 sensor chip at a level of 9300-10000 response units (RU) using amine coupling chemistry to capture antibodies.

Binding is evaluated using multiple cycles. Each cycle of measure is performed using a flow rate of 30 µl/min in a HBS-EP buffer. Then the Axl antibody to be tested is captured on the chip for 1 min on FC2 only to reach a mean capture value of 311.8 RU (SD=5.1 RU) for the 1613F12 antibody. The analyte (Axl ECD antigen) is injected starting at 200 nM and using two-fold serial dilutions to measure rough ka and kd in real time.

At the end of each cycle, the surfaces are regenerated by injecting a 10 mM glycine hydrochloride pH1.5 solution to eliminate the antibody-antigen complexes and the capture antibody as well. The considered signal corresponds to the difference of the signals observed between FC1 and FC2 (FC2-FC1). Association rates (ka) and dissociation rates (kd) were calculated using a one-to-one Langmuir binding model. The equilibrium dissociation constant (KD) is determined as the ka/kd ratio. The experimental values were analyzed in the Biaevaluation software version 3.0. A $\chi 2$ analysis will be performed to assess the accuracy of the data.

Data are summarized in the following Table 14.

TABLE 14

| Binding kinetics and affinity of 1613F12 to human Axl ECD | | | | |
|---|---|---|---|---|
| Antibody | Ka (1/Ms) | Kd(1/s) | KD (M) | Chi$^2$ |
| 1613F12 | 1.06 10$^5$ | 2.42 10$^{-4}$ | 2.29 10$^{-9}$ | 0.71 (0.6%) |

To produce the human extracellular domain (ECD) of Axl, the human cDNAs coding for the human soluble AXL receptor was first cloned into the pCEP4 expression vector by PCR. The purified product was then digested with restriction enzymes HindIII and BamHI and ligated into pCEP4 expression vector which had been precut with the same enzymes. Finally, the identified recombinant plasmid pCEP[AXL]His$_6$ was further confirmed by DNA sequencing.

Then suspension adapted cells HEK293E were cultivated in Ex-cell 293 (SAFC Biosciences) medium with 4 mM glutamine. All transfections were performed using linear 25 kDa polyethyleneimine (PEI). The transfected cultured were maintained at 37° C. in an incubateur shaker with 5% CO2 and with agitation at 120 rpm for 6 days. The cells were collected by centrifugation, and the supernatant containing the recombinant His-tagged protein was treated for purification on a Ni-NTA agarose column.

The invention claimed is:

1. An immunoconjugate comprising an anti-Axl antibody, or an Axl-binding fragment thereof, selected from:
   (i) an antibody comprising the three light chain CDRs comprising the sequences of SEQ ID NOs. 1, 2 and 3; and the three heavy chain CDRs comprising the sequences of SEQ ID NOs. 4, 5 and 6;
   (ii) an antibody produced by hybridoma I-4505; deposited at the CNCM, Institut Pasteur, France, on the 28 Jul. 2011;
   (iii) an antibody produced by the hybridoma I-3947 deposited at the CNCM, Institut Pasteur, France, on Mar. 12, 2008;
   (iv) an antibody produced by the hybridoma I-4116 deposited at the CNCM, Institut Pasteur, France, on Jan. 27, 2009;
   (v) an antibody produced by the hybridoma I-4514 deposited at the CNCM, Institut Pasteur, France, on Sep. 15, 2011;
   (vi) an antibody produced by the hybridoma I-4518 deposited at the CNCM, Institut Pasteur, France, on Sep. 15, 2011;
   (vii) an antibody produced by the hybridoma I-4502 deposited at the CNCM, Institut Pasteur, France, on Jul. 28, 2011;
   (viii) an antibody produced by the hybridoma I-4728 deposited at the CNCM, Institut Pasteur, France, on Apr. 4, 2013;
   (ix) an antibody produced by the hybridoma I-4729 deposited at the CNCM, Institut Pasteur, France, on Apr. 4, 2013;
   (x) an antibody produced by the hybridoma I-4510 deposited at the CNCM, Institut Pasteur, France, on Jul. 28, 2011;
   (xi) an antibody produced by the hybridoma I-4506 deposited at the CNCM, Institut Pasteur, France, on Jul. 28, 2011;
   (xii) an antibody produced by the hybridoma I-4507 deposited at the CNCM, Institut Pasteur, France, on Jul. 28, 2011; and
   (xiii) an antibody produced by the hybridoma I-4519 deposited at the CNCM, Institut Pasteur, France, on Sep. 15, 2011.

2. A pharmaceutical composition comprising the immunoconjugate of claim 1 and at least an excipient and/or a pharmaceutical acceptable vehicle.

3. An immunoconjugate having formula (I)

or a pharmaceutically acceptable salt or solvate thereof, wherein:

Ab is an antigen binding protein which i) specifically binds to the protein Axl, and ii) is internalized into a mammalian cell following its binding to said protein Axl when said Axl protein is expressed at the surface of said mammalian cell;

L is a linker;

D is a drug, a toxin and/or a radioisotope;

n is 1 to 12; wherein the antigen binding protein is an antibody selected from:
   (i) an antibody comprising the three light chain CDRs comprising the sequences of SEQ ID NOs. 1, 2 and 3; and the three heavy chain CDRs comprising the sequences of SEQ ID NOs. 4, 5 and 6;
   (ii) an antibody produced by hybridoma I-4505; deposited at the CNCM, Institut Pasteur, France, on 28 Jul. 2011;
   (iii) an antibody produced by the hybridoma I-3947 deposited at the CNCM, Institut Pasteur, France, on Mar. 12, 2008;
   (iv) an antibody produced by the hybridoma I-4116 deposited at the CNCM, Institut Pasteur, France, on Jan. 27, 2009;
   (v) an antibody produced by the hybridoma I-4514 deposited at the CNCM, Institut Pasteur, France, on Sep. 15, 2011;
   (vi) an antibody produced by the hybridoma I-4518 deposited at the CNCM, Institut Pasteur, France, on Sep. 15, 2011;
   (vii) an antibody produced by the hybridoma I-4502 deposited at the CNCM, Institut Pasteur, France, on Jul. 28, 2011;
   (viii) an antibody produced by the hybridoma I-4728 deposited at the CNCM, Institut Pasteur, France, on Apr. 4, 2013;
   (ix) an antibody produced by the hybridoma I-4729 deposited at the CNCM, Institut Pasteur, France, on Apr. 4, 2013;
   (x) an antibody produced by the hybridoma I-4510 deposited at the CNCM, Institut Pasteur, France, on Jul. 28, 2011;
   (xi) an antibody produced by the hybridoma I-4506 deposited at the CNCM, Institut Pasteur, France, on Jul. 28, 2011;
   (xii) an antibody produced by the hybridoma I-4507 deposited at the CNCM, Institut Pasteur, France, on Jul. 28, 2011; and
   (xiii) an antibody produced by the hybridoma I-4519 deposited at the CNCM, Institut Pasteur, France, on Sep. 15, 2011.

4. An immunoconjugate having formula (I)

or a pharmaceutically acceptable salt or solvate thereof, wherein:

Ab is an antigen binding protein which i) specifically binds to the protein Axl with an $EC_{50}$ as low as at least $10^{-9}$ M, and ii) is internalized into a mammalian cell following its binding to said protein Axl when said Axl protein is expressed at the surface of said mammalian cell;

L is a linker;

D is a drug, a toxin and/or a radioisotope;

n is 1 to 12; wherein the antigen binding protein is an antibody selected from:
   (i) an antibody comprising the three light chain CDRs comprising the sequences of SEQ ID NOs. 1, 2 and 3; and the three heavy chain CDRs comprising the sequences of SEQ ID NOs. 4, 5 and 6;
   (ii) an antibody produced by hybridoma I-4505; deposited at the CNCM, Institut Pasteur, France, on 28 Jul. 2011;

(iii) an antibody produced by the hybridoma I-3947 deposited at the CNCM, Institut Pasteur, France, on Mar. 12, 2008;

(iv) an antibody produced by the hybridoma I-4116 deposited at the CNCM, Institut Pasteur, France, on Jan. 27, 2009;

(v) an antibody produced by the hybridoma I-4514 deposited at the CNCM, Institut Pasteur, France, on Sep. 15, 2011;

(vi) an antibody produced by the hybridoma I-4518 deposited at the CNCM, Institut Pasteur, France, on Sep. 15, 2011;

(vii) an antibody produced by the hybridoma I-4502 deposited at the CNCM, Institut Pasteur, France, on Jul. 28, 2011;

(viii) an antibody produced by the hybridoma I-4728 deposited at the CNCM, Institut Pasteur, France, on Apr. 4, 2013;

(ix) an antibody produced by the hybridoma I-4729 deposited at the CNCM, Institut Pasteur, France, on Apr. 4, 2013;

(x) an antibody produced by the hybridoma I-4510 deposited at the CNCM, Institut Pasteur, France, on Jul. 28, 2011;

(xi) an antibody produced by the hybridoma I-4506 deposited at the CNCM, Institut Pasteur, France, on Jul. 28, 2011;

(xii) an antibody produced by the hybridoma I-4507 deposited at the CNCM, Institut Pasteur, France, on Jul. 28, 2011; and (xiii) an antibody produced by the hybridoma I-4519 deposited at the CNCM, Institut Pasteur, France, on Sep. 15, 2011.

5. An immunoconjugate having the formula (I)

$$Ab\text{-}(L\text{-}D)_n \qquad (I)$$

or a pharmaceutically acceptable salt or solvate thereof, wherein:

Ab is an antigen binding protein which i) specifically binds to the protein Axl, and ii) induces a reduction of mean fluorescence intensity (MFI) of at least 200;

L is a linker;

D is a drug, a toxin and/or a radioisotope;

n is 1 to 12; wherein the antigen binding protein is an antibody selected from:

(i) an antibody comprising the three light chain CDRs comprising the sequences of SEQ ID NOs. 1, 2 and 3; and the three heavy chain CDRs comprising the sequences of SEQ ID NOs. 4, 5 and 6;

(ii) an antibody produced by hybridoma I-4505; deposited at the CNCM, Institut Pasteur, France, on the 28 Jul. 2011;

(iii) an antibody produced by the hybridoma I-3947 deposited at the CNCM, Institut Pasteur, France, on Mar. 12, 2008;

(iv) an antibody produced by the hybridoma I-4116 deposited at the CNCM, Institut Pasteur, France, on Jan. 27, 2009;

(v) an antibody produced by the hybridoma I-4514 deposited at the CNCM, Institut Pasteur, France, on Sep. 15, 2011;

(vi) an antibody produced by the hybridoma I-4518 deposited at the CNCM, Institut Pasteur, France, on Sep. 15, 2011;

(vii) an antibody produced by the hybridoma I-4502 deposited at the CNCM, Institut Pasteur, France, on Jul. 28, 2011;

(viii) an antibody produced by the hybridoma I-4728 deposited at the CNCM, Institut Pasteur, France, on Apr. 4, 2013;

(ix) an antibody produced by the hybridoma I-4729 deposited at the CNCM, Institut Pasteur, France, on Apr. 4, 2013;

(x) an antibody produced by the hybridoma I-4510 deposited at the CNCM, Institut Pasteur, France, on Jul. 28, 2011;

(xi) an antibody produced by the hybridoma I-4506 deposited at the CNCM, Institut Pasteur, France, on Jul. 28, 2011;

(xii) an antibody produced by the hybridoma I-4507 deposited at the CNCM, Institut Pasteur, France, on Jul. 28, 2011; and (xiii) an antibody produced by the hybridoma I-4519 deposited at the CNCM, Institut Pasteur, France, on Sep. 15, 2011.

6. An immunoconjugate having the formula (I)

$$Ab\text{-}(L\text{-}D)_n \qquad (I)$$

or a pharmaceutically acceptable salt or solvate thereof, wherein:

Ab is an antigen binding protein which i) specifically binds to the protein Axl with an $EC_{50}$ as low as at least $10^{-9}$ M, and ii) induces a reduction of mean fluorescence intensity (MFI) of at least 200;

L is a linker;

D is a drug, a toxin and/or a radioisotope;

n is 1 to 12; wherein the antigen binding protein is an antibody selected from:

(i) an antibody comprising the three light chain CDRs comprising the sequences of SEQ ID NOs. 1, 2 and 3; and the three heavy chain CDRs comprising the sequences of SEQ ID NOs. 4, 5 and 6;

(ii) an antibody produced by hybridoma I-4505; deposited at the Collection Nationale the Cultures de Microorganisms (Institut Pasteur, Rue du Docteur Roux, Paris, France) (CNCM), France, on 28 Jul. 2011;

(iii) an antibody produced by the hybridoma I-3947 deposited at the CNCM, Institut Pasteur, France, on Mar. 12, 2008;

(iv) an antibody produced by the hybridoma I-4116 deposited at the CNCM, Institut Pasteur, France, on Jan. 27, 2009;

(v) an antibody produced by the hybridoma I-4514 deposited at the CNCM, Institut Pasteur, France, on Sep. 15, 2011;

(vi) an antibody produced by the hybridoma I-4518 deposited at the CNCM, Institut Pasteur, France, on Sep. 15, 2011;

(vii) an antibody produced by the hybridoma I-4502 deposited at the CNCM, Institut Pasteur, France, on Jul. 28, 2011;

(viii) an antibody produced by the hybridoma I-4728 deposited at the CNCM, Institut Pasteur, France, on Apr. 4, 2013;

(ix) an antibody produced by the hybridoma I-4729 deposited at the CNCM, Institut Pasteur, France, on Apr. 4, 2013;

(x) an antibody produced by the hybridoma I-4510 deposited at the CNCM, Institut Pasteur, France, on Jul. 28, 2011;

(xi) an antibody produced by the hybridoma I-4506 deposited at the CNCM, Institut Pasteur, France, on Jul. 28, 2011;

(xii) an antibody produced by the hybridoma I-4507 deposited at the CNCM, Institut Pasteur, France, on Jul. 28, 2011; and (xiii) an antibody produced by the hybridoma I-4519 deposited at the CNCM, Institut Pasteur, France, on Sep. 15, 2011.

7. The immunoconjugate of claim 4, wherein the antigen binding protein binds to the protein Axl with an $EC_{50}$ between $10^{-9}$ and $10^{-12}$.

8. The immunoconjugate of claim 6, wherein the antigen binding protein binds to the protein Axl with an $EC_{50}$ between $10^{-9}$ and 10-12.

* * * * *